(12) United States Patent
Amberg et al.

(10) Patent No.: US 6,509,341 B1
(45) Date of Patent: Jan. 21, 2003

(54) CARBOXYLIC ACID DERIVATIVES, CARRYING AMIDO SIDE-CHAINS; PRODUCTION AND USE AS ENDOTHELIN RECEPTOR ANTAGONISTS

(75) Inventors: Wilhelm Amberg, Schwetzingen (DE); Rolf Jansen, Mannheim (DE); Stefan Hergenröder, Mainz (DE); Manfred Raschack, Weisenheim (DE); Liliane Unger, Ludwigshafen (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/529,860

(22) PCT Filed: Oct. 16, 1998

(86) PCT No.: PCT/EP98/06571

§ 371 (c)(1),
(2), (4) Date: Apr. 20, 2000

(87) PCT Pub. No.: WO99/23078

PCT Pub. Date: May 14, 1999

(30) Foreign Application Priority Data

| Oct. 31, 1997 | (DE) | 197 48 238 |
| Nov. 28, 1997 | (DE) | 197 52 904 |
| Mar. 5, 1998 | (DE) | 198 09 376 |

(51) Int. Cl.$^7$ .............. C07D 239/34; C07D 239/52; C07D 239/60; A61K 31/505; A61P 9/10

(52) U.S. Cl. ............ 514/258; 514/269; 544/253; 544/315; 544/316; 544/319

(58) Field of Search .............. 544/253, 315, 544/316, 319; 514/258, 269

(56) References Cited

U.S. PATENT DOCUMENTS

| 5,661,106 A | * | 8/1997 | Baumann et al. | 544/216 |
| 5,703,017 A | * | 12/1997 | Baumann et al. | 544/219 |
| 5,932,730 A | * | 8/1999 | Riechers et al. | 544/298 |

FOREIGN PATENT DOCUMENTS

| DE | 19614534 | 10/1997 |
| WO | WO 94/25442 | 11/1994 |
| WO | WO 95/26716 | 10/1995 |

* cited by examiner

*Primary Examiner*—Richard L. Raymond
*Assistant Examiner*—Venkataraman Balasubramanian
(74) *Attorney, Agent, or Firm*—Keil & Weinkauf

(57) ABSTRACT

The invention relates to carboxylic acid derivatives of formula (I), wherein the substituents have the meaning as commented in the description. It also relates to the production and use of same as endothelin receptor antagonists.

13 Claims, No Drawings

CARBOXYLIC ACID DERIVATIVES, CARRYING AMIDO SIDE-CHAINS; PRODUCTION AND USE AS ENDOTHELIN RECEPTOR ANTAGONISTS

The present invention relates to novel carboxylic acid derivatives, their preparation and use.

Endothelin is a peptide which is composed of 21 amino acids and is synthesized and released by vascular endothelium. Endothelin exists in three isoforms, ET-1, ET-2 and ET-3. "Endothelin" or "ET" hereinafter refers to one or all isoforms of endothelin. Endothelin is a potent vasoconstrictor and has a strong effect on vessel tone. It is known that this vasoconstriction is caused by binding of endothelin to its receptor (Nature, 332, 411–415, 1988; FEBS Letters, 231, 440–444, 1988 and Biochem. Biophys. Res. Commun., 154, 868–875, 1988).

Elevated or abnormal release of endothelin causes persistent vasoconstriction in peripheral, renal and cerebral blood vessels, which may result in disorders. As reported in the literature, endothelin is involved in a number of disorders. These include: hypertension, acute myocardial infarct, pulmonary hypertension, Raynaud's syndrome, cerebral vasospasms, stroke, benign prostate hypertrophy, atherosclerosis and asthma (J. Vascular Med. Biology 2, 207 (1990), J. Am. Med. Association 264, 2868 (1990), Nature 344, 114 (1990), N. Engl. J. Med. 322, 205 (1989), N. Engl. J. Med. 328, 1732 (1993), Nephron 66, 373 (1994), Stroke 25, 904 (1994), Nature 365, 759 (1993), J. Mol. Cell. Cardiol. 27, A234 (1995); Cancer Research 56, 663 (1996)).

At least two endothelin receptor subtypes, $ET_A$ and $ET_B$ receptors, are currently described in the literature (Nature 348, 730 (1990), Nature 348, 732 (1990)). Accordingly, substances which inhibit the binding of endothelin to the two receptors ought to antagonize the physiological effects of endothelin and therefore represent valuable drugs.

Mixed $ET_A/ET_B$ receptor antagonists have been described in DE Patent Application 19636046.3. The spacer Q (see formula II) is important for these compounds, corresponds in length to a $C_2$–$C_4$-alkyl chain and has the function of producing a defined distance between $R^6$ and W in compounds of the formula II.

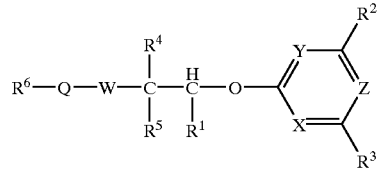

Furthermore, in the patent application WO 97/38980, the following compounds of the formula VII are described as endothelin receptor antagonists:

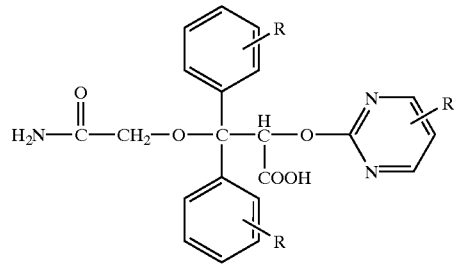

An advantage of these compounds is -said to be the low plasma binding.

We have now found, surprisingly, that the receptor affinity and selectivity can be influenced using the spacer $Q=R^6CR^7R^8$ (see formula I), as a function of $R^6$=amide. Thus, either $ET_A$-selective, $ET_B$-selective or else mixed receptor antagonists [sic] can be prepared.

The antagonists referred to here as $ET_A$ ($ET_B$)-specific antagonists are those whose affinity for the $ET_A$ ($ET_B$) receptor is at least ten times higher than their affinity for the $ET_B$ ($ET_A$) receptor. Preferred compounds are those whose difference in affinity for the two receptors is at least twenty.

Mixed endothelin receptor antagonists are those compounds which bind with approximately the same affinity to the $ET_A$ and $ET_B$ receptors. Approximately the same affinity for receptors exists when the ratio of the affinities is greater than 0.05 (preferably 0.1) and less than 20 (preferably 10).

It is an object of the present invention to identify compounds which belong to one of the three selectivity groups.

We have found that this object is achieved by carboxylic acid derivatives of the formula I

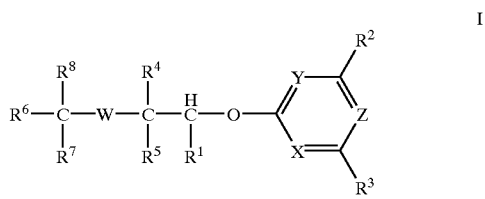

[lacuna] $R^1$ is tetrazole [sic] or a group

where R has the following meaning:
  a) a radical $OR^9$ where $R^9$ is:
    hydrogen, the cation of an alkali metal, the cation of an alkaline earth metal, a physiologically tolerated organic ammonium ion such as tertiary $C_1$–$C_4$-alkylammonium or the ammonium ion;
    $C_3$–$C_8$-cycloalkyl, $C_1$–$C_8$-alkyl, $CH_2$-phenyl, each of which can be substituted by one or more of the following radicals: halogen, nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $NH(C_1$–$C_4$-alkyl), $N(C_1$–$C_4$-alkyl)$_2$;
    a $C_3$–$C_6$-alkenyl—or a $C_3$–$C_6$-alkynyl group, it being possible for these groups in turn to carry one to five halogen atoms;
    $R^9$ can also be a phenyl radical which may carry one to five halogen atoms and/or one to three of the following radicals: nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $NH(C_1$–$C_4$-alkyl), $N(C_1$–$C_4$-alkyl)$_2$;
  b) a 5-membered heteroaromatic system which is linked via a nitrogen atom, such as pyrrolyl, pyrazolyl, imidazolyl and triazolyl, which may carry one or two halogen atoms, or one or two $C_1$–$C_4$-alkyl or one or two $C_1$–$C_4$-alkoxy groups.
  c) a group

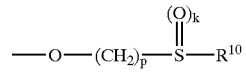

where k can assume the values 0, 1 and 2, p can assume the values 1, 2, 3 and 4, and $R^{10}$ is
    $C_1$–$C_4$-alkyl, $C_3$–$C_8$-cycloalkyl, $C_3$–$C_6$-alkenyl, $C_3$–$C_6$-alkynyl or phenyl, which can be substituted by one or more, e.g. one to three, of the following radicals:

halogen, nitro, cyano, $C_1$–$C_4$-alkyl, $C_1$–$C_4$-haloalkyl, hydroxyl, $C_1$–$C_4$-alkoxy, $C_1$–$C_4$-alkylthio, mercapto, amino, NH($C_1$–$C_4$-alkyl), N($C_1$–$C_4$-alkyl)$_2$.

d) a radical

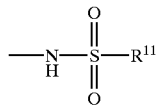

where $R^{11}$ is:

$C_1$–$C_4$-alkyl, $C_1$–$C_4$-haloalkyl, $C_3$–$C_6$-alkenyl, $C_3$–$C_6$-alkynyl, $C_3$–$C_8$-cycloalkyl, it being possible for these radicals to carry a $C_1$–$C_4$-alkoxy, $C_1$–$C_4$-alkylthio and/or a phenyl radical as specified under c);

phenyl, which can be substituted by one to three of the following radicals: halogen, nitro, cyano, $C_1$–$C_4$-alkyl, $C_1$–$C_4$-haloalkyl, hydroxyl, $C_1$–$C_4$-alkoxy, $C_1$–$C_4$-alkylthio, mercapto, amino, NH($C_1$–$C_4$-alkyl), N($C_1$–$C_4$-alkyl)$_2$ The other substituents have the following meanings:

$R^2$ hydrogen, hydroxyl, $NH_2$, NH($C_1$–$C_4$-alkyl), N($C_1$–$C_4$-alkyl)$_2$, halogen, $C_1$–$C_4$-alkyl, $C_2$–$C_4$-alkenyl, $C_2$–$C_4$-alkynyl, $C_1$–$C_4$-hydroxyalkyl, $C_1$–$C_4$-haloalkyl, $C_1$–$C_4$-alkoxy, $C_1$–$C_4$-haloalkoxy or $C_1$–$C_4$-alkylthio, or $CR^2$ is linked to $CR^{10}$ as indicated under Z to give a 5- or 6-membered ring.

X nitrogen or methine.

Y nitrogen or methine.

Z nitrogen or $CR^{12}$, where $R^{12}$ is hydrogen, halogen or $C_1$–$C_4$-alkyl, or $CR^{12}$ forms together with $CR^2$ or $CR^3$ a 5- or 6-membered alkylene or alkenylene ring which can be substituted by one or two $C_1$–$C_4$-alkyl groups and in which in each case one or more methylene groups can be replaced by oxygen, sulfur, —NH or N($C_1$–$C_4$-alkyl).

At least one of the ring members X, Y or Z is nitrogen.

$R^3$ hydrogen, hydroxyl, $NH_2$, NH($C_1$–$C_4$-alkyl), N($C_1$–$C_4$-alkyl)$_2$, halogen, $C_1$–$C_4$-alkyl, $C_2$–$C_4$-alkenyl, $C_2$–$C_4$-alkynyl, $C_1$–$C_4$-haloalkyl, $C_1$–$C_4$-alkoxy, $C_1$–$C_4$-haloalkoxy, $C_1$–$C_4$-hydroxyalkyl, $C_1$–$C_4$-alkylthio, or $CR^3$ is linked to $CR^{12}$ as indicated under Z to give a 5- or 6-membered ring.

$R^4$ and $R^5$ (which can be identical or different):
phenyl or naphthyl, each of which can be substituted by one or more of the following radicals: halogen, nitro, cyano, hydroxyl, mercapto, $C_1$–$C_4$-alkyl, $C_2$–$C_4$-alkenyl, $C_2$–$C_4$-alkynyl, $C_1$–$C_4$-haloalkyl, $C_1$–$C_4$-alkoxy, phenoxy, carboxyl, $C_1$–$C_4$-haloalkoxy, $C_1$–$C_4$-alkylthio, amino, NH($C_1$–$C_4$-alkyl), N($C_1$–$C_4$-alkyl)$_2$ or phenyl which can be substituted one or more times, e.g. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio; or
phenyl or naphthyl which are connected together in ortho positions by a direct linkage, a methylene, ethylene, or ethenylene group, an oxygen or sulfur atom or an $SO_2$, NH or N-alkyl group;
$C_3$–$C_8$-cycloalkyl.

$R^6$ a group

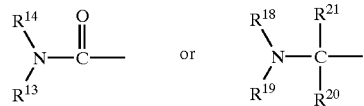

$R^{13}$ and $R^{14}$ (which can be identical or different):
hydrogen, with the proviso that $R^{13}$ and $R^{14}$ must not simultaneously be hydrogen,
$C_1$–$C_8$-alkyl, $C_3$–$C_8$-alkenyl or $C_3$–$C_8$-alkynyl, it being possible for each of these radicals to be substituted one or more times by: halogen, hydroxyl, mercapto, carboxyl, nitro, amino, carboxamide [sic], cyano, $C_1$–$C_4$-alkoxy, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkylcarbonyl, $C_1$–$C_4$-alkoxycarbonyl, $C_3$–$C_8$-alkylcarbonylalkyl, $C_3$–$C_8$-cycloalkyl, 1-indanyl, 2-indanyl, 1-tetrahydronaphthyl, 2-tetrahydronaphthyl, NH($C_1$–$C_4$-alkyl), N($C_1$–$C_4$-alkyl)$_2$, phenoxy or phenyl, it being possible for said aryl radicals in turn to be substituted one or more times, e.g. one to three times, by halogen, hydroxyl, mercapto, carboxyl, nitro, cyano, $C_1$–$C_4$-alkyl, $C_1$–$C_4$-haloalkyl, $C_1$–$C_4$-alkoxy, $C_1$–$C_4$-haloalkoxy, amino, NH($C_1$–$C_4$-alkyl), N($C_1$–$C_4$-alkyl)$_2$, or $C_1$–$C_4$-alkylthio;
$C_3$–$C_8$-cycloalkyl, it being possible for each of these radicals to be substituted one or more times by: halogen, hydroxyl, mercapto, carboxyl, nitro, cyano, $C_1$–$C_4$-alkyl, $C_2$–$C_4$-alkenyl, $C_2$–$C_4$-alkynyl, $C_1$–$C_4$-alkoxy, $C_1$–$C_4$-alkylthio, $C_1$–$C_4$-haloalkoxy;
phenyl or naphthyl, each of which can be substituted by one or more of the following radicals: halogen, nitro, carboxamide [sic], mercapto, carboxyl, cyano, hydroxyl, amino, $R^{15}$, $C_1$–$C_4$-alkyl, $C_2$–$C_4$-alkenyl, $C_2$–$C_4$-alkynyl, $C_3$–$C_6$-alkenyloxy, $C_1$–$C_4$-haloalkyl, $C_3$–$C_6$-alkynyloxy, $C_1$–$C_4$-alkylcarbonyl, $C_1$–$C_4$-alkoxycarbonyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, dioxomethylene [sic], dioxoethylene [sic] or phenyl, which can be substituted onr or more times, e.g. one to three times, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
or $R^{13}$ and $R^{14}$ together form a $C_3$–$C_7$-alkylene chain which is closed to a ring and which can be substituted one or more times by $C_1$–$C_4$-alkyl, $C_1$–$C_4$-alkylthio, $C_1$–$C_4$-alkoxy, $C_1$–$C_4$-haloalkyl, $C_1$–$C_4$-haloalkoxy, and in which one alkylene [sic] group can be replaced by oxygen, sulfur, nitrogen or N($C_1$–$C_4$-alkyl), such as —(CH$_2$)$_4$—, —(CH$_2$)$_5$—, —(CH$_2$)$_6$—, —(CH$_2$)$_7$—, —(CH$_2$)$_2$—O—(CH$_2$)$_2$—, —(CH$_2$)$_2$—S—(CH$_2$)$_2$—, —(CH$_2$)$_2$—NH—(CH$_2$)$_2$—, —(CH$_2$)$_3$—, —(CH$_2$)$_2$—N(CH$_3$)—(CH$_2$)$_2$—;
or $R^{13}$ and $R^{14}$ together form a $C_3$–$C_7$-alkylene chain or $C_4$–$C_7$-alkenylene chain, which is closed to a ring and each of which can be substituted one to three times by $C_1$–$C_4$-alkyl and to each of which is fused a phenyl ring which can be substituted one or more times by halogen, $C_1$–$C_4$-alkyl, $C_1$–$C_4$-alkylthio, $C_1$–$C_4$-alkoxy, $C_1$–$C_4$-haloalkyl, $C_1$–$C_4$-haloalkoxy, hydroxyl, carboxyl, amino, carboxamide [sic].

$R^7$ and $R^8$ (which can be identical or different):
hydrogen, $C_1$–$C_4$-alkyl.

$R^{15}$ $C_1$–$C_4$-alkyl, $C_1$–$C_4$-alkylthio, $C_1$–$C_4$-alkoxy, each of which carry one of the following radicals: hydroxyl, carboxyl, amino, NH($C_1$–$C_4$-alkyl), N($C_1$–$C_4$-alkyl)$_2$, carboxamide [sic] or CON($C_1$–$C_4$-alkyl)$_2$.

$R^{18}$ hydrogen;
- $C_1$–$C_8$-alkyl, $C_3$–$C_8$-alkenyl or $C_3$–$C_8$-alkynyl, where each of these radicals can be substituted one or more times by: halogen, carboxyl, cyano, $C_1$–$C_4$-alkoxy, $C_1$–$C_4$-alkylthio, $C_1$–$C_4$-haloalkoxy, $C_1$–$C_4$-alkylcarbonyl, $C_1$–$C_4$-alkoxycarbonyl, $C_3$–$C_8$-cycloalkyl, amino, NH($C_1$–$C_4$-alkyl), N($C_1$–$C_4$-alkyl)$_2$, phenoxy or phenyl, where the abovementioned aryl radicals for their part can be substituted one or more times, for example one to three times by halogen, hydroxyl, mercapto, carboxyl, nitro, cyano, $C_1$–$C_4$-alkyl, $C_1$–$C_4$-haloalkyl, $C_1$–$C_4$-alkoxy, $C_1$–$C_4$-haloalkoxy, amino, NH($C_1$–$C_4$-alkyl), N($C_1$–$C_4$-alkyl)$_2$, or $C_1$–$C_4$-alkylthio;
- $C_3$–$C_8$-cycloalkyl, where each of these radicals can be substituted one or more times by: halogen, $C_1$–$C_4$-alkyl;
- phenyl or naphthyl, each of which can be substituted by one or more of the following radicals: halogen, nitro, mercapto, carboxyl, cyano, hydroxyl, amino, $R^{15}$, $C_1$–$C_4$-alkyl, $C_2$–$C_4$-alkenyl, $C_2$–$C_4$-alkynyl, $C_1$–$C_4$-haloalkyl, $C_1$–$C_4$-alkylcarbonyl, $C_1$–$C_4$-alkoxycarbonyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, dioxomethylene [sic], dioxoethylene [sic] or phenyl which can be substituted one or more times, for example one to three times by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

$R^{19}$ $C_1$–$C_8$-alkylcarbonyl, $C_2$–$C_8$-alkenylcarbonyl or $C_2$–$C_8$-alkynylcarbonyl, where each of these radicals can be substituted one or more times by: halogen, $C_1$–$C_4$-alkoxy, $C_1$–$C_4$-alkylthio, $C_1$–$C_4$-haloalkoxy, $C_1$–$C_4$-alkoxycarbonyl, $C_3$–$C_8$-cycloalkyl, phenoxy or phenyl, where the abovementioned aryl radicals for their part can be substituted one or more times, for example one to three times by halogen, hydroxyl, mercapto, carboxyl, nitro, cyano, $C_1$–$C_4$-alkyl, $C_1$–$C_4$-haloalkyl, $C_1$–$C_4$-alkoxy, $C_1$–$C_4$-haloalkoxy, amino, NH($C_1$–$C_4$-alkyl), N($C_1$–$C_4$-alkyl)$_2$, or $C_1$–$C_4$-alkylthio;
- benzyloxycarbonyl, $C_3$–$C_8$-cycloalkylcarbonyl, where each of these radicals can be substituted one or more times by: halogen, $C_1$–$C_4$-alkyl;
- phenylcarbonyl or naphthylcarbonyl, each of which can be substituted by one or more of the following radicals: halogen, nitro, mercapto, carboxyl, cyano, hydroxyl, amino, $R^{15}$, $C_1$–$C_4$-alkyl, $C_2$–$C_4$-alkenyl, $C_2$–$C_4$-alkynyl, $C_3$–$C_6$-alkenyloxy, $C_1$–$C_4$-haloalkyl, $C_3$–$C_6$-alkynyloxy, $C_1$–$C_4$-alkylcarbonyl, $C_1$–$C_4$-alkoxycarbonyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, dioxomethylene [sic], dioxoethylene [sic] or phenyl which can be substituted one or more times, for example one to three times by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
- $C_1$–$C_8$-alkylsulfonyl, $C_3$–$C_8$-alkenylsulfonyl or $C_3$–$C_8$-alkynylsulfonyl, where each of these radicals can be substituted one or more times by: halogen, $C_1$–$C_4$-alkoxy, phenyl, where the abovementioned aryl radical for its part can be substituted one or more times, for example one to three times by halogen, $C_1$–$C_4$-alkyl, $C_1$–$C_4$-haloalkyl, $C_1$–$C_4$-alkoxy, amino, NH($C_1$–$C_4$-alkyl), N($C_1$–$C_4$-alkyl)$_2$, or $C_1$–$C_4$-alkylthio;
- $C_3$–$C_8$-cycloalkylsulfonyl;
- phenylsulfonyl or naphthylsulfonyl, each of which can be substituted by one or more of the following radicals: halogen, cyano, hydroxyl, amino, $R^{15}$, $C_1$–$C_4$-alkyl, $C_2$–$C_4$-alkenyl, $C_2$–$C_4$-alkynyl, $C_3$–$C_6$-alkenyloxy, $C_1$–$C_4$-haloalkyl, $C_1$–$C_4$-alkoxycarbonyl, $C_1$–$C_4$-alkoxy, $C_1$–$C_4$-haloalkoxy, dioxomethylene [sic], dioxoethylene [sic] or phenyl which can be substituted one or more times, for example one to three times by halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio.

$R^{20}$ hydrogen;
- $C_1$–$C_4$-alkyl, where each of these radicals can be substituted one or more times by: halogen, hydroxyl, mercapto, carboxyl, amino, $C_1$–$C_4$-alkoxy, $C_1$–$C_4$-alkylthio, $C_1$–$C_4$-haloalkoxy, $C_1$–$C_4$-alkoxycarbonyl, $C_3$–$C_8$-cycloalkyl, NH($C_1$–$C_4$-alkyl), N($C_1$–$C_4$-alkyl)$_2$, indolyl, phenoxy or phenyl, where the abovementioned aryl radicals for their part can be substituted one or more times, for example one to three times by halogen, hydroxyl, mercapto, carboxyl, $C_1$–$C_4$-alkyl, $C_1$–$C_4$-haloalkyl, $C_1$–$C_4$-alkoxy, $C_1$–$C_4$-haloalkoxy, amino, NH($C_1$–$C_4$-alkyl), N($C_1$–$C_4$-alkyl)$_2$ or $C_1$–$C_4$-alkylthio.

$R^{21}$ hydrogen, $C_1$–$C_4$-alkyl.

W sulfur or oxygen.

In these cases and hereinafter, the following definitions apply:

An alkali metal is, for example, lithium, sodium, potassium;

An alkaline earth metal is, for example, calcium, magnesium, barium;

$C_3$–$C_8$-cycloalkyl is, for example, cyclopropyl, cyclobutyl, cyclopentyl, cyclohexyl, cycloheptyl or cyclooctyl;

$C_1$–$C_4$-haloalkyl can be linear or branched such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl;

$C_1$–$C_4$-haloalkoxy can be linear or branched such as difluoromethoxy, trifluoromethoxy, chlorodifluoromethoxy, 1-fluoroethoxy, 2,2-difluoroethoxy, 1,1,2,2-tetrafluoroethoxy, 2,2,2-trifluoroethoxy, 2-chloro-1,1,2-trifluoroethoxy, 2-fluoroethoxy or pentafluoroethoxy;

$C_1$–$C_4$-alkyl can be linear or branched such as methyl, ethyl, 1-propyl, 2-propyl, 2-methyl-2-propyl, 2-methyl-1-propyl, 1-butyl or 2-butyl;

$C_2$–$C_4$-alkenyl can be linear or branched such as ethenyl, 1-propen-3-yl, 1-propen-2-yl, 1-propen-1-yl, 2-methyl-1-propenyl, 1-butenyl or 2-butenyl;

$C_2$–$C_4$-alkynyl can be linear or branched such as ethynyl, 1-propyn-1-yl, 1-propyn-3-yl, 1-butyn-4-yl or 2-butyn-4-yl;

$C_1$–$C_4$-alkoxy can be linear or branched such as methoxy, ethoxy, propoxy, 1-methylethoxy, butoxy, 1-methylpropoxy, 2-methylpropoxy or 1,1-dimethylethoxy;

$C_3$–$C_6$-alkenyloxy can be linear or branched such as allyloxy, 2-buten-1-yloxy or 3-buten-2-yloxy;

$C_3$–$C_6$-alkynyloxy can be linear or branched such as 2-propyn-1-yloxy, 2-butyn-1-yloxy or 3-butyn-2-yloxy;

$C_1$–$C_4$-alkylthio can be linear or branched such as methylthio, ethylthio, propylthio, 1-methylethylthio, butylthio, 1-methylpropylthio, 2-methylpropylthio or 1,1-dimethylethylthio;

$C_1$–$C_4$-alkylcarbonyl can be linear or branched such as acetyl, ethylcarbonyl or 2-propylcarbonyl, 1-propylcarbonyl, 1-butylcarbonyl;

$C_1$–$C_4$-alkoxycarbonyl can be linear or branched such as methoxycarbonyl, ethoxycarbonyl, n-propoxycarbonyl, i-propoxycarbonyl or n-butoxycarbonyl;

$C_3$–$C_8$-alkylcarbonylalkyl can be linear or branched such as 2-oxo-1-propyl, 3-oxo-1-butyl or 3-oxo-2-butyl $C_1$–$c_8$-alkyl can be linear or branched such as $C_1$–$C_4$-alkyl, pentyl, hexyl, heptyl or octyl;

$C_1$–$C_8$-alkylcarbonyl can be linear or branched such as $C_1$–$C_4$-alkylcarbonyl, 1-pentylcarbonyl, 1-hexylcarbonyl, 1-heptylcarbonyl or 1-octylcarbonyl;

$C_2$–$C_8$-alkenylcarbonyl can be linear or branched such as ethenylcarbonyl, 1-propen-3-ylcarbonyl, 1-propen-2-ylcarbonyl, 1-propen-1-ylcarbonyl, 2-methyl-1-propenylcarbonyl, 1-buten-1-ylcarbonyl, 1-penten-1-ylcarbonyl, 1-octen-1-ylcarbonyl;

$C_2$–$C_8$-alkynylcarbonyl can be linear or branched such as ethynylcarbonyl, 1-propyn-3-ylcarbonyl, 1-propyn-1-ylcarbonyl, 1-butyn-1-ylcarbonyl, 1-pentyn-1-ylcarbonyl, 1-octyn-1-ylcarbonyl;

$C_3$–$C_8$-cycloalkylcarbonyl, cyclopropylcarbonyl, cyclobutylcarbonyl, cyclopentylcarbonyl, cyclohexylcarbonyl, 4-methylcyclohex-1-ylcarbonyl, cycloheptylcarbonyl or cyclooctylcarbonyl;

$C_1$–$C_4$-alkylsulfonyl can be linear or branched such as methylsulfonyl, ethylsulfonyl or 2-propylsulfonyl, 1-propylsulfonyl, 2-methyl-1-propylsulfonyl, 1-butylsulfonyl;

$C_1$–$C_8$-alkylsulfonyl can be linear or branched such as $C_1$–$C_4$-alkylsulfonyl, 1-pentylsulfonyl, 1-hexylsulfonyl, 1-heptylsulfonyl or 1-octylsulfonyl;

$C_3$–$C_8$-alkenylsulfonyl can be linear or branched such as 1-propen-3-ylsulfonyl, 1-propen-2-ylsulfonyl, 1-propen-1-ylsulfonyl, 2-methyl-1-propen-1-ylsulfonyl, 1-buten-1-ylsulfonyl, 1-penten-1-ylsulfonyl, 1-octen-1-ylsulfonyl;

$C_3$–$C_8$-alkynylsulfonyl can be linear or branched such as 1-propyn-3-ylsulfonyl, 1-propyn-1-ylsulfonyl, 1-butyn-1-ylsulfonyl, 1-pentyn-1-ylsulfonyl, 1-octyn-1-ylsulfonyl;

$C_3$–$C_8$-cycloalkylsulfonyl is, for example, cyclopropylsulfonyl, cyclobutylsulfonyl, cyclopentylsulfonyl, cyclohexylsulfonyl, 4-methylcyclohex-1-ylsulfonyl, cycloheptylsulfonyl or cyclooctylsulfonyl;

halogen is, for example, fluorine, chlorine, bromine, iodine.

The invention further relates to those compounds from which the compounds of the formula I can be liberated (called prodrugs).

Preferred prodrugs are those for which the liberation takes place under conditions like those prevailing in certain compartments of the body, e.g. in the stomach, intestine, bloodstream, liver.

The compounds I and the intermediates for preparing them, such as III, IV and V, may have one or more asymmetrically substituted carbon atoms. Compounds of this type can exist as pure enantiomers or pure diastereomers or as mixture thereof. The use of an enantiomerically pure compound as active ingredient is preferred.

The invention further relates to the use of the abovementioned carboxylic acid derivatives for producing drugs, in particular for producing inhibitors for $ET_A$ and $ET_B$ receptors. The compounds according to the invention are suitable as selective and as mixed antagonists as have been defined at the outset.

Compound of the formula V where W is sulfur or oxygen can be prepared as described in WO 96/11914.

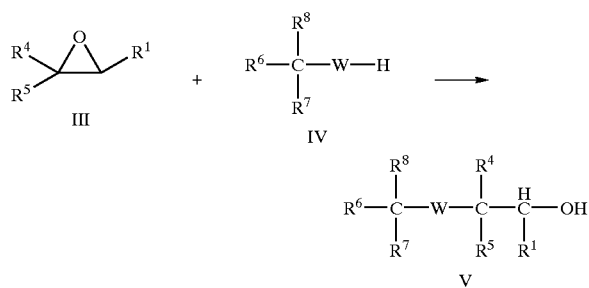

Compounds of the formula V can be obtained in enantiomerically pure form by starting from enantiomerically pure compounds of the formula III and reacting them with compounds of the formula IV as described in WO 96/11914.

It is additionally possible to obtain enantiomeric compounds of the formula V by subjecting racemic or diastereomeric compounds of the formula V to a conventional racemate resolution using suitable enantiomerically pure bases. Examples of suitable bases of this type are 4-chlorophenylethylamine and the bases mentioned in WO 96/11914.

It is moreover possible to obtain enantiomerically pure compounds of the formula V by acid-catalyzed transetherification as described in DE 19636046.3.

The preparation of compounds of the formula III has been described in WO 96/11914, whereas compounds of the formula IVa ($R^6$=amide) or IVb ($R^6$=sulfonamide/amide) either are known or can be synthesized by generally known methods, such as:

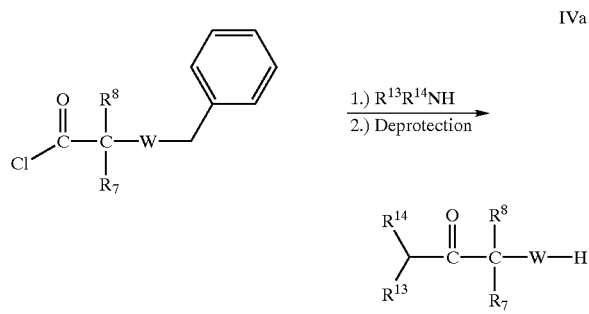

-continued

IVb

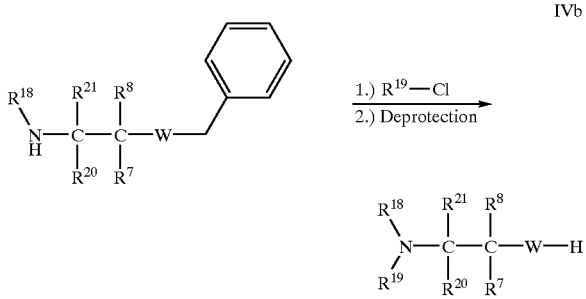

1.) $R^{19}$—Cl
2.) Deprotection

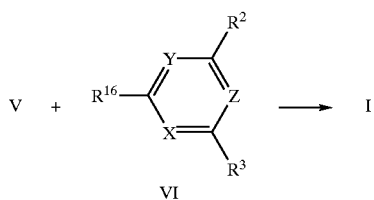

The compounds according to the invention in which the substituents have the meanings stated under formula I can be prepared, for example, by reacting the carboxylic acid derivatives of the formula V in which the substituents have the stated meanings with compounds of the formula VI.

$$V + R^{16}\!\!-\!\!\underset{VI}{\underset{R^3}{\overset{R^2}{\text{ring}}}} \longrightarrow I$$

In formula VI, $R^{16}$ is halogen or $R^{17}$—$SO_2$—, where $R^{17}$ can be $C_1$–$C_4$-alkyl, $C_1$–$C_4$-haloalkyl or phenyl. In addition, at least one of the ring members X or Y or Z is nitrogen. The reaction preferably takes place in an inert solvent or diluent with the addition of a suitable base, ie. a base which deprotonates the intermediate V, at a temperature in the range from room temperature to the boiling point of the solvent.

Compounds of type I with $R^1$=COOH can be obtained directly in this way if the intermediate V where $R^1$ is COOH is deprotonated with two equivalents of a suitable base and reacted with compounds of the formula V. This reaction also takes place in an inert solvent and at a temperature in the range from room temperature to the boiling point of the solvent. Examples of such solvents or diluents are aliphatic, alicyclic and aromatic hydrocarbons, each of which may be chlorinated, such as hexane, cyclohexane, petroleum ether, naphtha, benzene, toluene, xylene, methylene chloride, chloroform, carbon tetrachloride, ethyl chloride and trichloroethylene, ethers, such as diisopropyl ether, dibutyl ether, methyl tert-butyl ether, propylene oxide, dioxane and tetrahydrofuran, nitriles such as acetonitrile and propionitrile, amides such as dimethylformamide, dimethylacetamide and N-methylpyrrolidone, sulfoxides and sulfones, for example dimethyl sulfoxide and sulfolane.

Compounds of the formula VI are known, some of them can be bought or they can be prepared in a generally known manner.

It is possible to use as base an alkali metal or alkaline earth metal hydride such as sodium hydride potassium hydride or calcium hydride, a carbonate such as alkali metal carbonate, e.g. sodium or potassium carbonate, an alkali metal or alkaline earth metal hydroxide such as sodium or potassium hydroxide, an organometallic compound such as butyllithium or an alkali metal amide such as lithium diisopropylamide or lithium amide.

Compounds of the formula I can also be prepared by starting from the corresponding carboxylic acids, ie. compounds of the formula I where $R^1$ is COOH, and first converting them in a conventional way into an activated form such as an acid halide, an anhydride or imidazolide, and then reacting the latter with an appropriate hydroxyl compound $HOR^9$. This reaction can be carried out in conventional solvents and often requires addition of a base, in which case those mentioned above are suitable. These two steps can also be simplified, for example, by allowing the carboxylic acid to act on the hydroxyl compound in the presence of a dehydrating agent such as a carbodiimide.

It is additionally possible to prepare compounds of the formula I also by starting from salts of the corresponding carboxylic acids, ie. from compounds of the formula I where $R^1$ is a group COOM where M can be an alkali metal cation or the equivalent of an alkaline earth metal cation. These salts can be reacted with many compounds of the formula R—A, where A is a conventional nucleofugic leaving group, for example halogen such as chlorine, bromine, iodine or unsubstituted or halogen-, alkyl- or haloalkyl-substituted aryl- or alkylsulfonyl such as toluenesulfonyl and methylsulfonyl, or another equivalent leaving group. Compounds of the formula R—A having a reactive substituent A are known or can easily be obtained with general expert knowledge. This reaction can be carried out in conventional solvents and is advantageously undertaken with addition of a base, in which case those mentioned above are suitable.

It is necessary in some cases for preparing the compounds I according to the invention to use generally known protective group techniques. If, for example, $R^{13}$ is 4-hydroxyphenyl, the hydroxyl group can be initially protected as benzyl ether, which is then cleaved at a suitable stage in the reaction sequence.

Compounds of he formula I where $R^1$ is tetrazole [sic] can be prpared as described in WO 96/11914.

With a view to the biological effect, preferred carboxylic acid derivatives of the formula I, both as pure enantiomers and pure diastereomers and as mixture thereof, are those where the substituents have the following meanings:

$R^2$ hydrogen, hydroxyl, halogen, $N(C_1$–$C_4$-alkyl$)_2$, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-hydroxyalkyl, or $CR^2$ is linked to $CR^{12}$ as indicated under Z to give a 5- or 6-membered ring;

X nitrogen or methine;

Y nitrogen or methine;

Z nitrogen or $CR^{12}$, where $R^{12}$ is hydrogen, fluorine or $C_1$–$C_4$-alkyl, or $CR^{12}$ forms together with $CR^2$ or $CR^3$ a 5- or 6-membered alkylene or alkenylene ring which can be substituted by one or two methyl groups and in each of which a methylene group can be replaced by oxygen or sulfur, such as —$CH_2$-$CH_2$—O—, —$CH_2$-$CH_2$-$CH_2$—O—, —CH=CH—O—, —CH=CH—$CH_2$O—, —CH($CH_3$)—CH($CH_3$)—O—, —CH=C($CH_3$)—O—, —C($CH_3$)=C($CH_3$)—O—, or —C($CH_3$)=C($CH_3$)—S;

At least one of the ring members X, Y or Z is nitrogen.

$R^3$ hydrogen, hydroxyl, halogen, $N(C_1$–$C_4$-alkyl$)_2$, $C_1$–$C_4$-alkyl, $C_1$–$C_4$-alkoxy, $C_1$–$C_4$-alkylthio, $C_1$–$C_4$-haloalkyl, $C_1$–$C_4$-hydroxyalkyl, $C_1$–$C_4$-haloalkoxy, or $CR^3$ is linked to $CR^{10}$ as indicated under Z to give a 5- or 6-membered ring;

$R^4$ and $R^5$ (which may be identical or different):

phenyl or naphthyl, each of which may be substituted by one or more of the following radicals: halogen, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, NH($C_1$–$C_4$-alkyl) or N($C_1$–$C_4$-alkyl)$_2$ or phenyl which may be substituted one or more times, e.g. one to three times, by halogen, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio; or phenyl or naphthyl which are connected together in ortho positions by a direct linkage, a methylene, ethylene or ethenylene group, an oxygen or sulfur atom or an SO$_2$—, NH— or N-alkyl group $C_3$–$C_8$-cycloalkyl;

$R^6$ a group

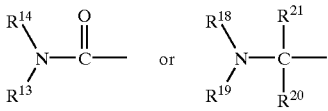

where the molecular weight of the groups $R^{13}$ and $R^{14}$ taken together must be at least 60.

$R^{13}$ and $R^{14}$ (which may be identical or different):
hydrogen, $C_1$–$C_8$-alkyl, $C_3$–$C_8$-alkenyl or $C_3$–$C_8$-alkynyl, it being possible for each of these radicals to be substituted one or more times by: halogen, hydroxyl, mercapto, carboxyl, amino, cyano, $C_1$–$C_4$-alkoxy, $C_1$–$C_4$-alkylthio, $C_1$–$C_4$-haloalkoxy, $C_1$–$C_4$-alkylcarbonyl, $C_1$–$C_4$-alkoxycarbonyl, $C_3$–$C_8$-cycloalkyl, NH($C_1$–$C_4$-alkyl), N($C_1$–$C_4$-alkyl)$_2$, phenoxy or phenyl, it being possible for said aryl radicals in turn to be substituted once to three tiems by halogen, hydroxyl, carboxyl, cyano, $C_1$–$C_4$-alkyl, $C_1$–$C_4$-haloalkyl, $C_1$–$C_4$-alkoxy, $C_1$–$C_4$-haloalkoxy, N($C_1$–$C_4$-alkyl)$_2$, or $C_1$–$C_4$-alkylthio;

$C_3$–$C_8$-cycloalkyl, it being possible for each of these radicals to be substituted one or more times by: halogen, hydroxyl, mercapto, carboxyl, cyano, $C_1$–$C_4$-alkyl, $C_1$–$C_4$-alkoxy, $C_1$–$C_4$-alkylthio, $C_1$–$C_4$-haloalkoxy;

phenyl or naphthyl, each of which may be substituted by one or more of the following radicals: halogen, carboxyl, hydroxyl, amino, $R^{15}$, $C_1$–$C_4$-alkyl, $C_1$–$C_4$-alkoxy, $C_1$–$C_4$-alkylthio, $C_1$–$C_4$-haloalkyl, $C_1$–$C_4$-alkylcarbonyl, $C_1$–$C_4$-alkoxycarbonyl, $C_1$–$C_4$-haloalkoxy, phenoxy, NH($C_1$–$C_4$-alkyl), N($C_1$–$C_4$-alkyl)$_2$, dioxomethylene [sic], dioxoethylene [sic] or phenyl which can be substituted once to three times by halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

or $R^{13}$ and $R^{14}$ together form a $C_3$–$C_7$-alkylene chain which is closed to a ring and which may be substituted one or more times by $C_1$–$C_4$-alkyl, $C_1$–$C_4$-haloalkyl, and in which one alkylene [sic] group can be replaced by oxygen or sulfur, such as —(CH$_2$)$_3$—, —(CH$_2$)$_4$—, —(CH$_2$)$_5$—, —(CH$_2$)$_6$—, —(CH$_2$)$_7$—, —(CH$_2$)$_2$—O—(CH$_2$)$_2$—, —(CH$_2$)$_2$—S—(CH$_2$)$_2$—;

or $R^{13}$ and $R^{14}$ together form a $C_3$–$C_7$-alkylene chain or $C_4$–$C_7$-alkenylene chain which is closed to a ring and to which a phenyl ring is fused, such as 7-azabicyclo[4.2.0]octa-1,3,5-triene, 2,3-dihydroindole, indole, 1,3-dihydroisoindole, 1,2,3,4-tetrahydroquinoline, 1,2,3,4-tetrahydroisoquinoline, it being possible for the phenyl ring in each case to be substituted once to three times by halogen, $C_1$–$C_4$-alkyl, $C_1$–$C_4$-alkoxy, $C_1$–$C_4$-haloalkyl, $C_1$–$C_4$-haloalkoxy, hydroxyl, carboxyl.

The molecular weight of the groups $R^{13}$ and $R^{14}$ taken together must be at least 46.

$R^7$ and $R^8$ (which may be identical or different):
hydrogen, $C_1$–$C_4$-alkyl.

$R^{15}$ $C_1$–$C_4$-alkyl, $C_1$–$C_4$-alkoxy, each of which may carry one of the following radicals: hydroxyl, carboxyl, amino, NH($C_1$–$C_4$-alkyl), N($C_1$–$C_4$-alkyl)$_2$, carboxamide [sic] or CON($C_1$–$C_4$-alkyl)$_2$.

$R^{18}$ hydrogen;
$C_1$–$C_4$-alkyl, $C_3$–$C_4$-alkenyl or $C_3$–$C_4$-alkynyl, where each of these radicals can be substituted one or more times by: halogen, $C_1$–$C_4$-alkoxy, $C_1$–$C_4$-alkylthio, $C_1$–$C_4$-haloalkoxy, $C_3$–$C_8$-cycloalkyl, phenoxy or phenyl, where the abovementioned aryl radicals for their part can be substituted one or more times, for example one to three times by halogen, hydroxyl, $C_1$–$C_4$-alkyl, $C_1$–$C_4$-haloalkyl, $C_1$–$C_4$-alkoxy or $C_1$–$C_4$-alkylthio;

$C_3$–$C_8$-cycloalkyl, where each of these radicals can be substituted one or more times by: $C_1$–$C_4$-alkyl;

phenyl or naphthyl, each of which can be substituted by one or more of the following radicals: halogen, hydroxyl, $R^{15}$, $C_1$–$C_4$-alkyl, $C_1$–$C_4$-alkoxycarbonyl, $C_1$–$C_4$-alkoxy, $C_1$–$C_4$-alkylthio, dioxomethylene [sic], dioxoethylene [sic] or phenyl which can be substituted one or more times, for example one to three times by halogen, $C_1$–$C_4$-alkyl, $C_1$–$C_4$-haloalkyl, $C_1$–$C_4$-alkoxy;

$R^{19}$ $C_1$–$C_4$-alkylcarbonyl, $C_2$–$C_4$-alkenylcarbonyl or $C_2$–$C_4$-alkynylcarbonyl, where each of these radicals can be substituted one or more times by: halogen, $C_1$–$C_4$-alkoxy, $C_3$–$C_8$-cycloalkyl, phenoxy or phenyl, where the abovementioned aryl radicals for their part can be substituted one or more times, for example one to three times by halogen, $C_1$–$C_4$-alkyl, $C_1$–$C_4$-haloalkyl, $C_1$–$C_4$-alkoxy or $C_1$–$C_4$-alkylthio;

$C_3$–$C_8$-cycloalkylcarbonyl, where each of these radicals can be substituted one or more times by: $C_1$–$C_4$-alkyl;

phenylcarbonyl or naphthylcarbonyl, each of which can be substituted by one or more of the following radicals: halogen, cyano, hydroxyl, $R^{15}$, $C_1$–$C_4$-alkyl, $C_1$–$C_4$-haloalkyl, $C_1$–$C_4$-alkylcarbonyl, $C_1$–$C_4$-alkoxycarbonyl, $C_1$–$C_4$-alkoxy, phenoxy, $C_1$–$C_4$-alkylthio, dioxomethylene [sic], dioxoethylene [sic] or phenyl which can be substituted one or more times, for example one to three times by halogen, $C_1$–$C_4$-alkyl, $C_1$–$C_4$-haloalkyl, $C_1$–$C_4$-alkoxy, or $C_1$–$C_4$-alkylthio;

$C_1$–$C_4$-alkylsulfonyl, where each of these radicals can be substituted one or more times by: halogen, $C_1$–$C_4$-alkoxy, phenyl, where the abovementioned aryl radical for its part can be substituted one to three times by halogen, $C_1$–$C_4$-alkyl, $C_1$–$C_4$-haloalkyl, $C_1$–$C_4$-alkoxy or $C_1$–$C_4$-alkylthio;

$C_3$–$C_8$-cycloalkylsulfonyl; phenylsulfonyl or naphthylsulfonyl, each of which can be substituted by one or more of the following radicals: halogen, cyano, $R^{15}$, $C_1$–$C_4$-alkyl, $C_1$–$C_4$-alkoxy, dioxomethylene [sic], dioxoethylene [sic] or phenyl which can be substituted one to three times by halogen, $C_1$–$C_4$-alkyl, $C_1$–$C_4$-haloalkyl, $C_1$–$C_4$-alkoxy or $C_1$–$C_4$-alkylthio;

$R^{20}$ hydrogen;
$C_1$–$C_4$-alkyl, where each of these radicals can be monosubstituted by: hydroxyl, mercapto, carboxyl, amino, $C_3$–$C_8$-cycloalkyl, indolyl, phenoxy or phenyl, where the abovementioned aryl radicals for their part can be substituted one to three times by halogen, hydroxyl, mercapto, carboxyl, $C_1$–$C_4$-alkyl, $C_1$–$C_4$-alkoxy, amino or $C_1$–$C_4$-alkylthio.

$R^{21}$ hydrogen, $C_1$–$C_4$-alkyl.

W sulfur or oxygen;

Particularly preferred compounds of the formula I, both as pure enantiomers and pure diastereomers or as mixture thereof, are those where the substituents have the following meanings:

$R^2$ trifluoromethyl, $C_1$–$C_4$-alkyl, $C_1$–$C_4$-alkoxy, $C_1$–$C_4$-alkylthio, hydroxymethyl, or $CR^2$ is linked to $CR^{12}$ as indicated under Z to give a 5- or 6-membered ring;

X nitrogen or methine;

Y nitrogen or methine;

Z nitrogen or $CR^{12}$ where $R^{12}$ are [sic] hydrogen, fluorine or $C_1$–$C_4$-alkyl, or $CR^{12}$ forms together with $CR^2$ or $CR^3$ einen 5- or 6-membered alkylene or alkenylene ring which may be substituted by one or two methyl groups, and in each of which one methylene group can be replaced by oxygen or sulfur, such as —$CH_2$—$CH_2$—O—, —CH=CH—O—, —CH($CH_3$)—CH($CH_3$)—O—, —C($CH_3$)=C($CH_3$)—O—;

at least one of the ring members X, Y or Z is nitrogen;

$R^3$ trifluoromethyl, $C_1$–$C_4$-alkyl, $C_1$–$C_4$-alkoxy, $C_1$–$C_4$-alkylthio, hydroxymethyl, or $CR^3$ is linked to $CR^{12}$ as indicated under Z to give a 5- or 6-membered ring;

$R^4$ and $R^5$ (which may be identical or different):

phenyl or naphthyl, each of which may be substituted by one or more of the following radicals: halogen, hydroxyl, $C_1$–$C_4$-alkyl, $C_1$–$C_4$-haloalkyl, $C_1$–$C_4$-alkoxy, $C_1$–$C_4$-haloalkoxy, NH($C_1$–$C_4$-alkyl), N($C_1$–$C_4$-alkyl)$_2$, phenoxy or phenyl, which may be substituted once to three times by halogen, $C_1$–$C_4$-alkyl, $C_1$–$C_4$-haloalkyl, $C_1$–$C_4$-alkoxy or $C_1$–$C_4$-haloalkoxy; or phenyl or naphthyl which are connected together in ortho positions by a direct linkage, a methylene, ethylene or ethenylene group, an oxygen or sulfur atom or an $SO_2$—, NH— or N-alkyl group $C_5$–$C_7$-cycloalkyl;

$R^6$ a group

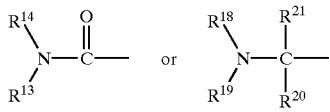

where the molar weight of the groups $R^{13}$ and $R^{14}$ taken together must be at least 60.

$R^{13}$ and $R^{14}$ (which may be identical or different):

hydrogen, $C_1$–$C_5$-alkyl, $C_3$–$C_5$-alkenyl or $C_3$–$C_5$-alkynyl, it being possible for each of these radicals to be substituted one or more times by: halogen, hydroxyl, carboxyl, amino, $C_1$–$C_4$-alkoxy, $C_1$–$C_4$-haloalkoxy, $C_5$–$C_6$-cycloalkyl, NH($C_1$–$C_4$-alkyl), N($C_1$–$C_4$-alkyl)$_2$, phenoxy or phenyl, it being possible for said aryl radicals in turn to be substituted one to three times by halogen, hydroxyl, $C_1$–$C_4$-alkyl, $C_1$–$C_4$-haloalkyl, $C_1$–$C_4$-alkoxy, $C_1$–$C_4$-haloalkoxy, N($C_1$–$C_4$-alkyl)$_2$;

$C_3$–$C_8$-cycloalkyl, it being possible for each of these radicals to be substituted one or more times by: halogen, carboxyl, $C_1$–$C_4$-alkyl, $C_1$–$C_4$-alkoxy, $C_{1-C_4}$-haloalkoxy;

phenyl which can be substituted one to three times by: halogen, carboxyl, hydroxyl, amino, $R^{15}$, $C_1$–$C_4$-alkyl, $C_1$–$C_4$-alkoxy, $C_1$–$C_4$-alkylthio, $C_1$–$C_4$-haloalkyl, $C_1$–$C_4$-alkylcarbonyl, $C_1$–$C_4$-alkoxycarbonyl, $C_1$–$C_4$-haloalkoxy, NH($C_1$–$C_4$-alkyl), N($C_1$–$C_4$-alkyl)$_2$, dioxomethylene [sic], dioxoethylene [sic] or phenyl which can be substituted once to three times by halogen, $C_1$–$C_4$-alkyl, $C_1$–$C_4$-alkoxy or $C_1$–$C_4$-alkylthio;

or $R^{13}$ and $R^{14}$ together form a $C_3$–$C_7$-alkylene chain which is closed to a ring and which may be substituted one or more times by $C_1$–$C_4$-alkyl and in which one alkylene [sic] group can is be replaced by oxygen or sulfur, such as —($CH_2$)$_3$—, —($CH_2$)$_4$—, —($CH_2$)$_5$—, —($CH_2$)$_6$—, —($CH_2$)$_7$—, —($CH_2$)$_2$—O—($CH_2$)$_2$—, —($CH_2$)$_2$—S—($CH_2$)$_2$—;

or $R^{13}$ and $R^{14}$ together form a $C_3$–$C_7$-alkylene chain which is closed to a ring and to which [lacuna] phenyl ring is fused, such as 2,3-dihydroindole, indole, 1,3-dihydroisoindole, 1,2,3,4-tetrahydroquinoline, 1,2,3,4-tetrahydroisoquinoline, it being possible for the phenyl ring in each case to be substituted one to three times by halogen, $C_1$–$C_4$-alkyl, $C_1$–$C_4$-alkoxy, $C_1$–$C_4$-haloalkoxy, hydroxyl, carboxyl.

The groups $R^{13}$ and $R^{14}$ taken together must contain at least 5 carbon atoms.

$R^7$ and $R^8$ (which may be identical or different): hydrogen, $C_1$–$C_4$-alkyl.

$R^{15}$ $C_1$–$C_4$-alkyl, $C_1$–$C_4$-alkoxy, each of which may carry one of the following radicals: hydroxyl, NH($C_1$–$C_4$-alkyl), N($C_1$–$C_4$-alkyl)$_2$, carboxamide [sic] or CON($C_1$–$C_4$-alkyl)$_2$.

$R^{18}$ hydrogen;

$C_1$–$C_4$-alkyl, where each of these radicals can be substituted one to three times by: halogen, $C_1$–$C_4$-alkoxy, $C_1$–$C_4$-alkylthio, $C_3$–$C_8$-cycloalkyl, phenoxy or phenyl, where the abovementioned aryl radicals for their part can be substituted one to three times by: halogen, $C_1$–$C_4$-alkyl or $C_1$–$C_4$-alkoxy;

$C_3$–$C_8$-cycloalkyl;

phenyl which can be substituted one to three times by: halogen, hydroxyl, $R^{15}$, $C_1$–$C_4$-alkyl, $C_1$–$C_4$-alkoxycarbonyl, $C_1$–$C_4$-alkoxy, dioxomethylene [sic], dioxoethylene [sic] or phenyl which can be substituted one to three times by: halogen, $C_1$–$C_4$-alkyl, trifluoromethyl, $C_1$–$C_4$-alkoxy;

$R^{19}$ $C_1$–$C_4$-alkylcarbonyl, where each of these radicals can be substituted one to three times by: halogen, $C_1$–$C_4$-alkoxy, $C_3$–$C_8$-cycloalkyl, phenyl which can be substituted for its part one to three times by: halogen, $C_1$–$C_4$-alkyl or $C_1$–$C_4$-alkoxy;

$C_3$–$C_8$-cycloalkylcarbonyl;

phenylcarbonyl or naphthylcarbonyl, each of which can be substituted by one or more of the following radicals: halogen, $R^{15}$, $C_1$–$C_4$-alkyl, $C_1$–$C_4$-alkoxy, phenoxy, dioxomethylene [sic], dioxoethylene [sic] or phenyl which can be substituted one to three times by: halogen, $C_1$–$C_4$-alkyl or $C_1$–$C_4$-alkoxy;

$C_1$–$C_4$-alkylsulfonyl, where each of these radicals can be substituted one to three times by: halogen, $C_1$–$C_4$-alkoxy, phenyl which for its part can be substituted one to three times by: halogen, $C_1$–$C_4$-alkyl, $C_1$–$C_4$-alkoxy or $C_1$–$C_4$-alkylthio;

$C_3$–$C_8$-cycloalkylsulfonyl;

phenylsulfonyl or naphthylsulfonyl, where each of these radicals can be substituted one to three times by: halogen, $R^{15}$, $C_1$–$C_4$-alkyl, $C_1$–$C_4$-alkoxy, dioxomethylene [sic], dioxoethylene [sic] or phenyl;

$R^{20}$ hydrogen, $C_1$–$C_4$-alkyl.

$R^{21}$ hydrogen, $C_1$–$C_4$-alkyl.

W sulfur or oxygen;

The compounds of the present invention provide a novel therapeutic potential for the treatment of hypertension, pulmonary hypertension, myocardial infarct, angina pectoris, arrhythmia, acute/chronic kidney failure, chronic cardiac insufficiency, renal insufficiency, cerebral vasospasms, cerebral ischemia, subarachnoid hemorrhages, migraine, asthma, atherosclerosis, endotoxic shock, endotoxin-induced organ failure, intravascular coagulation, restenosis after angioplasty and bypass operations, benign prostate hyperplasia, ischemic and intoxication-induced kidney failure or hypertension, metastasis and growth of mesenchymal tumors, contrast agent-induced kidney failure, pancreatitis, gastrointestinal ulcers.

The invention furthermore provides combinations of endothelin receptor antagonists of the formula I and inhibitors of the renin-angiotensin system. Inhibitors of the renin-angiotensin system are renin inhibitors, angiotensin-II antagonists and angiotensin converting enzyme (ACE) inhibitors. Preference is given to combinations of endothelin receptor antagonists of the formula I and ACE inhibitors.

The invention furthermore provides combinations of endothelin receptor antagonists of the formula I and beta blockers.

The invention furthermore provides combinations of endothelin receptor antagonists of the formula I and diuretics.

The invention furthermore provides combinations of endothelin receptor antagonists of the formula I and substances which block the action of VEGF (vascular endothelial growth factor). Such substances are, for example, antibodies directed against VEGF, or specific binding proteins, or else low-molecular-weight substances which are able to specifically inhibit VEGF release or receptor binding.

The abovementioned combinations can be administered simultaneously or sequentially. They can be employed both in a single pharmaceutical formulation or else in separate formulations. The application form can also vary, for example, the endothelin receptor antagonists can be administered orally and the VEGF inhibitors parenterally.

These combination products are particularly suitable for the treatment and prevention of hypertension and its sequelae, and for the treatment of cardiac insufficiency.

The good action of the compounds can be shown in the following experiments: [sic]

The invention furthermore provides a structural fragment of the formula

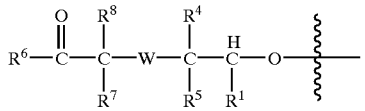

in which the radicals $R^1$, $R^4$, $R^5$, $R^6$, $R^7$, $R^8$ and W are as defined above.

Such structural fragments are suitable as structural components of endothelin receptor antagonists.

The invention furthermore provides endothelin receptor antagonists comprising a structural fragment of the formula

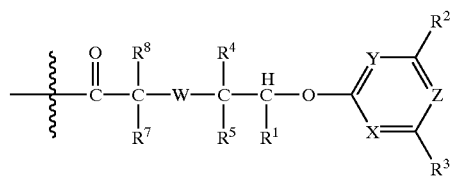

in which the radicals $R^1$, $R^2$, $R^3$, $R^4$, $R^5$, $R^7$, $R^8$, W, X, Y and Z are as defined above, covalently linked to a group which has a molecular weight of at least 30, preferably 40.

The invention furthermore provides endothelin receptor antagonists comprising a structural fragment of the formula

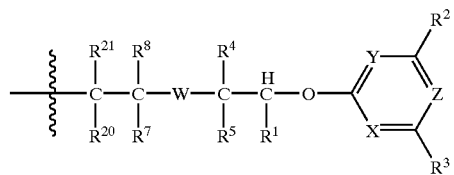

in which the radicals $R^1$, $R^2$, $R^3$, $R^4$, $R^5$, $R^7$, $R^8$, $R^{20}$, $R^{21}$, W, X, Y and Z are as defined in claim 1, covalently linked via a nitrogen atom to a group which has a molecular weight of at least 58.

The invention furthermore provides compounds of the formula Ia

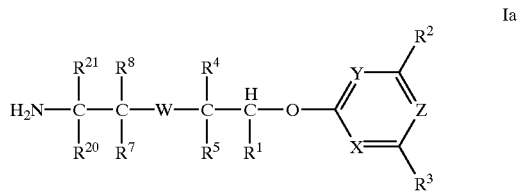

in which the radicals $R^1$, $R^2$, $R^3$, $R^4$, $R^5$, $R^7$, $R^8$, $R^{20}$, $R^{21}$, W, X, Y and Z are as defined in claim 1.

Receptor Binding Studies

Cloned human $ET_A$ or $ET_B$ receptor-expressing CHO cells were employed for binding studies.

Membrane Preparation

The $ET_A$ or $ET_B$ receptor-expressing CHO cells were grown in DmeM NUT MIX $F_{12}$-medium (Gibco, No. 21331-020) with 10% fetal calf serum (PAA Laboratories GmbH, Linz, No. A15-022), 1 mM glutamine (Gibco No. 25030-024), 100 U/ml penicillin and 100 μg/ml streptomycin (Gibco [sic], Sigma No. P-0781). After 48 hours, the cells were washed with PBS and incubated with 0.05% trypsin-containing PBS at 37° C. for 5 minutes. This was followed by neutralization with medium, and the cells were collected by centrifugation at 300×g.

For the membrane preparation, the cells were adjusted to a concentration of $10^8$ cells/ml of buffer (50 mM tris.HCL [sic] buffer, pH 7.4) and then disintegrated by ultrasound Branson Sonifier 250, 40–70 seconds/constant/output [sic] 20).

Binding Assays

For the $ET_A$ and $ET_B$ receptor binding assay, the membranes were suspended in incubation buffer (50 mM tris-HCl, pH 7.4 with 5 mM $MnCl_2$, 40 mg/ml Bacitracin and 0.2% BSA) in a concentration of 50 μg of protein per assay mixture and incubated with 25 pM [125I]-$ET_1$ [sic] ($ET_A$ receptor assay) or 25 pM [125I]-ET$_3$ [sic] (ET$_B$ receptor assay) at 25° C. in the presence and absence of of test substance. The nonspecific binding was determined with $10^{-7}$ M ET$_1$. After 30 min, filtration through GF/B glass fiber filters (Whatman, England) in a Skatron cell harvester (Skatron, Lier, Norway) was carried out to separate free and bound radioligand, and the filters was washed with ice-cold tris-HCl buffer, pH 7.4 with 0.2% BSA. The radioactivity collected on the filters was quantified using a Packard 2200 CA liquid scintillation counter.

In vivo Testing of the ET Antagonists

Male ST rats weighing 250–300 g were anesthetized with amobarbital, artificially ventilated, vagotomized and pithed. The carotid artery and the jugular vein were cathetized [sic].

In control animals, intravenous administration of 1 μg/kg ET1 results in a distinct rise in blood pressure which persists for a lengthy period.

The test animals received i.v. injections of the test compounds (1 ml/kg) 30 min before the ET1 administration. To determine the ET antagonistic properties, the changes in the blood pressure of the test animals were compared with those of the control animals.

Oral Testing of the Mixed ET$_A$ and ET$_B$ Antagonists

Male normotensive rats (Sprague Dawley, Janvier) weighing 250–350 g are pretreated orally with the test substances. 80 minutes later, the animals are anesthetized with urethane and the carotid artery (for measuring the blood pressure) and the jugular vein (administration of big endothelin/endothelin 1) are catheterized.

After a stabilization period, big endothelin (20 μg/kg, administration volume 0.5 ml/kg) or ET1 (0.3 μg/kg, administration volume 0.5 ml/kg) is administered intravenously. The blood pressure and heart rate are recorded continuously for 30 minutes. The distinct and long-lasting changes in blood pressure are calculated as area under the curve (AUC). To determine the antagonistic effect of the test substances, the AUC of the substance-treated animals is compared with the AUC of the control animals.

The compounds according to the invention can be administered orally or parenterally (subcutaneously, intravenously, intramuscularly, intraperitoneally) in a conventional way. Administration can also take place with vapors or sprays through the nasopharyngeal space.

The dosage depends on the age, condition and weight of the patient and on the mode of administration. As a rule, the daily dose of active ingredient is about 0.5–50 mg/kg of bodyweight on oral administration and about 0.1–10 mg/kg of bodyweight on parenteral administration.

The novel compounds can be used in conventional solid or liquid pharmaceutical forms, e.g. as uncoated or (film-) coated tablets, capsules, powders, granules, suppositories, solutions, ointments, creams or sprays. These are produced in a conventional way. The active ingredients can for this purpose be processed with conventional pharmaceutical auxiliaries such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The administration forms obtained in this way normally contain from 0.1 to 90% by weight of active ingredient.

SYNTHESIS EXAMPLES

Example 1

N,N-di-n-Butyl-2-benzyloxyacetamide 3 g of N-methylmorpholine and 4 g of isobutyl chloroformate were successively added dropwise to 5 g of 2-benzyloxyacetic acid in 50 ml of THF at −10° C. The mixture was stirred for 10 minutes and then 5 ml of di-n-butylamine and a further 3 g of N-methylmorpholine were added. After one hour, the mixture was added to 500 ml of water and extracted several times with ether. The collected organic phases were dried over magnesium sulfate and, after removal of the solvent by distillation, 7 g of an oil were isolated and were immediately employed further.

Example 2

N,N-di-n-Butyl-2-hydroxyacetamide 4 g of N,N-di-n-butyl-2-benzyloxyacetamide were dissolved in 50 ml of ethanol, and a spatula tip of Pd/carbon was added. The mixture was stirred under a hydrogen atmosphere for 16 hours, and then the catalyst was filtered off and the solvent was distilled off. 3 g of an oil were isolated and were immediately reacted further.

Example 3

Methyl 2-hydroxy-3-(N,N-di-n-butylcarbamoylmethoxy)-3,3-diphenylpropionate 1.3 g of N,N-di-n-butyl-2-hydroxyacetamide and 1.8 g of methyl 2,3-epoxy-3,3-diphenylpropionate were dissolved in 30 ml of methylene chloride and, while cooling in ice, a catalytic amount of p-toluenesulfonic acid was added. The mixture was stirred at room temperature for 24 hours and then added to sodium bicarbonate solution, the organic phase was separated off and dried over magnesium sulfate, and the solvent was distilled off. The residue was purified by chromatography, and 1.4 g of an oil were isolated and were immediately reacted further.

Example 4

2-Hydroxy-3-(N,N-dibutylcarbamoylmethoxy)-3,3-diphenylpropionic acid 1.42 g of methyl 2-hydroxy-3-(N,N-dibutylcarbamoylmethoxy)-3,3-diphenylpropionate were dissolved in 10 ml of dioxane and 4.8 ml of 1N sodium hydroxide solution and stirred at room temperature for 3 hours. Water was then added to the mixture, and the aqueous phase was extracted with ether. The aqueous phase was acidified with hydrochloric acid and extracted with ethyl acetate, and the organic phase was dried over magnesium sulfate. After removal of the solvent by distillation, 1.1 g of oil were isolated and were immediately employed further.

Example 5

2-(4,6-Dimethyl-2-pyrimidinyloxy)-3-(N,N-dibutylcarbamoylmethoxy)-3,3-diphenylpropionic acid (I-347)

560 mg of 2-hydroxy-3-(N,N-dibutylcarbamoylmethoxy)-3,3-diphenylpropionic acid were introduced into THF, and 63 mg of lithium amide and, 10 minutes later, 256 mg of 2-methylsulfone-4,6-dimethylpyrimidine [sic] were added. The mixture was stirred at 50° C. for 5 hours and then water was added. The aqueous phase was acidified with citric acid and extracted with ethyl acetate. The organic phase was dried, the solvent was distilled off, and the residue was purified by chromatography. The isolated product was crystallized from ether/n-hexane.

$^1$H-NMR (200 MHz): 7.30–7.20 ppm (10 H, m), 6.75 (1 H, s), 6.15 (1 H, s), 4.50 (1 H, d), 4.20 (1 H, d), 3.30 (2 H, dd), 2.95 (2 H, dd) 2.35 (6 H, s), 1.55–1.00 (8 H, m), 0.95 (3 H, tr), 0.80 (3 H, tr).

ESI-MS: M$^+$=533

Example 6

N-Propyl-N-(2-hydroxyethyl)benzenesulfonamide

At 0° C., 5.16 g (50 mmol) of N-propylethanolamine were introduced into 70 ml of methylene chloride, and 9.7 g (55 mmol) of benzenesulfonyl chloride and 7.6 g (75 mmol) of triethylamine were added successively. After 2 hours of stirring at 0° C., the mixture was allowed to warm to room temperature, stirring was continued for a further hour and the mixture was then extracted with 1M hydrochloric acid and subsequently with 2M aqueous sodium hydroxide solution. The organic phase was dried over Na$_2$SO$_4$, filtered, concentrated and the resulting residue (13.2 g) was chromatographed over silica gel (methylene chloride/methanol 19:1). Yield: 7.4 g as an oil which was directly reacted further.

Example 7

Methyl 2-hydroxy-3-(2-(N-propyl-N-benzenesulfonylamino)ethoxy)-3,3-diphenylpropionate 7.3 g (30 mmol) of N-propyl-N-(2-hydroxyethyl) benzenesulfonamide and 7.6 g (30 mmol) of methyl 2,3-epoxy-3,3-diphenylpropionate were dissolved in 40 ml of methylene chloride and, with ice-cooling, 0.57 g (3 mmol) of p-toluenesulfonic acid was added. The reaction mixture was stirred at room temperature for 24 hours and then diluted with methylene chloride and extracted with 2M aqueous sodium hydroxide solution, the organic phase was separated off and dried over sodium sulfate and the solvent was distilled off. The residue (12.0 g of an oil) was directly reacted further.

Example 8

2-Hydroxy-3-(2-(N-propyl-N-benzenesulfonylamino)ethoxy)-3,3-diphenylpropionic acid 6.0 g of methyl 2-hydroxy-3-(2-(N-propoyl-N-benzenesulfonylamino)ethoxy)-3,3-diphenylpropionate [sic] (from Example 7) were dissolved in 70 ml of dioxane and mixed with 36 ml of 1M KOH and stirred at room temperature overnight. The reaction mixture was subsequently mixed with water and the aqueous phase was extracted with ether. The aqueous phase was acidified with hydrochloric acid and extracted with ether, the organic phase was dried over sodium sulfate and the solvent was distilled off. The residue (3.3 g) was chromatographed over silica gel (methylene chloride/methanol 9:1), giving 2.6 g of product.

m.p.: 144–146° C. (from ether)

Example 9

2-(4-Methyl-6-methoxypyrimidin-2-yloxy)-3-(2-(N-propyl-N-benzenesulfonylamino)ethoxy)-3,3-diphenylpropionic acid (II-2)

135 mg (5.6 mmol) of lithium amide (95%) were suspended in 5 ml of dimethylformamide, cooled to 0° C., admixed with 0.9 g (1.9 mmol) of 2-hydroxy-3-(2-(N-propoyl-N-benzenesulfonylamino)ethoxy)-3,3-diphenylpropionic [sic] acid, dissolved in 4 ml of dimethylformamide and stirred at 0° C. for 30 min. 0.56 g (2.8 mmol) of 2-methylsulfone-4-methyl-6-methoxypyrimidine [sic] were then added and the mixture was stirred at room temperature overnight and then mixed with water. The aqueous phase was extracted with ether, the resulting organic phase was discarded and the aqueous phase was adjusted to pH 1 using hydrochloric acid and extracted with ether. The organic phase was dried over sodium sulfate, the solvent was distilled off and the residue (1.26 g) was triturated in ether/heptane. Yield: 0.9 g of a white solid.

ESI-MS: 606 (M+H)$^+$ $^1$H-NMR (270 MHz, CDCl$_3$): 7.70–7.85 ppm (2 H, m); 7.20–7.55 (13 H, m); 6.25 (1 H, s); 6.15 (1 H, s); 3.9 (3 H, s); 3.50–3.75 (2 H, m); 3.20–3.50 (2 H, m); 3.00–3.15 (2 H, m); 2.30 (3 H, s); 1.35–1.55 (2 H, m); 0.75 (3 H, tr).

Example 10

Methyl 2-hydroxy-3-(2-benzyloxycarbonylaminoethoxy)-3,3-diphenylpropionate 9.8 g (50 mmol) of benzyl (2-hydroxyethyl)carbamate and 12.7 g (50 mmol) of methyl 2,3-epoxy-3,3-diphenylpropionate were dissolved in 80 ml of methylene chloride and, with ice-cooling, 0.95 g (5 mmol) of p-toluenesulfonic acid was added. The reaction mixture was stirred at room temperature for 24 hours and then diluted with methylene chloride and extracted with 2M aqueous sodium hydroxide solution, the organic phase was separated off and dried over sodium sulfate and the solvent was distilled off. The residue (22.2 g of an oil) was directly reacted further.

Example 11

2-Hydroxy-3-(2-benzyloxycarbonylaminoethoxy)-3,3-diphenylpropionic acid 22.2 g of methyl 2-hydroxy-3-(2-benzyloxycarbonylaminoethoxy)-3,3-diphenylpropionate (from Example 10) were dissolved in 300 ml of dioxane, mixed with 148 ml of 1M KOH and stirred at room temperature overnight. The reaction mixture was subsequently mixed with water and the aqueous phase was extracted with ether. The aqueous phase was acidified with hydrochloric acid and extracted with ether, the organic phase was dried over sodium sulfate and the solvent was distilled off. The residue (17.5 g) was directly used further.

Example 12

2-(4,6-Dimethylpyrimidin-2-yloxy)-3-(2-benzyloxycarbonylaminoethoxy)-3,3-diphenylpropionic acid (II-32)

2.5 g (103 mmol) of lithium amide (95%) were suspended in 60 ml of dimethylformamide, cooled to 0° C., admixed with 15 g (34.4 mmol) of 2-hydroxy-3-(2-benzyloxycarbonylaminoethoxy)-3,3-diphenylpropionic acid, dissolved in 60 ml of dimethylformamide, and stirred at 0° C. for 30 min. 8.34 g (44.7 mmol) of 2-methylsulfone-4-methyl-6-methoxypyrimidine [sic] in 30 ml of dimethylformamide were then added and the mixture was stirred at room temperature for 3 days and then mixed with water. The aqueous phase was extracted with ether, the resulting organic phase was discarded and the aqueous phase was then adjusted to pH 1 using hydrochloric acid and extracted with ether. The organic phase was dried over sodium sulfate, the solvent was distilled off and the residue was chromatographed over silica gel (methylene chloride/methanol 9:1). Yield: 14.0 g of a white foam.

$^1$H-NMR (270 MHz, DMSO): 12.0–13.0 ppm (1H, brd); 7.10–7.45 (16 H, m); 6.95 (1 H, s); 6.20 (1 H, s); 5.0 (2 H, s); 3.80–3.95 (2 H, m); 3.55–3.70 (2 H, m); 3.20–3.40 (2 H, m); 2.30 (6 H, s).

Example 13

2-(4,6-Dimethylpyrimidin-2-yloxy)-3-(2-aminoethoxy)-3,3-diphenylpropionic acid

A solution of 13.1 g (24.2 mmol) of 2-(4,6-dimethylpyrimidin-2-yloxy)-3-(2-benzyloxycarbonylaminoethoxy)-3,3-diphenylpropionic acid in 200 ml of methanol was hydrogenated with hydrogen overnight, under atmospheric pressure and at room temperature, using 800 mg of palladium on activated carbon (10%). The reaction mixture was diluted with methanol to dissolve precipitated product, filtered and concentrated. Yield: 9.6 g of a white solid.

$^1$H-NMR (270 MHz, DMSO): 7.10–7.40 ppm (10 H, m); 6.90 (1 H, s); 6.00 (1 H, s); 3.60–3.75 (2 H, m); 2.90–3.00 (2 H, m); 2.25 (6 H, s).

Example 14

2-(4,6-Dimethylpyrimidin-2-yloxy)-3-(2-(3,4-dimethoxybenzoyl-amino)ethoxy)-3,3-diphenylpropionic acid (II-62)

A solution of 1.0 g (2.5 mmol) of 2-(4,6-dimethylpyrimidin-2-yloxy)-3-(2-aminoethoxy)-3,3-diphenylpropionic acid in 10 ml of methylene chloride was successively admixed at room temperature with 0.35 g (2.7 mmol) of N-ethyldiisopropylamine, 0.03 g (0.2 mmol) of dimethylaminopyridine and 0.54 g (2.7 mmol) of 3,4-dimethoxybenzoyl chloride. The mixture was stirred at room temperature for 4 days and then diluted with diethyl ether and extracted with 1M hydrochloric acid and 1M aqueous sodium hydroxide solution, and the combined alkaline phases were made acidic and extracted with ether. The organic phase was dried over sodium sulfate, the solvent was distilled off and the residue (0.9 g) was chromatographed over silica gel (methylene chloride/methanol 9:1). Yield: 280 mg of a white foam.

ESI-MS: 571 (M+H)$^+$ $^1$H-NMR (360 MHz, DMSO): 7.10–7.55 ppm (12 H, m); 7.00 (1 H, d); 6.90 (1 H, s); 6.20 (1 H, s); 3.65–4.00 (2 H, m); 3.80 (3 H, s); 3.75 (3 H, s); 3.45–3.55 (2 H, m); 2.30 (6 H, s).

Example 15

Benzyl (S)-5,5-diphenyl-2-oxo-1,4-dioxane-6-carboxylate 38 g (100 mmol) of the benzyl (S)-2-hydroxy-3-methoxy-3,3-diphenylpropionate were added to 9.8 g (130 mmol) of glycolic acid, and the mixture was stirred with 300 mg of anhydrous para-toluenesulfonic acid at 70° C. on a rotary evaporator under reduced pressure for 20 minutes. The content of the flask was taken up in dichloromethane, the acid was separated off using sodium hydrogen sulfate solution, the organic phase was separated off and dried and the solvent was distilled off. The residue was recrystallized from ether, and 21 g (54 mmol) of product were isolated.

$[\alpha]_D$=+283° at 20° C. in ethanol

Example 16

(S)-(1,1-Diphenyl-2-hydroxy-2-benzyloxycarbonylethoxy)acetic acid 14 g (36 mmol) of benzyl (S)-5,5-diphenyl-2-oxo-1,4-dioxane-6-carboxylate were dissolved in 50 ml of DMF and, with ice-cooling, 43 ml of 1 N NaOH solution were added. After ten minutes, the mixture was diluted with 300 ml of water and neutralized with 43 ml of 1 N hydrochloric acid and the aqueous phase was extracted with ether. The ether phase was dried, the solvent was distilled off and the residue (8.8 g, 21 mmol of an oil) was directly reacted further.

Example 17

(S)-(1,1-Diphenyl-2-(4,6-dimethylpyrimidin-2-yloxy)-2-benzyloxycarbonylethoxy)acetic acid 6.6 g (15 mmol) of (S)-(1,1-diphenyl-2-hydroxy-2-benzyloxycarbonylethoxy)acetic acid were introduced into 75 ml of DMF, and 1.4 g of NaH (30 mmol, 50% suspension) were added a little at a time with ice-cooling. 3.6 g (19.5 mmol) of 4,6-dimethyl-2-methylsulfonepyrimidine [sic] were subsequently added and the mixture was stirred for a quarter of an hour and then warmed to room temperature. After 45 minutes, the reaction was complete and the reaction solution was poured into 500 ml of ice-water. The aqueous phase was extracted with ethyl acetate, the combined organic phases were dried and the solvent was distilled off. The oily residue was stirred with ether/hexane, and 6.4 g of crystals could be isolated.

Example 18

Benzyl (S)-2-(4,6-dimethylpyrimidin-2-yloxy)-3-(N-methyl-N-(3-methylphenyl)carbamoylmethoxy-3,3-diphenylpropionate [sic]

Under protective gas and at −10° C., 512 mg (1 mmol) of S-(1,1-diphenyl-2-(4,6-dimethylpyrimidin-2-yloxy)-2-benzyloxycarbonylethoxy)acetic acid were dissolved in 20 ml of dichloromethane, and 121 mg (1 mmol) of N-(3-methylphenyl)-N-methylamine, 92 ml (1 mmol) of ethyldiisopropylamine and 191 mg (1 mmol) of N-(3-dimethylaminopropyl)-N-ethylcarbodiimide were added successively. After one hour, the reaction mixture was warmed to room temperature and stirred for a further 16 hours. The mixture was subsequently diluted with dichloromethane to 100 ml and washed with citric acid and water. The organic phase was dried and the solvent was distilled off. For further purification, the residue was subjected to flash chromatography (ethyl acetate/cyclohexane 1/1), and 290 mg of product were isolated and were immediately employed further.

Example 19

(S)-2-(4,6-Dimethylpyrimidin-2-yloxy)-3-(N-methyl-N-(3-methylphenyl)carbamoylmethoxy)-3,3-diphenylpropionic acid 260 mg of benzyl (S)-2-(4,6-dimethylpyrimidin-2-yloxy)-3-(N-methyl-N-(3-methylphenyl)carbamoylmethoxy)-3,3-diphenylpropionate were dissolved in 50 ml of ethyl acetate in ethyl acetate [sic], and a spatula tip of Pd/C was added. The mixture was stirred under an atmosphere of hydrogen for 2 hours. The Pd/C was subsequently filtered off and the ethyl acetate was distilled off. The residue was stirred with ether/hexane, and 127 mg of crystals could be isolated.

$[\alpha]_D$=+90° at 20° C. in ethanol $^1$H-NMR (200 MHz): 7.40–7.00 ppm (14 H, m), 6.75 (1 H, s), 6.05 (1 H, s), 4.15 (1 H, d), 3.75 (1 H, d), 3.25 (3 H, s), 2.40 (6 H, s), 2.20 (3 H, s).

ESI-MS: M$^+$=525

The following compounds were prepared in a similar way to the examples mentioned above.

Example 20

2-(4-Methyl-6-methoxy-2-pyrimidinyloxy)-3-(N,N-dibutylcarbamoylmethoxy)-3,3-diphenylpropionic acid (I-349)

$^1$H-NMR (200 MHz): 7.30–7.20 ppm (10 H, m), 6.25 (1 H, s), 6.00 (1 H, s), 4.50 (1 H, d), 4.25 (1 H, d), 3.95 (3 H, s), 3.30 (2 H, dd), 2.95 (2 H, dd), 2.25 (3 H, s), 1.55–1.00 (8 H, m), 0.95 (3 H, tr), 0.80 (3 H, tr).

ESI-MS: M$^+$=549

Example 21

2-(4,6-Dimethyl-2-pyrimidinyloxy)-3-(N-methyl-N-phenylcarbamoylmethoxy)-3,3-diphenylpropionic acid (I-109)

ESI-MS: M$^+$=511

$^1$H-NMR (200 MHz): 7.40–7.20 ppm (15 H, m), 6.80 (1 H, s), 6.15 (1 H, s), 4.15 (1 H, d), 3.8 (1 H, d), 3.30 (3 H, s), 2.35 (6 H, s).

Example 22

2-(4-methyl-6-methoxy-2-pyrimidinyloxy)-3-(N-methyl-N-phenylcarbamoylmethoxy)-3,3-diphenylpropionic acid (I-111)

$^1$H-NMR (200 MHz): 7.40–7.20 ppm (15 H, m), 6.30 (1 H, s), 6.00 (1 H, s), 4.20 (1 H, d), 3.80 (3 H, s), 3.75 (1 H, d), 3.25 (3 H, s), 2.30 (3 H, s).

ESI-MS: M$^+$=527

Example 23

2-(4,6-Dimethyl-2-pyrimidinyloxy)-3-(2-oxo-2-(1,2,3,4-tetrahydroisoquinolin-2-yl)ethoxy)-3,3-diphenylpropionic acid (I-307)

$^1$H-NMR (200 MHz): 7.40–7.10 ppm (14 H, m), 6.60 (1 H, s), 6.05 (1 H, s), 4.75–4.25 (4 H, m), 3.85 (1 H, m), 3.50–3.25 (1 H, m), 3.00–2.75 (2 H, m), 2.25 (3 H, s), 2.10 (3 H, s).

ESI-MS: M$^+$=537

Example 24

2-(4-Methyl-6-methoxy-2-pyrimidinyloxy)-3-(2-oxo-2-(1,2,3,4-tetrahydroisoquinolin-2-yl)ethoxy)-3,3-diphenylpropionic acid (I-309)

$^1$H-NMR (200 MHz): 7.40–7.10 ppm (14 H, m), 6.20 (1 H, s), 6.00 (1 H, s), 4.75–4.25 (4 H, m), 3.85 (1 H, m), 3.75 (3 H, s), 3.40 (1 H, m), 3.00–2.75 (2 H, m), 2.10 (3 H, s).

ESI-MS: M$^+$=553

Example 25

2-(4,6-Dimethyl-2-pyrimidinyloxy)-3-(N-ethoxymethylene-N-(2,6-diethylphenyl)carbamoylmethoxy)-3,3-diphenylpropionic [sic] acid (I-325)

$^1$H-NMR (200 MHz): 7.40–7.10 ppm (13 H, m), 6.75 (1 H, s), 6.15 (1 H, s), 5.10 (1 H, d), 4.90 (1 H, d), 4.00–3.70 (4 H, m), 2.70–2.30 (4 H, m), 2.40 (6 H, s), 1.25 (6 H, m), 1.10 (3 H, tr).

ESI-MS: M$^+$=611.

Example 26

2-(4,6-Dimethyl-2-pyrimidinyloxy)-3-(N-isopropyl-N-phenylcarbamoylmethoxy)-3,3-diphenylpropionic acid (I-271)

$^1$H-NMR (200 MHz): 7.30–7.10 ppm (15 H, m), 6.70 (1 H, s), 6.10 (1 H, s), 5.10 (1 H, m), 4.00 (1 H, d), 3.60 (1 H, d), 2.30 (6 H, 1), 1.10 (6 H, m).

ESI-MS: M$^+$=539.

Example 27

2-(4,6-Dimethyl-2-pyrimidinyloxy)-3-(N-methoxymethylene-N-(2,6-diisopropylphenyl)carbamoylmethoxy)-3,3-diphenylpropionic [sic] acid (I-334)

$^1$H-NMR (200 MHz): 7.40–7.10 ppm (13 H, m), 6.75 (1 H, s), 6.15 (1 H, s), 5.10 (1 H, d), 4.90 (1 H, d), 4.5.7 (1 H, d), 3.75 (1 H, d), 3.50 (3 H, s), 3.30 (1 H, m), 2.9 (1 H, m), 2.30 (6 H, s), 1.20 (9 H, m), 0.6 (3 H, d).

ESI-MS: M$^+$=625.

Example 28

2-(4,6-Dimethylpyrimidin-2-yloxy)-3-(2-(N-propyl-N-benzenesulfonylamino)ethoxy)-3,3-diphenylpropionic acid (II-48)

ESI-MS: 590 (M+H)$^+$ $^1$H-NMR (270 MHz, CDCl$_3$): 7.75–7.85 ppm (2 H, m); 7.20–7.55 (13 H, m); 6.70 (1 H, s); 6.25 (1 H, s); 3.55–3.75 (2 H, m); 3.20–3.50 (2 H, m); 3.00–3.15 (2 H, m); 2.35 (6 H, S); 1.35–1.50 (2 H, m); 0.75 (3 H, tr).

Example 29

2-(4,6-Dimethylpyrimidin-2-yloxy)-3-(2-(N-butyl-N-benzenesulfonylamino)ethoxy)-3,3-diphenylpropionic acid (II-20)

ESI-MS: 604 (M+H)$^+$ $^1$H-NMR (200 MHz, CDCl$_3$): 7.75–7.85 ppm (2 H, m); 7.20–7.55 (13 H, m); 6.70 (1 H, s); 6.20 (1 H, s); 3.20–3.75 (4 H, m); 3.00–3.15 (2 H, m); 2.35 (6 H, s); 1.35–1.50 (2 H, m); 1.10–1.30 (2 H, m); 0.75 (3 H, tr).

Example 30

2-(4,6-Dimethylpyrimidin-2-yloxy)-3-(N-(4-methoxyphenyl)carbamoylmethoxy)-3,3-diphenylpropionic acid (I-37)

$^1$H-NMR (200 MHz, DMSO): 9.75 ppm (NH), 7.50–7.10 (12 H, m), 6.90 (1 H, s), 6.80 (2 H, d), 6.10 (1 H, s), 4.25 (1 H, d), 4.10 (1 H, d), 3.75 (3 H, s), 2.25 (6 H, s).

ESI-MS: M$^+$=527

Example 31

2-(4,6-Dimethylpyrimidin-2-yloxy)-3-(N-phenylcarbamoylmethoxy)-3,3-diphenylpropionic acid (I-19)

$^1$H-NMR (200 MHz, DMSO): 9.90 ppm (NH), 7.70–7.20 (14 H, m), 7.10 (1 H, tr), 6.80 (1 H, s), 6.20 (1 H, s), 4.30 (1 H, d), 4.20 (1 H, d), 2.30 (6 H, s).

ESI-MS: M$^+$=497

Example 32

2-(4,6-Dimethylpyrimidin-2-yloxy)-3-(N-(4-methylphenyl)carbamoylmethoxy)-3,3-diphenylpropionic acid (I-28)

$^1$H-NMR (200 MHz, DMSO): 9.80 ppm (NH), 7.50–7.20 (12 H, m), 7.10 (2 H, d), 6.80 (1 H, s), 6.10 (1 H, s), 4.25 (1 H, d), 4.05 (1 H, d), 2.30 (6 H, s), 2.20 (3 H, s).

ESI-MS: M$^+$=511

Example 33

2-(4,6-Dimethylpyrimidin-2-yloxy)-3-(N-butyl-N-phenylcarbamoylmethoxy)-3,3-diphenylpropionic acid (I-190)

¹H-NMR (200 MHz): 7.25–7.10 ppm (15 H, m), 6.70 (1 H, s), 6.10 (1 H, s), 4.20 (1 H, d), 3.7 (2 H, m), 2.25 (6 H, s), 1.5–1.1 (4 h, m), 0.8 (3 H, tr).

ESI-MS: M$^+$=553

Example 34

2-(4,6-Dimethylpyrimidin-2-yloxy)-3-(2-oxo-2-(6,7-dimethoxy-1,2,3,4-tetrahydroisoquinolin-2-yl)ethoxy)-3,3-diphenylpropionic acid

ESI-MS: M$^+$=597 m.p.: 145–148° C.

Example 35

2-(4,6-Dimethylpyrimidin-2-yloxy)-3-(2-oxo-2-(4,4-dimethyl-1,2,3,4-tetrahydroisoquinolin-2-yl)ethoxy)-3,3-diphenylpropionic acid

ESI-MS: M$^+$=565 m.p.: 185–187° C.

Example 36

(S)-2-(4,6-Dimethylpyrimidin-2-yloxy)-3-(N-(3-methylphenyl)carbamoylmethoxy)-3,3-diphenylpropionic acid ¹H-NMR (200 MHz): 9.10 ppm (NH), 7.50–7.25 (12 H, m), 7.10 (1 H, tr), 6.80 (1 H, d), 6.60 (1 H, s), 6.20 (1 H, s), 4.10 (1 H, d), 3.80 (1 H, d), 2.30 (6 H, s), 2.25 (3 H, s).

ESI-MS: M$^+$=511

Example 37

2-(4,6-Dimethylpyrimidin-2-yloxy)-3-(N-methyl-N-(2-naphth-2-yl-ethyl)carbamoylmethoxy)-3,3-diphenylpropionic acid ¹H-NMR (200 MHz): 8.20 ppm (1 H, m), 7.90–7.70 (3 H, m), 7.50–7.15 (14 H, m), 6.60/6.65 (1 H, s, rotamers), 6.20/6.15 (1 H, s, rotamers), 4.50 (1 H, d, rotamers), 4.25 (1 H, d, rotamers), 3.9 (1 H, m), 3.50–3.20 (3 H, m), 3.05/2.70 (3 H, s, rotamers) 2.30/2.25 (6 H, s, rotamers).

ESI-MS: M$^+$=589

Example 38

2-(4,6-Dimethylpyrimidin-2-yloxy)-3-(N-methyl-N-(2-(4-methoxyphenyl)butyl)carbamoylmethoxy)-3,3-diphenylpropionic acid ¹H-NMR (200 MHz): 7.50–7.05 (12 H, m), 6.95–6.60 (3 H, m), 6.05 (1 H, s, rotamers), 4.50–4.00 (2 H, m, rotamers), 3.75 (3 H, d, rotamers), 3.2–2.8 (3 H, m, rotamers), 2.9 (3 H, s, rotamers), 2.30 (6 H, s, rotamers), 1.70–1.50 (2 H, m), 0.70–0.60 (3 H, m, rotamers).

ESI-MS: M$^+$=597

Example 39

2-(4,6-Dimethylpyrimidin-2-yloxy)-3-(N-methyl-N-(2-isopropyl-2-(3,4-dimethoxyphenyl)-3-methylbutyl)carbamoylmethoxy)-3,3-diphenylpropionic acid ¹H-NMR (200 MHz): 7.30–7.20 (10 H, m), 6.95–6.60 (4 H, m), 6.20 (1 H, s), 4.40 (2 H, m), 4.05 (1 H, d) 3.85 (7 H, m), 2.5 (3 H, s), 2.3 (6 H, s), 2.30–2.20 (2 H, m), 1.00–0.70 (12 H).

ESI-MS: M$^+$=683

Example 40

(S)-2-(4,6-Dimethylpyrimidin-2-yloxy)-3-(N-methyl-N-benzylcarbamoylmethoxy)-3,3-diphenylpropionic acid ¹H-NMR (200 MHz): 7.30–7.10 ppm (15 H, m), 6.75 (1 H, s), 6.20 (1 H, s), 4.75–4.20 (4 H, m, rotamers), 3.00/2.60 (3 H, s, rotamers), 2.35/2.30 (6 H, s, rotamers).

ESI-MS: M$^+$=525

Example 41

2-(4,6-Dimethylpyrimidin-2-yloxy)-3-(N-(2,6-diethylphenyl)carbamoylmethoxy)-3,3-diphenylpropionic acid (I-82)

¹H-NMR (200 MHz): 8.30 ppm (NH), 7.50–7.00 (13 H, m), 6.75 (1 H, s), 6.25 (1 H, s), 4.25 (1 H, d), 3.90 (1 H, d), 2.60 (4 H, q), 2.30 (6 H, s), 1.20 (6 H, tr).

ESI-MS: M$^+$=533

Example 42

2-(4,6-Dimethylpyrimidin-2-yloxy)-3-(N-(4-chlorophenyl)carbamoylmethoxy)-3,3-diphenylpropionic acid (I-46)

¹H-NMR (200 MHz): 10.00 ppm (NH), 7.70 (2 H, d), 7.50–7.10 (12 H, m), 6.75 (1 H, s), 6.20 (1 H, s), 4.20 (1 H, d), 3.80 (1 H, d), 2.30 (6 H, s).

ESI-MS: M$^+$=531

Example 43

2-(4,6-Diethylpyrimidin-2-yloxy)-3-(N-methyl-N-phenylcarbamoylmethoxy)-3,3-diphenylpropionic acid ¹H-NMR (200 MHz): 7.50–7.10 ppm (15 H, m), 6.80 (1 H, s), 6.10 (1 H, S), 4.20 (1 H, d), 3.30 (1 H, s), 2.70 (4 H, q), 1.20 (6 H, tr).

ESI-MS: M$^+$=539

Example 44

2-(4,6-Dimethylpyrimidin-2-yloxy)-3-(N-(3-methoxyphenyl)carbamoylmethoxy)-3,3-diphenyl propionic acid ¹H-NMR (200 MHz): 9.80 ppm (NH), 7.50–7.10 (13 H, m), 6.75 (1 H, s), 6.60 (1 H, dtr), 6.20 (1 H, s), 4.10 (1 H, d), 3.80 (1 H, d), 3.75 (3 H, s), 2.30 (6 H, s).

ESI-MS: M$^+$=527

Example 45

(S)-2-(4,6-Dimethylpyrimidin-2-yloxy)-3-(N-benzylcarbamoylmethoxy)-3,3-diphenylpropionic acid ¹H-NMR (200 MHz): 7.50–7.10 ppm (15 H, m), 6.75 (1 H, s), 6.20 (1 H, S), 4.45 (1 H, dd), 4.40 (1 H, dd), 4.10 (1 H, d), 3.90 (1 H, d), 2.40 (6 H, s).

ESI-MS: M$^+$=511

Example 46

(S)-2-(4,6-Dimethylpyrimidin-2-yloxy)-3-(N-methyl-N-(4-methoxybenzyl)carbamoylmethoxy)-3,3-diphenylpropionic acid ¹H-NMR (200 MHz): 7.50–7.10 (13 H, m), 6.75 (3 H, m, rotamers), 6.20 (1 H, s, rotamers), 4.70–4.00 (4 H, m, rotamers), 3.75 (3 H, s), 3.00/2.70 (3 H, s, rotamers), 2.40/2.35 (6 H, s, rotamers).
ESI-MS: M⁺=555

Example 47

(S)-2-(4,6-Dimethylpyrimidin-2-yloxy)-3-(N-ethyl-N-benzylcarbamoylmethoxy)-3,3-diphenylpropionic acid ¹H-NMR (200 MHz): 7.50–7.20 ppm (15 H, m), 6.70 (1 H, s), 6.20 (1 H, s, rotamers), 4.75–4.10 (4 H, m, rotamers), 3.70/3.30/3.00 (2 H, m, rotamers), 2.35/2.30 (6 H, s, rotamers), 1.10/1.00 (3 H, tr, rotamers).
ESI-MS: M⁺=539

Example 48

(S)-2-(4,6-Dimethylpyrimidin-2-yloxy)-3-(N-methyl-N-(2,6-dichlorobenzyl)carbamoylmethoxy)-3,3-diphenylpropionic acid ESI-MS: M⁺=593
m.p.: 105–110° C.

Example 49

2-(4,6-Dimethylpyrimidin-2-yloxy)-3-(N-methyl-N-(2-phenylethyl)carbamoylmethoxy)-3,3-diphenylpropionic acid ¹H-NMR (200 MHz): 7.50–7.20 ppm (14 H, m), 6.75 (1 H, m), 6.70 (1 H, s, rotamers), 6.15/6.10 (1 H, s, rotamers), 4.50–4.00 (2 H, d, rotamers), 3.70 (1 H, m), 3.50 (1 H, m), 3.20/2.70 (5 H, m, rotamers), 2.35/2.30 (6 H, s, rotamers).
ESI-MS: M⁺=539

Example 50

2-(4,6-Dimethylpyrimidin-2-yloxy)-3-(N-methyl-N-(2-(3,4-dimethoxyphenyl)ethyl)carbamoylmethoxy)-3,3-diphenylpropionic acid ¹H-NMR (200 MHz): 7.50–7.25 ppm (10 H, m), 6.80–6.70 (3 H, m), 6.35 (1 H, m), 4.50–4.00 (2 H, m, rotamers), 3.75 (3 H, s, rotamers), 3.50–2.70 (5 H, m, rotamers), 2.30/2.25 (6 H, s, rotamers).
ESI-MS: M⁺=599

Example 51

2-(4,6-Dimethylpyrimidin-2-yloxy)-3-(2-(3,4-dimethoxybenzoyl-N-methylamino)ethoxy)-3,3-diphenylpropionic acid (II-78)

¹H-NMR (200 MHz): 7.30–7.00 ppm (10 H, m), 7.00–6.80 (3 H, m), 6.60 (1 H, s), 6.20 (1 H, s), 3.90 (6 H, s), 3.90–3.50 (4 H, m), 3.10 (3 H, s), 2.30 (6 H, s).
ESI-MS: M⁺=585

Example 52

2-(4,6-Dimethylpyrimidin-2-yloxy)-3-(2-(2,6-dimethoxybenzoyl-N-methylamino)ethoxy)-3,3-diphenylpropionic acid (II-88)

¹H-NMR (200 MHz): 7.50–7.00 ppm (10 H, m), 6.70–6.40 (4 H, m), 6.30/6.20 (1 H, s, rotamers), 4.10–3.30 (4 H, m), 3.80/3.75/3.65/3.60 (6 H, s, rotamers), 3.10/2.80 (3 H, s), 2.35/2.30 (6 H, s).
ESI-MS: M⁺=585

Example 53

2-(4,6-Dimethylpyrimidin-2-yloxy)-3-(2-(3,4-dichlorobenzoyl-amino)ethoxy)-3,3-diphenylpropionic acid (II-115)

ESI-MS: 580 (M+H)⁺
¹H-NMR (270 MHz, DMSO): 12.0–13.0 ppm (1 H, brd); 8.80 (1 H, t); 7.15–7.65 (13 H, m); 6.95 (1 H, s); 6.20 (1 H, s); 3.85 (1 H, m); 3.65–3.80 (1 H, m); 3.45–3.60 (2 H, m); 2.30 (6 H, s).

Example 54

2-(4,6-Dimethylpyrimidin-2-yloxy)-3-(2-(2,6-dimethoxybenzoyl-amino)ethoxy)-3,3-diphenylpropionic acid (II-122)

ESI-MS: 572 (M+H)⁺
¹H-NMR (270 MHz, CDCl₃): 7.45–7.55 ppm (2 H, m); 7.20–7.40 (10 H, m); 6.65 (1 H, s); 6.55 (1 H, d); 6.35 (1 H, t); 6.25 (1 H, s); 3.60–3.90 (4 H, m); 3.80 (6 H, s); 2.35 (6 H, s).

Example 55

2-(4,6-Dimethylpyrimidin-2-yloxy)-3-(2-(2,4,6-trimethylbenzoyl-amino)ethoxy)-3,3-diphenylpropionic acid (II-169)

ESI-MS: 554 (M+H)⁺
¹H-NMR (270 MHz, CDCl₃): 7.15–7.55 ppm (10 H, m); 6.90 (1 H, s); 6.80 (1 H, s); 6.70 (1 H, s); 6.60 (1 H, tr); 6.25 (1 H, s); 3.60–3.80 (2 H, m); 2.30 (6 H, s); 2.20 (6 H, s); 2.15 (3 H, s).

Example 56

2-(4,6-Dimethylpyrimidin-2-yloxy)-3-(2-(2,3-dimethylbenzoyl-amino)ethoxy)-3,3-diphenylpropionic acid (II-190)

ESI-MS: 540 (M+H)⁺
¹H-NMR (200 MHz, DMSO): 8.30 ppm (1 H, t); 7.10–7.55 (13 H, m); 6.95 (1 H, s); 6.15 (1 H, s); 3.85–4.00 (1 H, m); 3.65–3.80 (1 H, m); 3.45–3.60 (2 H, m); 2.35 (6 H, s); 2.30 (3 H, s); 2.25 (3 H, s).

Example 57

2-(4,6-Dimethylpyrimidin-2-yloxy)-3-(2-(3,5-dichlorobenzoyl-amino)ethoxy)-3,3-diphenylpropionic acid (II-205)

ESI-MS: 580 (M+H)⁺
¹H-NMR (200 MHz, DMSO): 12.4–13.0 ppm (1 H, brd); 8.80 (1 H, tr); 7.80 (2 H, m); 7.75 (1 H, m); 7.10–7.45 (10 H, m); 6.90 (1 H, s); 6.15 (1 H, s); 3.80–4.00 (1 H, m); 3.60–3.80 (1 H, m); 3.45–3.60 (2 H, m); 2.30 (6 H, s).

Example 58

2-(4,6-Dimethylpyrimidin-2-yloxy)-3-(2-(1-naphthoylamino)ethoxy)-3,3-diphenylpropionic acid (II-210)

ESI-MS: 562 (M+H)⁺
¹H-NMR (200 MHz, DMSO): 12.4–13.0 ppm (1 H, brd); 8.70 (1 H, tr); 8.20–8.30 (1 H, m); 7.85–8.80 (2 H, m); 7.10–7.60 (14 H, m); 6.90 (1 H, s); 6.15 (1 H, s); 3.80–4.00

(1 H, m); 3.65–3.80 (1 H, m); 3.50–3.60 (2 H, m); 2.30 (3 H, s).

The compounds in Table I can be prepared in a similar way or as described in the general part.

TABLE I

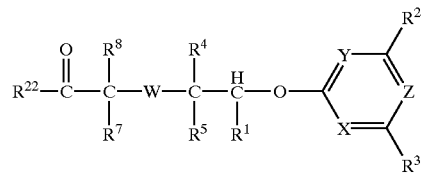

IA

| No. | R¹ | R⁴, R⁵ | R²² | R⁷ | R⁸ | R² | R³ | Z | X | Y | W |
|---|---|---|---|---|---|---|---|---|---|---|---|
| I-1 | COOH | Phenyl | Me₂N | Me | Me | Me | Me | CH | N | N | O |
| I-2 | COOH | Phenyl | Me₂N | H | H | OMe | OMe | CH | N | N | S |
| I-3 | COOH | Phenyl | Me₂N | H | H | OMe | Me | CH | N | N | O |
| I-4 | COOH | Phenyl | Me₂N | H | H | CH₂OH | Me | CH | N | N | O |
| I-5 | COOMe | Phenyl | Me₂N | H | H | OMe | CH₂—CH₂—CH₂—C | N | N | O |
| I-6 | COOH | Phenyl | Me₂N | H | H | OMe | O—CH₂—CH₂—C | N | N | O |
| I-7 | COOH | Phenyl | Me₂N | H | H | Ethyl | Ethyl | CH | N | N | O |
| I-8 | COOH | Phenyl | Me₂N | H | H | CF₃ | Me | CH | N | N | S |
| I-9 | COOH | Phenyl | Me₂N | H | H | OMe | CF₃ | CH | N | N | O |
| I-10 | COOH | Phenyl | Butyl-HN | H | H | Me | Me | CH | N | N | O |
| I-11 | COOH | Phenyl | Butyl-HN | Me | H | OMe | OMe | CH | N | N | S |
| I-12 | COOH | Phenyl | Butyl-HN | H | H | OMe | Me | CH | N | N | O |
| I-13 | COOH | Phenyl | Butyl-HN | Butyl | H | CH₂OH | Me | CH | N | N | O |
| I-14 | COOH | Phenyl | Butyl-HN | H | H | OMe | CH₂—CH₂—CH₂—C | N | N | O |
| I-15 | COOH | Phenyl | Butyl-HN | H | H | OMe | O—CH₂—CH₂—C | N | N | O |
| I-16 | COOH | Phenyl | Butyl-HN | H | H | Ethyl | Ethyl | CH | N | N | O |
| I-17 | COOH | 4-F-Phenyl | Butyl-HN | H | H | CF₃ | Me | CH | N | N | S |
| I-18 | COOH | Phenyl | Butyl-HN | H | H | OMe | CF₃ | CH | N | N | O |
| I-19 | COOH | Phenyl | Phenyl-HN | H | H | Me | Me | CH | N | N | O |
| I-20 | COOH | Phenyl | Phenyl-HN | H | H | OMe | OMe | CH | N | N | S |
| I-21 | COOH | Phenyl | Phenyl-HN | H | H | OMe | Me | CH | N | N | O |
| I-22 | COOH | Phenyl | Phenyl-HN | H | H | CH₂OH | Me | CH | N | N | O |
| I-23 | COOH | 4-F-Phenyl | Phenyl-HN | Me | Me | OMe | CH₂—CH₂—CH₂—C | N | N | O |
| I-24 | COOH | Phenyl | Phenyl-HN | H | H | OMe | O—CH₂—CH₂—C | N | N | O |
| I-25 | COOH | Phenyl | Phenyl-HN | H | H | Ethyl | Ethyl | CH | N | N | S |
| I-26 | COOH | 4-F-Phenyl | Phenyl-HN | H | H | CF₃ | Me | CH | N | N | O |
| I-27 | COOH | 4-F-Phenyl | Phenyl-HN | H | H | OMe | CF₃ | CH | N | N | O |
| I-28 | COOH | Phenyl | (4-Methylphenyl)—HN | H | H | Me | Me | CH | N | N | O |
| I-29 | COOH | Phenyl | (4-Methylphenyl)—HN | H | H | OMe | OMe | CH | N | N | O |
| I-30 | COOH | Phenyl | (4-Methylphenyl)—HN | H | H | OMe | Me | CH | N | N | O |
| I-31 | COOMe | Phenyl | (4-Methylphenyl)—HN | H | H | CH₂OH | Me | CH | N | N | O |
| I-32 | COOH | Phenyl | (4-Methylphenyl)—HN | H | H | OMe | CH₂—CH₂—CH₂—C | N | N | O |
| I-33 | COOH | Phenyl | (4-Methylphenyl)—HN | Me | Me | OMe | O—CH₂—CH₂—C | N | N | O |
| I-34 | COOH | Phenyl | (4-Methylphenyl)—HN | H | H | Ethyl | Ethyl | CH | N | N | S |
| I-35 | COOH | Phenyl | (4-Methylphenyl)—HN | H | H | CF₃ | Me | CH | N | N | O |
| I-36 | COOH | 4-F-Phenyl | (4-Methylphenyl)—HN | H | H | OMe | CF₃ | CH | N | N | O |
| I-37 | COOH | Phenyl | (4-Methoxylphenyl)—HN [sic] | H | H | Me | Me | CH | N | N | O |
| I-38 | COOH | Phenyl | (4-Methoxylphenyl)—HN [sic] | H | H | OMe | OMe | CH | N | N | S |
| I-39 | COOH | Phenyl | (4-Methoxylphenyl)—HN [sic] | H | H | OMe | Me | CH | N | N | O |
| I-40 | COOH | 4-F-Phenyl | (4-Methoxylphenyl)—HN [sic] | H | H | CH₂OH | Me | CH | N | N | O |
| I-41 | COOH | Phenyl | (4-Methoxylphenyl)—HN [sic] | H | H | OMe | CH₂—CH₂—CH₂—C | N | N | O |
| I-42 | COOH | Phenyl | (4-Methoxylphenyl)—HN [sic] | H | H | OMe | O—CH₂—CH₂—C | N | N | S |
| I-43 | COOH | Phenyl | (4-Me(hoxylphenyl)—HN [sic] | H | H | Ethyl | Ethyl | CH | N | N | O |
| I-44 | COOH | Phenyl | (4-Methoxylphenyl)—HN [sic] | H | H | CF₃ | Me | CH | N | N | O |
| I-45 | COOH | Phenyl | (4-Methoxylphenyl)—HN [sic] | Ethyl | H | OMe | CF₃ | CH | N | N | O |
| I-46 | COOH | Phenyl | (4-Chlorophenyl)—HN | H | H | Me | Me | CH | N | N | O |
| I-47 | COOH | Phenyl | (4-Chlorophenyl)—HN | H | H | OMe | OMe | CH | N | N | O |
| I-48 | COOH | Phenyl | (4-Chlorophenyl)—HN | Me | H | OMe | Me | CH | N | N | O |
| I-49 | COOH | Phenyl | (4-Chlorophenyl)—HN | H | H | CH₂OH | Me | CH | N | N | S |
| I-50 | COOH | Phenyl | (4-Chlorophenyl)—HN | H | H | OMe | CH₂—CH₂—CH₂—C | N | N | O |
| I-51 | COOMe | Phenyl | (4-Chlorophenyl)—HN | H | H | OMe | O—CH₂—CH₂—C | N | N | O |
| I-52 | COOH | Phenyl | (4-Chlorophenyl)—HN | H | H | Ethyl | Ethyl | CH | N | N | O |
| I-53 | COOH | Phenyl | (4-Chlorophenyl)—HN | H | H | CF₃ | Me | CH | N | N | O |
| I-54 | COOH | 4-F-Phenyl | (4-Chlorophenyl)—HN | H | H | OMe | CF₃ | CH | N | N | O |
| I-55 | COOH | Phenyl | (3,4-Dichlorophenyl)—HN | H | H | Me | Me | CH | N | N | O |
| I-56 | COOH | Phenyl | (3,4-Dichlorophenyl)—HN | H | H | OMe | OMe | CH | N | N | S |
| I-57 | COOH | Phenyl | (3,4-Dichlorophenyl)—HN | H | H | OMe | Me | CH | N | N | O |
| I-58 | COOH | Phenyl | (3,4-Dichlorophenyl)—HN | H | H | CH₂OH | Me | CH | N | N | O |
| I-59 | COOH | 4-F-Phenyl | (3,4-Dichlorophenyl)—HN | H | H | OMe | CH₂—CH₂—CH₂—C | N | N | O |
| I-60 | COOH | Phenyl | (3,4-Dichlorophenyl)—HN | Me | Me | OMe | O—CH₂—CH₂—C | N | N | O |
| I-61 | COOH | Phenyl | (3,4-Dichlorophenyl)—HN | H | H | Ethyl | Ethyl | CH | N | N | O |
| I-62 | COOH | Phenyl | (3,4-Dichlorophenyl)—HN | Me | Me | CF₃ | Me | CH | N | N | O |
| I-63 | COOH | Phenyl | (3,4-Dichlorophenyl)—HN | H | H | OMe | CF₃ | CH | N | N | O |

TABLE I-continued

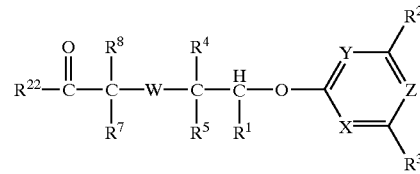

IA

| No. | R¹ | R⁴, R⁵ | R²² | R⁷ | R⁸ | R² | R³ | Z | X | Y | W |
|---|---|---|---|---|---|---|---|---|---|---|---|
| I-64 | COOH | Phenyl | (3,4-Dimethoxyphenyl)—HN | H | H | Me | Me | CH | N | N | O |
| I-65 | COOH | Phenyl | (3,4-Dimethoxyphenyl)—HN | H | H | OMe | OMe | CH | N | N | O |
| I-66 | COOH | Phenyl | (3,4-Dimethoxyphenyl)—HN | Me | H | OMe | Me | CH | N | N | O |
| I-67 | COOH | Phenyl | (3,4-Dimethoxyphenyl)—HN | H | H | $CH_2OH$ | Me | CH | N | N | O |
| I-68 | COOH | Phenyl | (3,4-Dimethoxyphenyl)—HN | H | H | OMe | $CH_2$—$CH_2$—$CH_2$—C | N | N | O |
| I-69 | COOH | 4-F-Phenyl | (3,4-Dimethoxyphenyl)—HN | H | H | OMe | O—$CH_2$—$CH_2$—C | N | N | S |
| I-70 | COOH | Phenyl | (3,4-Dimethoxyphenyl)—HN | H | H | Ethyl | Ethyl | CH | N | N | O |
| I-71 | COOH | Phenyl | (3,4-Dimethoxyphenyl)—HN | H | H | $CF_3$ | Me | CH | N | N | O |
| I-72 | COOH | Phenyl | (3,4-Dimethoxyphenyl)—HN | H | H | OMe | $CF_3$ | CH | N | N | O |
| I-73 | COOH | Phenyl | (3,4-Dimethoxyphenyl)—HN | H | H | Me | Me | CH | N | N | O |
| I-74 | COOH | Phenyl | (2,6-Dimethoxyphenyl)—HN | Me | Me | OMe | OMe | CH | N | N | O |
| I-75 | COOH | Phenyl | (2,6-Dimethoxyphenyl)—HN | H | H | OMe | Me | CH | N | N | O |
| I-76 | COOH | 4-F-Phenyl | (2,6-Dimethoxyphenyl)—HN | H | H | $CH_2OH$ | Me | CH | N | N | O |
| I-77 | COOH | Phenyl | (2,6-Dimethoxyphenyl)—HN | H | H | OMe | $CH_2$—$CH_2$—$CH_2$—C | N | N | S |
| I-78 | COOH | Phenyl | (2,6-Dimethoxyphenyl)—HN | H | H | OMe | O—$CH_2$—$CH_2$—C | N | N | O |
| I-79 | COOH | Phenyl | (2,6-Dimethoxyphenyl)—HN | H | H | Ethyl | Ethyl | CH | N | N | O |
| I-80 | COOH | Phenyl | (2,6-Dimethoxyphenyl)—HN | H | H | $CF_3$ | Me | CH | N | N | O |
| I-81 | COOH | Phenyl | (2,6-Dimethoxyphenyl)—HN | H | H | OMe | $CF_3$ | CH | N | N | S |
| I-82 | COOMe | Phenyl | (2,6-Diethylphenyl)—HN | H | H | Me | Me | CH | N | N | O |
| I-83 | COOH | Phenyl | (2,6-Diethylphenyl)—HN | H | H | OMe | OMe | CH | N | N | O |
| I-84 | COOH | 4-F-Phenyl | (2,6-Diethylphenyl)—HN | H | H | OMe | Me | CH | N | N | O |
| I-85 | COOH | Phenyl | (2,6-Diethylphenyl)—HN | Me | Me | $CH_2OH$ | Me | CH | N | N | O |
| I-86 | COOH | Phenyl | (2,6-Diethylphenyl)—HN | H | H | OMe | $CH_2$—$CH_2$—$CH_2$—C | N | N | O |
| I-87 | COOH | Phenyl | (2,6-Diethylphenyl)—HN | H | H | OMe | O—$CH_2$—$CH_2$—C | N | N | O |
| I-88 | COOH | Phenyl | (2,6-Diethylphenyl)—HN | Et | H | Ethyl | Ethyl | CH | N | N | O |
| I-89 | COOH | Phenyl | (2,6-Diethylphenyl)—HN | H | H | $CF_3$ | Me | CH | N | N | O |
| I-90 | COOH | Phenyl | (2,6-Diethylphenyl)—HN | H | H | OMe | $CF_3$ | CH | N | N | O |
| I-91 | COOH | Phenyl | (2,6-Diisopropylphenyl)—HN | H | H | Me | Me | CH | N | N | O |
| I-92 | COOH | 4-F-Phenyl | (2,6-Diisopropylphenyl)—HN | H | H | OMe | OMe | CH | N | N | O |
| I-93 | COOH | Phenyl | (2,6-Diisopropylphenyl)—HN | H | H | OMe | Me | CH | N | N | O |
| I-94 | COOH | Phenyl | (2,6-Diisopropylphenyl)—HN | H | H | $CH_2OH$ | Me | CH | N | N | O |
| I-95 | COOH | Phenyl | (2,6-Diisopropylphenyl)—HN | Et | H | OMe | $CH_2$—$CH_2$—$CH_2$—C | N | N | O |
| I-96 | COOMe | Phenyl | (2,6-Diisopropylphenyl)—HN | H | H | OMe | O—$CH_2$—$CH_2$—C | N | N | S |
| I-97 | COOH | Phenyl | (2,6-Diisopropylphenyl)—HN | H | H | Ethyl | Ethyl | CH | N | N | O |
| I-98 | COOH | Phenyl | (2,6-Diisopropylphenyl)—HN | H | H | $CF_3$ | Me | CH | N | N | S |
| I-99 | COOH | Phenyl | (2,6-Diisopropylphenyl)—HN | Me | Me | OMe | $CF_3$ | CH | N | N | O |
| I-100 | COOH | Phenyl | (N-Butyl-N-Me)—N | H | H | Me | Me | CH | N | N | O |
| I-101 | COOH | Phenyl | (N-Butyl-N-Me)—N | H | H | OMe | OMe | CH | N | N | O |
| I-102 | COOH | 4-F-Phenyl | (N-Butyl-N-Me)—N | H | H | OMe | Me | CH | N | N | O |
| I-103 | COOH | Phenyl | (N-Butyl-N-Me)—N | H | H | $CH_2OH$ | Me | CH | N | N | O |
| I-104 | COOH | Phenyl | (N-Butyl-N-Me)—N | Butyl | H | OMe | $CH_2$—$CH_2$—$CH_2$—C | N | N | O |
| I-105 | COOH | Phenyl | (N-Butyl-N-Me)—N | H | H | OMe | O—$CH_2$—$CH_2$—C | N | N | S |
| I-106 | COOH | Phenyl | (N-Butyl-N-Me)—N | H | H | Ethyl | Ethyl | CH | N | N | O |
| I-107 | COOH | 4-F-Phenyl | (N-Butyl-N-Me)—N | H | H | $CF_3$ | Me | CH | N | N | O |
| I-108 | COOH | Phenyl | (N-Butyl-N-Me)—N | H | H | OMe | $CF_3$ | CH | N | N | O |
| I-109 | COOH | Phenyl | (N-Phenyl-N-Me)—N | H | H | Me | Me | CH | N | N | O |
| I-110 | COOH | Phenyl | (N-Phenyl-N-Me)—N | H | H | OMe | OMe | CH | N | N | O |
| I-111 | COOH | Phenyl | (N-Phenyl-N-Me)—N | H | H | OMe | Me | CH | N | N | O |
| I-112 | COOH | Phenyl | (N-Phenyl-N-Me)—N | Ethyl | H | $CH_2OH$ | Me | CH | N | N | O |
| I-113 | COOH | 4-F-Phenyl | (N-Phenyl-N-Me)—N | H | H | OMe | $CH_2$—$CH_2$—$CH_2$—C | N | N | O |
| I-114 | COOH | Phenyl | (N-Phenyl-N-Me)—N | H | H | OMe | O—$CH_2$—$CH_2$—C | N | N | S |
| I-115 | COOH | Phenyl | (N-Phenyl-N-Me)—N | Ethyl | H | Ethyl | Ethyl | CH | N | N | O |
| I-116 | COOH | Phenyl | (N-Phenyl-N-Me)—N | H | H | $CF_3$ | Me | CH | N | N | O |
| I-117 | COOH | Phenyl | (N-Phenyl-N-Me)—N | H | H | OMe | $CF_3$ | CH | N | N | O |
| I-118 | COOH | Phenyl | (N-4-Methylphenyl-N-Methyl)—N | H | H | Me | Me | CH | N | N | O |
| I-119 | COOH | Phenyl | (N-4-Methylphenyl-N-Methyl)—N | H | H | OMe | OMe | CH | N | N | O |
| I-120 | COOH | Phenyl | (N-4-Methylphenyl-N-Methyl)—N | H | H | OMe | Me | CH | N | N | S |
| I-121 | COOH | Phenyl | (N-4-Methylphenyl-N-Methyl)—N | Me | Me | $CH_2OH$ | Me | CH | N | N | O |
| I-122 | COOH | Phenyl | (N-4-Methylphenyl-N-Methyl)—N | H | H | OMe | $CH_2$—$CH_2$—$CH_2$—C | N | N | O |
| I-123 | COOH | Phenyl | (N-4-Methylphenyl-N-Methyl)—N | H | H | OMe | O—$CH_2$—$CH_2$—C | N | N | O |
| I-124 | COOMe | 4-F-Phenyl | (N-4-Methylphenyl-N-Methyl)—N | H | H | Ethyl | Ethyl | CH | N | N | O |
| I-125 | COOH | Phenyl | (N-4-Methylphenyl-N-Methyl)—N | H | H | $CF_3$ | Me | CH | N | N | O |
| I-126 | COOH | Phenyl | (N-4-Methylphenyl-N-Methyl)—N | H | H | OMe | $CF_3$ | CH | N | N | O |
| I-127 | COOH | Phenyl | (N-4-Methoxylphenyl-N—Me)—N | H | H | Me | Me | CH | N | N | O |
| I-128 | COOH | Phenyl | (N-4-Methoxylphenyl-N—Me)—N [sic] | H | H | OMe | OMe | CH | N | N | O |
| I-129 | COOH | Phenyl | (N-4-Methoxylphenyl-N—Me)—N [sic] | H | H | OMe | Me | CH | N | N | O |

TABLE I-continued

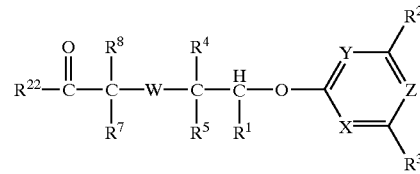

IA

| No. | R$^1$ | R$^4$, R$^5$ | R$^{22}$ | R$^7$ | R$^8$ | R$^2$ | R$^3$ | Z | X | Y | W |
|---|---|---|---|---|---|---|---|---|---|---|---|
| I-130 | COOH | Phenyl | (N-4-Methoxylphenyl-N—Me)—N [sic] | Me | Me | CH$_2$OH | Me | CH | N | N | O |
| I-131 | COOH | 4-F-Phenyl | (N-4-Methoxylphenyl-N—Me)—N [sic] | H | H | OMe | CH$_2$—CH$_2$—CH$_2$—C | N | N | O |
| I-132 | COOH | Phenyl | (N-4-Methoxylphenyl-N—Me)—N [sic] | H | H | OMe | O—CH$_2$—CH$_2$—C | N | N | S |
| I-133 | COOH | Phenyl | (N-4-Methoxylphenyl-N—Me)—N [sic] | H | H | Ethyl | Ethyl | CH | N | N | O |
| I-134 | COOH | 4-F-Phenyl | (N-4-Methoxylphenyl-N—Me)—N [sic] | H | H | CF$_3$ | Me | CH | N | N | O |
| I-135 | COOH | Phenyl | (N-4-Methoxylphenyl-N—Me)—N [sic] | H | H | OMe | CF$_3$ | CH | N | N | O |
| I-136 | COOMe | Phenyl | (N-3,4-Dimethoxylphenyl-N—Me)—N [sic] | H | H | Me | Me | CH | N | N | O |
| I-137 | COOH | Phenyl | (N-3,4-Dimethoxylphenyl-N—Me)—N [sic] | Butyl | H | OMe | OMe | CH | N | N | O |
| I-138 | COOH | Phenyl | (N-3,4-Dimethoxylphenyl-N—Me)—N [sic] | H | H | OMe | Me | CH | N | N | O |
| I-139 | COOH | Phenyl | (N-3,4-Dimethoxylphenyl-N—Me)—N [sic] | H | H | CH$_2$OH | Me | CH | N | N | O |
| I-140 | COOH | Phenyl | (N-3,4-Dimethoxylphenyl-N—Me)—N [sic] | H | H | OMe | CH$_2$—CH$_2$—CH$_2$—C | N | N | O |
| I-141 | COOH | Phenyl | (N-3,4-Dimethoxylphenyl-N—Me)—N [sic] | H | H | OMe | O—CH$_2$—C112—C | N | N | S |
| I-142 | COOMe | Phenyl | (N-3,4-Dimethoxylphenyl-N—Me)—N [sic] | H | H | Ethyl | Ethyl | CH | N | N | O |
| I-143 | COOH | 4-F-Phenyl | (N-3,4-Dimethoxylphenyl-N—Me)—N [sic] | H | H | CF$_3$ | Me | CH | N | N | O |
| I-144 | COOH | Phenyl | (N-3,4-Dimethoxylphenyl-N—Me)—N [sic] | H | H | OMe | CF$_3$ | CH | N | N | O |
| I-145 | COOH | Phenyl | (N-3,4-Dichlorophenyl-N—Me)—N | H | H | Me | Me | CH | N | N | O |
| I-146 | COOH | Phenyl | (N-3,4-Dichlorophenyl-N—Me)—N | 11 | H | OMe | OMe | CH | N | N | O |
| I-147 | COOH | Phenyl | (N-3,4-Dichlorophenyl-N—Me)—N | Me | Me | OMe | Me | CH | N | N | O |
| I-148 | COOH | Phenyl | (N-3,4-Dichlorophenyl-N—Me)—N | H | H | CH$_2$OH | Me | CH | N | N | O |
| I-149 | COOH | Phenyl | (N-3,4-Dichlorophenyl-N—Me)—N | H | H | OMe | CH$_2$—CH$_2$—CH$_2$—C | N | N | O |
| I-150 | COOH | Phenyl | (N-3,4-Dichlorophenyl-N—Me)—N | H | H | OMe | O—CH$_2$—CH$_2$—C | N | N | O |
| I-151 | COOH | 4-F-Phenyl | (N-3,4-Dichlorophenyl-N—Me)—N | Me | Me | Ethyl | Ethyl | CH | N | N | S |
| I-152 | COOH | Phenyl | (N-3,4-Dichlorophenyl-N—Me)—N | 11 | H | CF$_3$ | Me | CH | N | N | O |
| I-153 | COOH | Phenyl | (N-3,4-Dichlorophenyl-N—Me)—N | H | H | OMe | CF$_3$ | CH | N | N | O |
| I-154 | COOH | Phenyl | (N-4-Chlorophenyl-N—Me)—N | Ethyl | H | Me | Me | CH | N | N | O |
| I-155 | COOH | Phenyl | (N-4-Chlorophenyl-N—Me)—N | H | H | OMe | OMe | CH | N | N | S |
| I-156 | COOH | Phenyl | (N-4-Chlorophenyl-N—Me)—N | H | H | OMe | Me | CH | N | N | O |
| I-157 | COOH | 4-F-Phenyl | (N-4-Chlorophenyl-N—Me)—N | Ethyl | H | CH$_2$OH | Me | CH | N | N | O |
| I-158 | COOH | Phenyl | (N-4-Chlorophenyl-N—Me)—N | H | H | OMe | CH$_2$—CH$_2$—CH$_2$—C | N | N | O |
| I-159 | COOH | Phenyl | (N-4-Chlorophenyl-N—Me)—N | H | H | OMe | O—CH$_2$—CH$_2$—C | N | N | O |
| I-160 | COOH | 4-F-Phenyl | (N-4-Chlorophenyl-N—Me)—N | H | H | Ethyl | Ethyl | CH | N | N | O |
| I-161 | COOH | Phenyl | (N-4-Chlorophenyl-N—Me)—N | Me | Me | CF$_3$ | Me | CH | N | N | O |
| I-162 | COOH | Phenyl | (N-4-Chlorophenyl-N—Me)—N | H | H | OMe | CF$_3$ | CH | N | N | O |
| I-163 | COOH | Phenyl | (N-2,6-Dimethoxyphenyl-N—Me)—N [sic] | H | H | Me | Me | CH | N | N | S |
| I-164 | COOH | 4-F-Phenyl | (N-2,6-Dimethoxyphenyl-N—Me)—N [sic] | H | H | OMe | OMe | CH | N | N | O |
| I-165 | COOH | Phenyl | (N-2,6-Dimethoxyphenyl-N—Me)—N [sic] | Me | H | OMe | Me | CH | N | N | O |
| I-166 | COOH | Phenyl | (N-2,6-Dimethoxyphenyl-N—Me)—N [sic] | H | H | CH$_2$OH | Me | CH | N | N | O |
| I-167 | COOH | 4-F-Phenyl | (N-2,6-Dimethoxyphenyl-N—Me)—N [sic] | H | H | OMe | CH$_2$—CH$_2$—CH$_2$—C | N | N | O |
| I-168 | COOH | Phenyl | (N-2,6-Dimethoxyphenyl-N—Me)—N [sic] | H | H | OMe | O—CH$_2$—CH$_2$—C | N | N | S |
| I-169 | COOH | Phenyl | (N-2,6-Dimethoxyphenyl-N—Me)—N [sic] | H | H | Ethyl | Ethyl | CH | N | N | O |
| I-170 | COOH | Phenyl | (N-2,6-Dimethoxyphenyl-N—Me)—N [sic] | H | H | CF$_3$ | Me | CH | N | N | O |
| I-171 | COOH | Phenyl | (N-2,6-Dimethoxyphenyl-N—Me)—N [sic] | H | H | OMe | CF$_3$ | CH | N | N | O |
| I-172 | COOMe | Phenyl | (N-2,6-Diethylphenyl-N—Me)—N | H | H | Me | Me | CH | N | N | S |
| I-173 | COOH | 4-F-Phenyl | (N-2,6-Diethylphenyl-N—Me)—N | H | H | OMe | OMe | CH | N | N | O |
| I-174 | COOH | Phenyl | (N-2,6-Diethylphenyl-N—Me)—N | H | H | OMe | Me | CH | N | N | O |
| I-175 | COOH | Phenyl | (N-2,6-Diethylphenyl-N—Me)—N | H | H | CH$_2$OH | Me | CH | N | N | O |
| I-176 | COOH | Phenyl | (N-2,6-Diethylphenyl-N—Me)—N | Ethyl | H | OMe | CH$_2$—CH$_2$—CH$_2$—C | N | N | O |
| I-177 | COOH | Phenyl | (N-2,6-Diethylphenyl-N—Me)—N | H | H | OMe | O—CH$_2$—CH$_2$—C | N | N | O |
| I-178 | COOH | Phenyl | (N-2,6-Diethylphenyl-N—Me)—N | H | H | Ethyl | Ethyl | CH | N | N | O |
| I-179 | COOH | Phenyl | (N-2,6-Diethylphenyl-N—Me)—N | H | H | CF$_3$ | Me | CH | N | N | O |
| I-180 | COOH | Phenyl | (N-2,6-Diethylphenyl-N—Me)—N | H | H | OMe | CF$_3$ | CH | N | N | O |
| I-181 | COOH | 4-F-Phenyl | (N-2,6-Diisopropylphenyl-N—Me)—N | H | H | Me | Me | CH | N | N | O |
| I-182 | COOH | Phenyl | (N-2,6-Diisopropylphenyl-N—Me)—N | H | H | OMe | OMe | CH | N | N | O |
| I-183 | COOH | Phenyl | (N-2,6-Diisopropylphenyl-N—Me)—N | H | H | OMe | Me | CH | N | N | O |
| I-184 | COOMe | Phenyl | (N-2,6-Diisopropylphenyl-N—Me)—N | H | H | CH$_2$OH | Me | CH | N | N | O |
| I-185 | COOH | Phenyl | (N-2,6-Diisopropylphenyl-N—Me)—N | H | H | OMe | CH$_2$—CH$_2$—CH$_2$—C | N | N | O |
| I-186 | COOH | Phenyl | (N-2,6-Diisopropylphenyl-N—Me)—N | Me | Me | OMe | O—CH$_2$—CH$_2$—C | N | N | O |
| I-187 | COOH | 4-F-Phenyl | (N-2,6-Diisopropylphenyl-N—Me)—N | H | H | Ethyl | Ethyl | CH | N | N | S |
| I-188 | COOH | Phenyl | (N-2,6-Diisopropylphenyl-N—Me)—N | H | H | CF$_3$ | Me | CH | N | N | O |
| I-189 | COOH | Phenyl | (N-2,6-Diisopropylphenyl-N—Me)—N | H | H | OMe | CF$_3$ | CH | N | N | O |
| I-190 | COOH | Phenyl | (N-Phenyl-N-Butyl)—N | H | H | Me | Me | CH | N | N | O |
| I-191 | COOH | Phenyl | (N-Phenyl-N-Butyl)—N | H | H | OMe | OMe | CH | N | N | O |
| I-192 | COOH | Phenyl | (N-Phenyl-N-Butyl)—N | H | H | OMe | Me | CH | N | N | O |
| I-193 | COOH | Phenyl | (N-Phenyl-N-Butyl)—N | Me | Me | CH$_2$OH | Me | CH | N | N | O |
| I-194 | COOH | Phenyl | (N-Phenyl-N-Butyl)—N | H | H | OMe | CH$_2$—CH$_2$—CH$_2$—C | N | N | S |
| I-195 | COOH | 4-F-Phenyl | (N-Phenyl-N-Butyl)—N | H | H | OMe | O—CH$_2$—CH$_2$—C | N | N | O |

TABLE I-continued

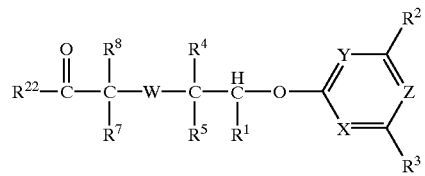

IA

| No. | R$^1$ | R$^4$, R$^5$ | R$^{22}$ | R$^7$ | R$^8$ | R$^2$ | R$^3$ | Z | X | Y | W |
|---|---|---|---|---|---|---|---|---|---|---|---|
| I-196 | COOH | Phenyl | (N-Phenyl-N-Butyl)—N | H | H | Ethyl | Ethyl | CH | N | N | O |
| I-197 | COOH | Phenyl | (N-Phenyl-N-Butyl)—N | Me | H | CF$_3$ | Me | CH | N | N | O |
| I-198 | COOH | Phenyl | (N-Phenyl-N-Butyl)—N | H | H | OMe | CF$_3$ | CH | N | N | O |
| I-199 | COOH | Phenyl | (N-4-Methylphenyl-N-Butyl)—N | H | H | Me | Me | CH | N | N | O |
| I-200 | COOH | Phenyl | (N-4-Methylphenyl-N-Butyl)—N | Me | H | OMe | OMe | CH | N | N | O |
| I-201 | COOMe | Phenyl | (N-4-Methylphenyl-N-Butyl)—N | H | H | OMe | Me | CH | N | N | O |
| I-202 | COOH | Phenyl | (N-4-Methylphenyl-N-Butyl)—N | H | H | CH$_2$OH | Me | CH | N | N | O |
| I-203 | COOH | 4-F-Phenyl | (N-4-Methylphenyl-N-Butyl)—N | H | H | OMe | CH$_2$—CH$_2$—CH$_2$—C | N | N | O |
| I-204 | COOH | Phenyl | (N-4-Methylphenyl-N-Butyl)—N | H | H | OMe | O—CH$_2$—CH$_2$—C | N | N | O |
| I-205 | COOH | Phenyl | (N-4-Methylphenyl-N-Butyl)—N | H | H | Ethyl | Ethyl | CH | N | N | O |
| I-206 | COOH | Phenyl | (N-4-Methylphenyl-N-Butyl)—N | Me | Me | CF$_3$ | Me | CH | N | N | O |
| I-207 | COOH | Phenyl | (N-4-Methylphenyl-N-Butyl)—N | H | H | OMe | CF$_3$ | CH | N | N | O |
| I-208 | COOH | Phenyl | (N-4-Methoxyphenyl-N-Butyl)—N | H | H | Me | Me | CH | N | N | O |
| I-209 | COOH | Phenyl | (N-4-Methoxyphenyl-N-Butyl)—N | Me | Me | OMe | OMe | CH | N | N | O |
| I-210 | COOH | Phenyl | (N-4-Methoxyphenyl-N-Butyl)—N | H | H | OMe | Me | CH | N | N | O |
| I-211 | COOH | 4-F-Phenyl | (N-4-Methoxyphenyl-N-Butyl)—N | H | H | CH$_2$OH | Me | CH | N | N | O |
| I-212 | COOH | Phenyl | (N-4-Methoxyphenyl-N-Butyl)—N | Me | H | OMe | CH$_2$—CH$_2$—CH$_2$—C | N | N | O |
| I-213 | COOH | Phenyl | (N-4-Methoxyphenyl-N-Butyl)—N | H | H | OMe | O—CH$_2$—CH$_2$—C | N | N | S |
| I-214 | COOH | Phenyl | (N-4-Methoxyphenyl-N-Butyl)—N | H | H | Ethyl | Ethyl | CH | N | Y | O |
| I-215 | COOH | Phenyl | (N-4-Methoxyphenyl-N-Butyl)—N | H | H | CF$_3$ | Me | CH | N | N | O |
| I-216 | COOH | Phenyl | (N-4-Methoxyphenyl-N-Butyl)—N | Bu | H | OMe | CF$_3$ | CH | N | N | O |
| I-217 | COOH | Phenyl | (N-3,4-Dimethoxyphenyl-N-Butyl)—N | H | H | Me | Me | CH | N | N | O |
| I-218 | COOH | Phenyl | (N-3,4-Dimethoxyphenyl-N-Butyl)—N | Propyl | H | OMe | OMe | CH | N | N | O |
| I-219 | COOH | Phenyl | (N-3,4-Dimethoxyphenyl-N-Butyl)—N | H | H | OMe | Me | CH | N | N | O |
| I-220 | COOH | Phenyl | (N-3,4-Dimethoxyphenyl-N-Butyl)—N | H | H | CH$_2$OH | Me | CH | N | N | O |
| I-221 | COOH | 4-F-Phenyl | (N-3,4-Dimethoxyphenyl-N-Butyl)—N | H | H | OMe | CH$_2$—CH$_2$—CH$_2$—C | N | N | O |
| I-222 | COOH | Phenyl | (N-3,4-Dimethoxyphenyl-N-Butyl)—N | H | H | OMe | O—CH$_2$—CH$_2$—C | N | N | O |
| I-223 | COOH | 4-F-Phenyl | (N-3,4-Dimethoxyphenyl-N-Butyl)—N | H | H | Ethyl | Ethyl | CH | N | N | O |
| I-224 | COOH | Phenyl | (N-3,4-Dimethoxyphenyl-N-Butyl)—N | H | H | CF$_3$ | Me | CH | N | N | S |
| I-225 | COOH | Phenyl | (N-3,4-Dimethoxyphenyl-N-Butyl)—N | H | H | OMe | CF$_3$ | CH | N | N | O |
| I-226 | COOH | Phenyl | (N-3,4-Dichlorophenyl-N-Butyl)—N | H | H | Me | Me | CH | N | N | O |
| I-227 | COOH | Phenyl | (N-3,4-Dichlorophenyl-N-Butyl)—N | Me | Me | OMe | OMe | CH | N | N | O |
| I-228 | COOH | Phenyl | (N-3,4-Dichlorophenyl-N-Butyl)—N | H | H | OMe | Me | CH | N | N | O |
| I-229 | COOH | Phenyl | (N-3,4-Dichlorophenyl-N-Butyl)—N | H | H | CH$_2$OH | Me | CH | N | N | S |
| I-230 | COOH | Phenyl | (N-3,4-Dichlorophenyl-N-Butyl)—N | H | H | OMe | CH$_2$—CH$_2$—CH$_2$—C | N | N | O |
| I-231 | COOH | Phenyl | (N-3,4-Dichlorophenyl-N-Butyl)—N | H | H | OMe | O—CH$_2$—CH$_2$—C | N | N | O |
| I-232 | COOMe | Phenyl | (N-3,4-Dichlorophenyl-N-Butyl)—N | H | H | Ethyl | Ethyl | CH | N | N | O |
| I-233 | COOH | 4-F-Phenyl | (N-3,4-Dichlorophenyl-N-Butyl)—N | H | H | CF$_3$ | Me | CH | N | N | O |
| I-234 | COOH | Phenyl | (N-3,4-Dichlorophenyl-N-Butyl)—N | Propyl | H | OMe | CF$_3$ | CH | N | N | O |
| I-235 | COOH | Phenyl | (N-4-Chlorophenyl-N-Butyl)—N | H | H | Me | Me | CH | N | N | O |
| I-236 | COOH | Phenyl | (N-4-Chlorophenyl-N-Butyl)—N | H | H | OMe | OMe | CH | N | N | O |
| I-237 | COOH | Phenyl | (N-4-Chlorophenyl-N-Butyl)—N | Me | Me | OMe | Me | CH | N | N | O |
| I-238 | COOH | Phenyl | (N-4-Chlorophenyl-N-Butyl)—N | H | H | CH$_2$OH | Me | CH | N | N | S |
| I-239 | COOH | Phenyl | (N-4-Chlorophenyl-N-Butyl)—N | H | H | OMe | CH$_2$—CH$_2$—CH$_2$—C | N | N | O |
| I-240 | COOH | 4-F-Phenyl | (N-4-Chlorophenyl-N-Butyl)—N | H | H | OMe | O—CH$_2$—CH$_2$—C | N | N | O |
| I-241 | COOH | Phenyl | (N-4-Chlorophenyl-N-Butyl)—N | H | H | Ethyl | Ethyl | CH | N | N | O |
| I-242 | COOH | Phenyl | (N-4-Chlorophenyl-N-Butyl)—N | H | H | CF$_3$ | Me | CH | N | N | O |
| I-243 | COOH | Phenyl | (N-4-Chlorophenyl—N-Butyl)—N | H | H | OMe | CF$_3$ | CH | N | N | O |
| I-244 | COOH | Phenyl | (N-2,6-Dimethoxyphenyl-N-Butyl)—N [sic] | H | H | Me | Me | CH | N | N | O |
| I-245 | COOH | Phenyl | (N-2,6-Dimethoxyphenyl-N-Butyl)—N [sic] | Butyl | H | OMe | OMe | CH | N | N | S |
| I-246 | COOH | 4-F-Phenyl | (N-2,6-Dimethoxyphenyl-N-Butyl)—N [sic] | H | H | OMe | Me | CH | N | N | O |
| I-247 | COOH | Phenyl | (N-2,6-Dimethoxyphenyl-N-Butyl)—N [sic] | H | H | CH$_2$OH | Me | CH | N | Y | O |
| I-248 | COOH | Phenyl | (N-2,6-Dimethoxyphenyl-N-Butyl)—N [sic] | H | H | OMe | CH$_2$—CH$_2$—CH$_2$—C | N | N | O |
| I-249 | COOH | Phenyl | (N-2,6-Dimethoxyphenyl-N-Butyl)—N [sic] | Butyl | H | OMe | O—CH$_2$—CH$_2$—C | N | N | O |
| I-250 | COOH | Phenyl | (N-2,6-Dimethoxyphenyl-N-Butyl)—N [sic] | H | H | Ethyl | Ethyl | CH | N | N | O |
| I-251 | COOH | Phenyl | (N-2,6-Dimethoxyphenyl-N-Butyl)—N [sic] | H | H | CF$_3$ | Me | CH | N | N | O |
| I-252 | COOH | Phenyl | (N-2,6-Dimethoxyphenyl-N-Butyl)—N [sic] | H | H | OMe | CF$_3$ | CH | N | N | O |
| I-253 | COOH | Phenyl | (N-2,6-Diethylphenyl-N-Butyl)—N | H | H | Me | Me | CH | N | N | O |
| I-254 | COOH | Phenyl | (N-2,6-Dielhylphenyl-N-Butyl)—N | H | H | OMe | OMe | CH | N | N | O |
| I-255 | COOH | Phenyl | (N-2,6-Diethylphenyl-N-Butyl)—N | Me | Me | OMe | Me | CH | N | N | O |
| I-256 | COOH | Phenyl | (N-2,6-Diethylphenyl-N-Butyl)—N | H | H | CH$_2$OH | Me | CH | N | N | O |
| I-257 | COOH | Phenyl | (N-2,6-Diethylphenyl-N-Butyl)—N | H | H | OMe | CH$_2$—CH$_2$—CH$_2$—C | N | N | O |
| I-258 | COOH | Phenyl | (N-2,6-Diethylphenyl-N-Butyl)—N | Ethyl | H | OMe | O—CH$_2$—CH$_2$—C | N | N | O |
| I-259 | COOH | Phenyl | (N-2,6-Diethylphenyl-N-Butyl)—N | H | H | Ethyl | Ethyl | CH | N | N | O |
| I-260 | COOH | Phenyl | (N-2,6-Diethylphenyl-N-Butyl)—N | H | H | CF$_3$ | Me | CH | N | N | O |
| I-261 | COOH | Phenyl | (N-2,6-Diethylphenyl-N-Butyl)—N | H | H | OMe | CF$_3$ | CH | N | N | O |

TABLE I-continued

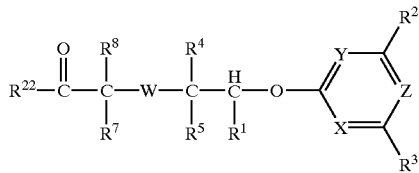

IA

| No. | R¹ | R⁴, R⁵ | R²² | R⁷ | R⁸ | R² | R³ | Z | X | Y | W |
|---|---|---|---|---|---|---|---|---|---|---|---|
| I-262 | COOH | Phenyl | (N-2,6-Diisopropylphenyl-N-Butyl)—N | H | H | Me | Me | CH | N | N | S |
| I-263 | COOMe | Phenyl | (N-2,6-Diisopropylphenyl-N-Butyl)—N | H | H | OMe | OMe | CH | N | N | O |
| I-264 | COOH | Phenyl | (N-2,6-Diisopropylphenyl-N-Butyl)—N | H | H | OMe | Me | CH | N | N | O |
| I-265 | COOH | Phenyl | (N-2,6-Diisopropylphenyl-N-Butyl)—N | H | H | $CH_2OH$ | Me | CH | N | N | O |
| I-266 | COOH | 4-F-Phenyl | (N-2,6-Diisopropylphenyl-N-Butyl)—N | H | H | OMe | $CH_2$—$CH_2$—$CH_2$—C | N | N | O |
| I-267 | COOH | 4-F-Phenyl | (N-2,6-Diisopropylphenyl-N-Butyl)—N | H | H | OMe | O—$CH_2$—$CH_2$—C | N | N | S |
| I-268 | COOH | Phenyl | (N-2,6-Diisopropylphenyl-N-Butyl)—N | H | H | Ethyl | Ethyl | CH | N | N | O |
| I-269 | COOH | Phenyl | (N-2,6-Diisopropylphenyl-N-Butyl)—N | H | H | $CF_3$ | Me | CH | N | N | O |
| I-270 | COOH | Phenyl | (N-2,6-Diisopropylphenyl-N-Butyl)—N | Butyl | H | OMe | $CF_3$ | CH | N | N | O |
| I-271 | COOH | Phenyl | (N-Phenyl-N-Isopropyl)—N | H | H | Me | Me | CH | N | N | O |
| I-272 | COOH | Phenyl | (N-Phenyl-N-Isopropyl)—N | H | H | OMe | OMe | CH | N | N | O |
| I-273 | COOH | Phenyl | (N-Phenyl-N-Isopropyl)—N | H | H | OMe | Me | CH | N | N | O |
| I-274 | COOH | Phenyl | (N-Phenyl-N-Isopropyl)—N | Me | Me | $CH_2OH$ | Me | CH | N | N | O |
| I-275 | COOH | Phenyl | (N-Phenyl-N-Isopropyl)—N | H | H | OMe | $CH_2$—$CH_2$—$CH_2$—C | N | N | O |
| I-276 | COOH | 4-F-Phenyl | (N-Phenyl-N-Isopropyl)—N | H | H | OMe | O—$CH_2$—$CH_2$—C | N | N | O |
| I-277 | COOH | Phenyl | (N-Phenyl-N-Isopropyl)—N | H | H | Ethyl | Ethyl | CH | N | N | S |
| I-278 | COOH | Phenyl | (N-Phenyl-N-Isopropyl)—N | H | H | $CF_3$ | Me | CH | N | N | O |
| I-279 | COOH | Phenyl | (N-Phenyl-N-Isopropyl)—N | H | H | OMe | $CF_3$ | CH | N | N | O |
| I-280 | COOH | Phenyl | (—$CH_2$—$CH_2$—$CH_2$—$CH_2$—)N | H | H | Me | Me | CH | N | N | O |
| I-281 | COOH | Phenyl | (—$CH_2$—$CH_2$—$CH_2$—$CH_2$—)N | H | H | OMe | OMe | CH | N | N | O |
| I-282 | COOH | 4-F-Phenyl | (—$CH_2$—$CH_2$—$CH_2$—$CH_2$—)N | H | H | OMe | Me | CH | N | N | O |
| I-283 | COOH | Phenyl | (—$CH_2$—$CH_2$—$CH_2$—$CH_2$—)N | H | H | $CH_2OH$ | Me | CH | N | N | O |
| I-284 | COOH | Phenyl | (—$CH_2$—$CH_2$—$CH_2$—$CH_2$—)N | Propyl | H | OMe | $CH_2$—$CH_2$—$CH_2$—C | N | N | O |
| I-285 | COOH | Phenyl | (—$CH_2$—$CH_2$—$CH_2$—$CH_2$—)N | H | H | OMe | O—$CH_2$—$CH_2$—C | N | N | O |
| I-286 | COOH | Phenyl | (—$CH_2$—$CH_2$—$CH_2$—$CH_2$—)N | H | H | Ethyl | Ethyl | CH | N | N | S |
| I-287 | COOH | Phenyl | (—$CH_2$—$CH_2$—$CH_2$—$CH_2$—)N | H | H | $CF_3$ | Me | CH | N | N | O |
| I-288 | COOH | Phenyl | (—$CH_2$—$CH_2$—$CH_2$—$CH_2$—)N | Me | Me | OMe | $CF_3$ | CH | N | N | O |
| I-289 | COOH | Phenyl | (—$CH_2$—$CH_2$—$CH_2$—$CH_2$—$CH_2$—)N | H | H | Me | Me | CH | N | N | O |
| I-290 | COOH | Phenyl | (—$CH_2$—$CH_2$—$CH_2$—$CH_2$—$CH_2$—)N | H | H | OMe | OMe | CH | N | N | O |
| I-291 | COOH | Phenyl | (—$CH_2$—$CH_2$—$CH_2$—$CH_2$—$CH_2$—)N | H | H | OMe | Me | CH | N | N | O |
| I-292 | COOH | 4-F-Phenyl | (—$CH_2$—$CH_2$—$CH_2$—$CH_2$—$CH_2$—)N | H | H | $CH_2OH$ | Me | CH | N | N | O |
| I-293 | COOH | Phenyl | (—$CH_2$—$CH_2$—$CH_2$—$CH_2$—$CH_2$—)N | H | H | OMe | $CH_2$—$CH_2$—$CH_2$—C | N | N | O |
| I-294 | COOH | Phenyl | (—$CH_2$—$CH_2$—$CH_2$—$CH_2$—$CH_2$—)N | H | H | OMe | O—$CH_2$—$CH_2$—C | N | N | O |
| I-295 | COOH | Phenyl | (—$CH_2$—$CH_2$—$CH_2$—$CH_2$—$CH_2$—)N | Me | H | Ethyl | Ethyl | CH | N | N | S |
| I-296 | COOH | Phenyl | (—$CH_2$—$CH_2$—$CH_2$—$CH_2$—$CH_2$—)N | H | H | $CF_3$ | Me | CH | N | N | O |
| I-297 | COOH | Phenyl | (—$CH_2$—$CH_2$—$CH_2$—$CH_2$—$CH_2$—)N | H | H | OMe | $CF_3$ | CH | N | N | O |
| I-298 | COOH | Phenyl | (—$CH_2$—$CH_2$—$CH_2$—$CH_2$—$CH_2$—$CH_2$—)N | H | H | Me | Me | CH | N | N | O |
| I-299 | COOH | Phenyl | (—$CH_2$—$CH_2$—$CH_2$—$CH_2$—$CH_2$—$CH_2$—)N | H | H | OMe | OMe | CH | N | N | O |
| I-300 | COOH | Phenyl | (—$CH_2$—$CH_2$—$CH_2$—$CH_2$—$CH_2$—$CH_2$—)N | H | H | OMe | Me | CH | N | N | S |
| I-301 | COOH | 4-F-Phenyl | (—$CH_2$—$CH_2$—$CH_2$—$CH_2$—$CH_2$—$CH_2$—)N | H | H | $CH_2OH$ | Me | CH | N | N | O |
| I-302 | COOH | Phenyl | (—$CH_2$—$CH_2$—$CH_2$—$CH_2$—$CH_2$—$CH_2$—)N | H | H | OMe | $CH_2$—$CH_2$—$CH_2$—C | N | N | O |
| I-303 | COOH | Phenyl | (—$CH_2$—$CH_2$—$CH_2$—$CH_2$—$CH_2$—$CH_2$—)N | Propyl | H | OMe | O—$CH_2$—$CH_2$—C | N | N | O |
| I-304 | COOH | Phenyl | (—$CH_2$—$CH_2$—$CH_2$—$CH_2$—$CH_2$—$CH_2$—)N | H | H | Ethyl | Ethyl | CH | N | N | O |
| I-305 | COOH | Phenyl | (—$CH_2$—$CH_2$—$CH_2$—$CH_2$—$CH_2$—$CH_2$—)N | H | H | $CF_3$ | Me | CH | N | N | O |
| I-306 | COOH | Phenyl | (—$CH_2$—$CH_2$—$CH_2$—$CH_2$—$CH_2$—$CH_2$—)N | H | H | OMe | $CF_3$ | CH | N | N | S |
| I-307 | COOH | Phenyl | tetrahydroisoquinolinyl | H | H | Me | Me | CH | N | N | O |
| I-308 | COOH | Phenyl | tetrahydroisoquinolinyl | H | H | OMe | OMe | CH | N | N | O |
| I-309 | COOH | Phenyl | tetrahydroisoquinolinyl | H | H | OMe | Me | CH | N | N | O |

TABLE I-continued

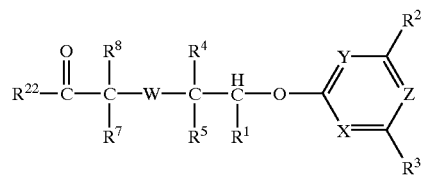

IA

| No. | R¹ | R⁴, R⁵ | R²² | R⁷ | R⁸ | R² | R³ | Z | X | Y | W |
|---|---|---|---|---|---|---|---|---|---|---|---|
| I-310 | COOH | Phenyl | tetrahydroisoquinolinyl | H | H | CH₂OH | Me | CH | N | N | S |
| I-311 | COOH | 4-F-Phenyl | tetrahydroisoquinolinyl | H | H | OMe | CH₂—CH₂—CH₂—C | N | N | O |
| I-312 | COOH | Phenyl | tetrahydroisoquinolinyl | Me | Me | OMe | O—CH₂—CH₂—C | N | N | O |
| I-313 | COOH | Phenyl | tetrahydroisoquinolinyl | H | H | Ethyl | Ethyl | CH | N | N | O |
| I-314 | COOH | Phenyl | tetrahydroisoquinolinyl | H | H | CF₃ | Me | CH | N | N | O |
| I-315 | COOH | Phenyl | tetrahydroisoquinolinyl | H | H | OMe | CF₃ | CH | N | N | O |
| I-316 | COOH | Phenyl | isoindolinyl | H | H | Me | Me | CH | N | N | O |
| I-317 | COOH | 4-F-Phenyl | isoindolinyl | H | H | OMe | OMe | CH | N | N | O |
| I-318 | COOH | Phenyl | isoindolinyl | H | H | OMe | Me | CH | N | N | O |
| I-319 | COOH | Phenyl | isoindolinyl | Ethyl | H | CH₂OH | Me | CH | N | N | O |
| I-320 | COOH | Phenyl | isoindolinyl | H | H | OMe | CH₂—CH₂—CH₂—C | N | N | S |
| I-321 | COOH | Phenyl | isoindolinyl | H | H | OMe | O—CH₂—CH₂—C | N | N | O |

TABLE I-continued

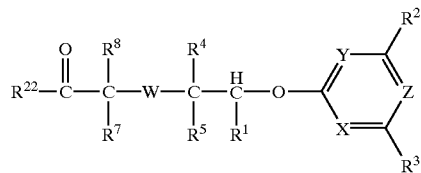

| No. | R¹ | R⁴, R⁵ | R²² | R⁷ | R⁸ | R² | R³ | Z | X | Y | W |
|---|---|---|---|---|---|---|---|---|---|---|---|
| I-322 | COOH | Phenyl |  | H | H | Ethyl | Ethyl | CH | N | N | O |
| I-323 | COOH | Phenyl |  | H | H | CF₃ | Me | CH | N | N | O |
| I-324 | COOH | Phenyl |  | H | H | OMe | CF₃ | CH | N | N | O |
| I-325 | COOH | Phenyl | (N-2,6-Diethylphenyl-N-Ethoxymethylene)—N | H | H | Me | Me | CH | N | N | O |
| I-326 | COOH | Phenyl | (N-2,6-Diethylphenyl-N-Ethoxymethylene)—N | H | H | OMe | OMe | CH | N | N | O |
| I-327 | COOH | Phenyl | (N-2,6-Diethylphenyl-N-Ethoxymethylene)—N [sic] | H | H | OMe | Me | CH | N | N | O |
| I-328 | COOH | Phenyl | (N-2,6-Diethylphenyl-N-Ethoxymethylene)—N [sic] | H | H | CH₂OH | Me | CH | N | N | O |
| I-329 | COOH | Phenyl | (N-2,6-Diethylphenyl-N-Ethoxymethylene)—N [sic] | H | H | OMe | CH₂—CH₂—CH₂—C | N | N | O |
| I-330 | COOH | Phenyl | (N-2,6-Diethylphenyl-N-Ethoxymethylene)—N [sic] | H | H | OMe | O—CH₂—CH₂—C | N | N | O |
| I-331 | COOH | 4-F-Phenyl | (N-2,6-Diethylphenyl-N-Ethoxymethylene)—N [sic] | H | H | Ethyl | Ethyl | CH | N | N | S |
| I-332 | COOH | Phenyl | (N-2,6-Diethylphenyl-N-Ethoxymethylene)—N [sic] | H | H | CF₃ | Me | CH | N | N | O |
| I-333 | COOH | Phenyl | (N-2,6-Diethylphenyl-N-Ethoxymethylene)—N [sic] | H | H | OMe | CF₃ | CH | N | N | O |
| I-334 | COOH | Phenyl | (N-2,6-Diisopropylphenyl-N-Methoxy-methylene)—N [sic] | H | H | Me | Me | CH | N | N | O |
| I-335 | COOH | Phenyl | (N-2,6-Diisopropylphenyl-N-Methoxy-methylene)—N [sic] | H | H | OMe | OMe | CH | N | N | O |
| I-336 | COOH | Phenyl | (N-2,6-Diisopropylphenyl-N-Methoxy-methylene)—N [sic] | Me | Me | OMe | Me | CH | N | N | O |
| I-337 | COOH | Phenyl | (N-2,6-Diisopropylphenyl-N-Methoxy-methylene)—N [sic] | H | H | CH₂OH | Me | CH | N | N | S |
| I-338 | COOH | 4-F-Phenyl | (N-2,6-Diisopropylphenyl-N-Methoxy-methylene)—N [sic] | H | H | OMe | CH₂—CH₂—CH₂—C | N | N | O |
| I-339 | COOH | Phenyl | (N-2,6-Diisopropylphenyl-N-Methoxy-methylene)—N [sic] | H | H | OMe | O—CH₂—CH₂—C | N | N | O |
| I-340 | COOH | Phenyl | (N-2,6-Diisopropylphenyl-N-Methoxy-methylene)—N [sic] | H | H | Ethyl | Ethyl | CH | N | N | O |
| I-341 | COOH | Phenyl | (N-2,6-Diisopropylphenyl-N-Methoxy-methylene)—N [sic] | H | H | CF₃ | Me | CH | N | N | O |
| I-342 | COOH | Phenyl |  | H | H | Me | Me | CH | N | N | O |
| I-343 | COOH | Phenyl |  | H | H | OMe | OMe | CH | N | N | O |
| I-344 | COOH | Phenyl |  | H | H | OMe | Me | CH | N | N | O |

TABLE I-continued

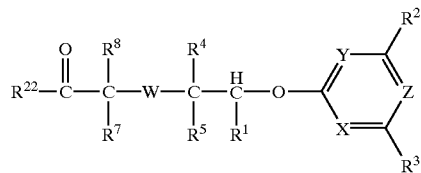

IA

| No. | R¹ | R⁴, R⁵ | R²² | R⁷ | R⁸ | R² | R³ | Z | X | Y | W |
|---|---|---|---|---|---|---|---|---|---|---|---|
| I-345 | COOH | Phenyl | (morpholine-N) | H | CH₂OH | Me | CH | N | N | S | |
| I-346 | COOH | Phenyl | (morpholine-N) | H | H | OMe | CH₂—CH₂—CH₂—C | N | N | O | |
| I-347 | COOH | Phenyl | Bu₂N | H | H | Me | Me | CH | N | N | O |
| I-348 | COOH | Phenyl | Bu₂N | Me | H | OMe | OMe | CH | N | N | S |
| I-349 | COOH | Phenyl | Bu₂N | H | H | OMe | Me | CH | N | N | O |
| I-350 | COOH | Phenyl | Bu₂N | Butyl | H | CH₂OH | Me | CH | N | N | O |
| I-351 | COOH | Phenyl | Bu₂N | H | H | OMe | CH₂—CH₂—CH₂—C | N | N | O | |
| I-352 | COOH | Phenyl | Bu₂N | H | H | OMe | O—CH₂—CH₂—C | N | N | O | |
| I-353 | COOH | Phenyl | Bu₂N | H | H | Ethyl | Ethyl | CH | N | N | O |
| I-354 | COOH | 4-F-Phenyl | Bu₂N | H | H | CF₃ | Me | CH | N | N | S |
| I-355 | COOH | Phenyl, 4 Cl-Phenyl | Me₂N | Me | Me | Me | Me | CH | N | N | O |
| I-356 | COOH | 4-Cl-Phenyl, 4-F-Phenyl | Phenyl-HN | H | H | OMe | OMe | CH | N | N | S |
| I-357 | COOH | 4-F-Phenyl, Phenyl | (N-Butyl-N—Me)—N | H | H | OMe | Me | CH | N | N | O |
| I-358 | COOH | 4-Me-Phenyl-, Naphthyl | (N-Phenyl-N—Me)—N | H | H | CH₂OH | Me | CH | N | N | O |
| I-359 | COOMe | 2-F-Phenyl, Phenyl | (4-Chlorophenyl)—HN | H | H | OMe | CH₂—CH₂—CH₂—C | N | N | O | |
| I-360 | COOH | 2-F-Phenyl, 4-Me-Phenyl- | (2,6-Dimethoxyphenyl)—HN | H | H | OMe | O—CH₂—CH₂—C | N | N | O | |
| I-361 | COOH | Naphthyl, Phenyl | (2,6-Diethylphenyl)—HN | H | H | Ethyl | Ethyl | CH | N | N | O |
| I-362 | COOH | Phenyl, 4 Cl Phenyl | H | H | CF₃ | Me | CH | N | N | N | S |
| I-363 | COOH | 4-Cl-Phenyl, 4-F-Phenyl | H | H | OMe | CF₃ | CH | N | N | N | O |
| I-364 | COOH | Naphthyl, Me₂N | Me | Me | Me | Me | CH | N | N | O | |
| I-365 | COOH | Naphthyl, Naphthyl | Phenyl-HN | H | H | OMe | OMe | CH | N | N | S |
| I-366 | COOH | 4-F-Phenyl, 4 Cl Phenyl | (N-Butyl-N—Me)—N | H | H | OMe | Me | CH | N | N | O |
| I-367 | COOH | 4-F-Phenyl, Phenyl | Bu₂N | H | H | Me | Me | CH | N | N | O |

TABLE II

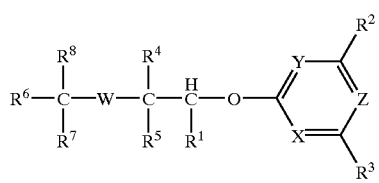

I

| No. | R¹ | R⁴, R⁵ | R⁶ | R⁷ | R⁸ | R² | R³ | Z | X | Y | W |
|---|---|---|---|---|---|---|---|---|---|---|---|
| II-1 | COOH | Phenyl | (N-(2-OMe-PhenylCO)-N-Propyl)-N—CH₂— | H | H | Me | Me | CH | N | N | O |
| II-2 | COOH | Phenyl | (N-PhenylSO₂-N-Propyl)-N—CH₂— | H | H | OMe | Me | CH | N | N | O |
| II-3 | COOH | Phenyl | (N-PhenylSO₂-N-Propyl)-N—CH₂— | H | H | OMe | OMe | CF | N | N | O |
| II-4 | COOMe | Phenyl | (N-PhenylSO₂-N-Me)-N—CH₂— | H | H | OMe | CH₂—CH₂—CH₂—C | N | N | O |

TABLE II-continued

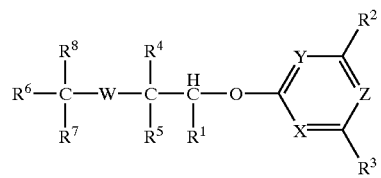

| No. | R¹ | R⁴, R⁵ | R⁶ | R⁷ | R⁸ | R² | R³ | Z | X | Y | W |
|---|---|---|---|---|---|---|---|---|---|---|---|
| II-5 | COOH | Phenyl | (N-PhenylSO₂-N-Me)-N—CH₂— | H | H | OMe | O—CH₂—CH₂—C | N | N | O |
| II-6 | COOH | Phenyl | (N-PhenylSO₂-N-Me)-N—CH₂— | H | H | Ethyl | Ethyl | CH | N | N | O |
| II-7 | COOH | Phenyl | (N-PhenylSO₂-N-Me)-N—CH₂— | H | H | CF₃ | Me | CH | N | N | S |
| II-8 | COOH | Phenyl | (N-PhenylSO₂-N-Me)-N—CH₂— | H | H | OMe | CF₃ | CH | N | N | O |
| II-9 | COOH | Phenyl, 4 Cl Phenyl | (MeCO-N-Me)-N—CH₂— | Me | Me | Me | Me | CH | N | N | O |
| II-10 | COOH | Phenyl | (N-PhenylCO-N-Butyl)-N—CH₂— | H | H | Me | Me | CH | N | N | O |
| II-11 | COOH | Phenyl | (N-PhenylCO-N-Propyl)-N—CH₂— | Me | H | OMe | OMe | CH | N | N | S |
| II-12 | COOH | Phenyl | (N-PhenylCO-N-Propyl)-N—CH₂— | H | H | OMe | Me | CH | N | N | O |
| II-13 | COOH | Phenyl | (N-PhenylCO-N-Me)-N—CH₂— | Butyl | H | CH₂OH | Me | CH | N | N | O |
| II-14 | COOH | Phenyl | (N-PhenylCO-N-Me)-N—CH₂— | H | H | OMe | CH₂—CH₂—CH₂—C | N | N | O |
| II-15 | COOH | 4-Cl-Phenyl, 4-F-Phenyl | (N-PhenylSO₂-N-Me)-N—CH₂— | H | H | OMe | OMe | CH | N | N | S |
| II-16 | COOH | Phenyl | (N-PhenylCO-N-Me)-N—CH₂— | H | H | OMe | O—CH₂—CH₂—C | N | N | O |
| II-17 | COOH | Phenyl | (N-PhenylCO-N-Me)-N—CH₂— | H | H | Ethyl | Ethyl | CH | N | N | O |
| II-18 | COOH | 4-F-Phenyl | (N-(4-OMe-Phenyl)-N-Butyl)-N—CH₂— | H | H | CF₃ | Me | CH | N | N | S |
| II-19 | COOH | Phenyl | (N-(3-OMe-PhenylCO)-N-Propyl)-N—CH₂— | H | H | OMe | CF₃ | CH | N | N | O |
| II-20 | COOH | Phenyl | (N-PhenylSO₂-N-Butyl)-N—CH₂— | H | H | Me | Me | CH | N | N | O |
| II-21 | COOH | Phenyl | (N-(3,4-Di-OMe-PhenylCO)-N-Me)-N—CH₂— | H | H | OMe | OMe | CH | N | N | S |
| II-22 | COOH | Phenyl | (N-(3,4-Di-OMe-PhenylCO)-N-Me)-N—CH₂— | H | H | OMe | Me | CH | N | N | O |
| II-23 | COOH | Phenyl | (N-(3,4-Di-OMe-PhenylCO)-N-Me)-N—CH₂— | H | H | CH₂OH | Me | CH | N | N | O |
| II-24 | COOH | 4-F-Phenyl | (N-(3,4-Di-OMe-PhenylCO)-N-Me)-N—CH₂— | Me | Me | OMe | CH₂—CH₂—CH₂—C | N | N | O |
| II-25 | COOH | Phenyl | (N-(3,4-Di-OMe-PhenylCO)-N-Me)-N—CH₂— | H | H | OMe | O—CH₂—CH₂—C | N | N | O |
| II-26 | COOH | Phenyl | (N-(2,6-Di-OMe-PhenylCO)-N-Me)-N—CH₂— | H | H | Ethyl | Ethyl | CH | N | N | S |
| II-27 | COOH | 4-F-Phenyl | (N-(2,6-Di-OMe-PhenylCO)-N-Me)-N—CH₂— | H | H | CF₃ | Me | CH | N | N | O |
| II-28 | COOH | 4-F-Phenyl | (N-(2,6-Di-OMe-PhenylCO)-N-Me)-N—CH₂— | H | H | OMe | CF₃ | CH | N | N | O |
| II-29 | COOH | Phenyl | (N-(2,6-Di-OMe-PhenylCO)-N-Me)-N—CH₂— | H | H | Me | Me | N | CH | N | O |
| II-30 | COOH | Phenyl | (N-(2,6-Di-OMe-PhenylCO)-N-Me)-N—CH₂— | H | H | OMe | OMe | CF | N | N | O |
| II-31 | COOH | Phenyl | (N-(2,6-Di-OMe-PhenylCO)-N-Me)-N—CH₂— | H | H | OMe | Me | CH | N | N | O |
| II-32 | COOH | Phenyl | Phenyl-CH₂—O—CO—HN—CH₂— | H | H | Me | Me | CH | N | N | O |
| II-33 | COOH | 4-F-Phenyl, Phenyl | (N-(3-OMe-PhenylCO)-N-Propyl)-N—CH₂— | H | H | OMe | Me | CH | N | N | O |
| II-34 | COOMe | Phenyl | 2,6-Di-OMe-PhenylCO-HN—CH₂— | H | H | CH₂OH | Me | CH | N | N | O |
| II-35 | COOH | Phenyl | 2,6-Di-OMe-PhenylCO-HN—CH₂— | H | H | OMe | CH₂—CH₂—CH₂—C | N | N | O |
| II-36 | COOH | Phenyl | 2,6-Di-OMe-PhenylCO-HN—CH₂— | Me | Me | OMe | O—CH₂—CH₂—C | N | N | O |
| II-37 | COOH | Phenyl | 2,6-Di-OMe-PhenylCO-HN—CH₂— | H | H | Ethyl | Ethyl | CH | N | N | S |
| II-38 | COOH | Phenyl | 2,5-Di-OMe-PhenylCO-HN—CH₂— | H | H | CF₃ | Me | CH | N | N | O |
| II-39 | COOH | 4-F-Phenyl | 2,4-Di-OMe-PhenylCO-HN—CH(Me)— | H | H | OMe | CF₃ | CH | N | N | O |
| II-40 | COOH | Phenyl | 2,3-Di-Me-PhenylCO-HN—CH₂— | H | H | Me | Me | CF | N | N | O |
| II-41 | COOH | Phenyl | 2,3-Di-Me-PhenylCO-HN—CH₂— | H | H | OMe | OMe | CH | N | N | S |
| II-42 | COOH | 4-Me-Phenyl, Naphthyl | (N-PhenylCO-N-Butyl)-N—CH₂— | H | H | CH₂OH | Me | CH | N | N | O |
| II-43 | COOH | Phenyl | 3,4-Di-Me-PhenylCO-HN—CH₂— | H | H | OMe | Me | CH | N | N | O |
| II-44 | COOH | 4-F-Phenyl | 3,5-Di-Me-PhenylCO-HN—CH₂— | H | H | CH₂OH | Me | CH | N | N | O |
| II-45 | COOH | Phenyl | 3,4-Di-OMe-PhenylCO-HN—CH₂— | H | H | OMe | CH₂—CH₂—CH₂—C | N | N | O |
| II-46 | COOH | Phenyl | (N-PhenylSO₂-N-Propyl)-N—CH₂— | H | H | OMe | O—CH₂—CH₂—C | N | N | S |
| II-47 | COOH | Phenyl | (N-PhenylSO₂-N-Propyl)-N—CH₂— | H | H | Ethyl | Ethyl | CH | N | N | O |
| II-48 | COOH | Phenyl | (N-PhenylSO₂-N-Propyl)-N—CH₂— | H | H | Me | Me | CH | N | N | O |
| II-49 | COOH | Phenyl | (N-PhenylSO₂-N-Propyl)-N—CH₂— | H | H | CF₃ | Me | CH | N | N | O |
| II-50 | COOH | Phenyl | (N-PhenylSO₂-N-Ethyl)-N—CH₂— | Ethyl | H | OMe | CF₃ | CH | N | N | O |
| II-51 | COOH | Phenyl | (N-PhenylSO₂-N-Ethyl)-N—CH₂— | H | H | Me | Me | CH | N | N | O |
| II-52 | COOH | Phenyl | (N-PhenylSO₂-N-Ethyl)-N—CH₂— | H | H | H | OMe | CH | N | N | O |
| II-53 | COOH | Phenyl | (N-PhenylSO₂-N-Ethyl)-N—CH(Me)— | Me | H | OMe | Me | CH | N | N | O |
| II-54 | COOH | Phenyl | (N-PhenylSO₂-N-Ethyl)-N—CH₂— | H | H | CH₂F | Me | CH | N | N | S |
| II-55 | COOH | Phenyl | (N-(3-OMe-4-Me-PhenylSO₂)-N-Ethyl)-N—CH₂— | H | H | OMe | CH₂—CH₂—CH₂—C | N | N | O |
| II-56 | COOMe | Phenyl | (N-(3-Cl-4-Me-PhenylSO₂)-N-Ethyl)-N—CH₂— | H | H | OMe | O—CH₂—CH₂—C | N | N | O |
| II-57 | COOH | Phenyl | (N-(3-OMe-4-Me-PhenylSO₂)-N-Ethyl)-N—CH₂— | H | H | Ethyl | Ethyl | CH | N | N | O |
| II-58 | COOH | Phenyl | (N-(3-OMe-4-Me-PhenylSO₂)-N-Ethyl)-N—CH₂— | H | H | CF₃ | Me | CH | N | N | O |
| II-59 | COOH | 4-F-Phenyl | (N-(3-Cl-4-Me-PhenylSO₂)-N-Ethyl)-N—CH₂— | H | H | OMe | CF₃ | CH | N | N | O |
| II-60 | COOH | Phenyl | (N-(3-Cl-4-Me-PhenylSO₂)-N-Ethyl)-N—CH₂— | H | H | Me | Me | CH | N | N | O |
| II-61 | COOH | Phenyl | (N-(3,4-Di-Cl-PhenylSO₂)-N-Ethyl)-N—CH₂— | H | H | OMe | OMe | CH | N | N | S |
| II-62 | COOH | Phenyl | 3,4-Di-OMe-PhenylCO-HN—CH₂— | H | H | Me | Me | CH | N | N | O |
| II-63 | COOH | Phenyl | (N-(3,4-Di-Cl-PhenylSO₂)-N-Ethyl)-N—CH₂— | H | H | OMe | Me | CH | N | N | O |
| II-64 | COOH | Phenyl | (N-(3,4-Di-Cl-PhenylSO₂)-N-Ethyl)-N—CH₂— | H | H | H | Me | C—Me | N | N | O |
| II-65 | COOH | 4-F-Phenyl | (N-(2,6-Di-OMe-PhenylSO₂)-N-Ethyl)-N—CH₂— | H | H | OMe | CH₂—CH₂—CH₂—C | N | N | O |

TABLE II-continued

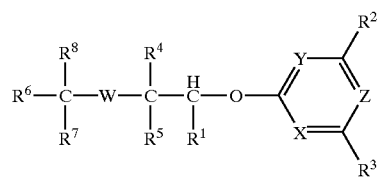

| No. | R¹ | R⁴, R⁵ | R⁶ | R⁷ | R⁸ | R² | R³ | Z | X | Y | W |
|---|---|---|---|---|---|---|---|---|---|---|---|
| II-66 | COOH | Phenyl | (N-(2,6-Di-OMe-PhenylSO₂)-N-Ethyl)-N—CH₂— | Me | Me | OMe | O—CH₂—CH₂—C | N | N | O |
| II-67 | COOMe | 2-F-Phenyl, Phenyl | (N-(3-Cl-4-Me-PhenylSO₂)-N-Ethyl)-N—CH₂— | H | H | OMe | CH₂—CH₂—CH₂—C | N | N | O |
| II-68 | COOH | Phenyl | (N-(2,6-Di-OMe-PhenylSO₂)-N-Ethyl)-N—CH₂— | H | H | Ethyl | Ethyl | N | CH | N | O |
| II-69 | COOH | Phenyl | (N-(3-OMe-4-Me-PhenylSO₂)-N-Me)-N—CH₂— | Me | Me | CF₃ | Me | CH | N | N | O |
| II-70 | COOH | Phenyl | (N-(3-Cl-4-Me-PhenylSO₂)-N-Me)-N—CH₂— | H | H | OMe | CF₃ | CH | N | N | O |
| II-71 | COOH | Phenyl | (N-(3-OMe-4-Me-PhenylSO₂)-N-Me)-N—CH₂— | H | H | Me | Me | CH | N | N | O |
| II-72 | COOH | Phenyl | (N-(3-OMe-4-Me-PhenylSO₂)-N-Me)-N—CH₂— | H | H | OMe | OMe | CH | N | N | O |
| II-73 | COOH | Phenyl | (N-(3-Cl-4-Me-PhenylSO₂)-N-Me)-N—CH₂— | Me | H | OMe | Me | CH | N | N | O |
| II-74 | COOH | Phenyl | (N-(3-Cl-4-Me-PhenylSO₂)-N-Me)-N—CH₂— | H | H | H | OMe | C—Me | N | N | O |
| II-75 | COOH | Phenyl | (N-(3,4-Di-Cl-PhenylSO₂)-N-Me)-N—CH₂— | H | H | OMe | CH₂—CH₂—CH₂—C | N | N | O |
| II-76 | COOH | 4-F-Phenyl | (N-(3,4-Di-Cl-PhenylSO₂)-N-Me)-N—CH₂— | H | H | OMe | O—CH₂—CH₂—C | N | N | S |
| II-77 | COOH | Phenyl | (N-(2,6-Di-OMe-PhenylSO₂)-N-Me)-N—CH₂— | H | H | Ethyl | Ethyl | CH | N | N | O |
| II-78 | COOH | Phenyl | (N-(3,4-Di-OMe-Phenyl-CO)-N-Me)-N—CH₂— | H | H | Me | Me | CH | N | N | O |
| II-79 | COOH | Phenyl | (N-(2,6-Di-OMe-PhenylSO₂)-N-Me)-N—CH₂— | H | H | CF₃ | Me | CH | N | N | O |
| II-80 | COOH | Phenyl | (N-(2,6-Di-OMe-PhenylSO₂)-N-Me)-N—CH₂— | H | H | OMe | CF₃ | CH | N | N | O |
| II-81 | COOH | Phenyl | PhenylSO₂-HN—CH(Benzyl)— | H | H | Me | Me | CH | N | N | O |
| II-82 | COOH | Phenyl | PhenylSO₂-HN—CH₂— | Me | Me | OMe | OMe | CH | N | N | O |
| II-83 | COOH | 2-F-Phenyl, 4-Me-Phenyl | 3-HOOCCH₂O-4-OMe-PhenylCO-HN—CH₂— | H | H | OMe | O—CH₂—CH₂—C | N | N | O |
| II-84 | COOH | Phenyl | PhenylSO₂-HN—CH₂— | H | H | OMe | Me | CH | N | N | O |
| II-85 | COOH | 4-F-Phenyl | PhenylSO₂-HN—CH₂— | H | H | H | OMe | C—OMe | N | N | O |
| II-86 | COOH | Phenyl | PhenylSO₂-HN—CH₂— | H | H | OMe | CH₂—CH₂—CH₂—C | N | N | S |
| II-87 | COOH | Phenyl | (N-ButylSO₂-N-Me)-N—CH₂— | H | H | OMe | O—CH₂—CH₂—C | N | N | O |
| II-88 | COOH | Phenyl | (N-(2,6-Di-OMe-Phenyl-CO)-N-Me)-N—CH₂— | H | H | Me | Me | CH | N | N | O |
| II-89 | COOH | Phenyl | (N-ButylSO₂-N-Me)-N—CH₂— | H | H | Ethyl | Ethyl | CH | N | N | O |
| II-90 | COOH | Phenyl | (N-ButylSO₂-N-Me)-N—CH₂— | H | H | CF₃ | Me | CH | N | N | O |
| II-91 | COOH | Phenyl | (N-MeSO₂-N-Me)-N—CH₂— | H | H | OMe | CF₃ | CH | N | N | S |
| II-92 | COOMe | Phenyl | (N-MeSO₂-N-Me)-N—CH₂— | H | H | Me | Me | CH | N | N | O |
| II-93 | COOH | Phenyl | (N-MeSO₂-N-Me)-N-CH(iso-Propyl)— | H | H | OMe | OMe | CH | N | N | O |
| II-94 | COOH | 4-F-Phenyl | (N-MeSO₂-N-Me)-N—CH₂— | H | H | OMe | Me | CH | N | N | O |
| II-95 | COOH | Phenyl | (N-MeSO₂-N-Me)-N—CH₂— | Me | Me | H | Me | CH | N | N | O |
| II-96 | COOH | Phenyl | (N-MeSO₂-N-Ethyl)-N—CH₂— | H | H | OMe | CH₂—CH₂—CH₂—C | N | N | O |
| II-97 | COOH | Naphthyl, Phenyl | 2,3-Di-Me-PhenylCO-HN—CH₂— | H | H | Ethyl | Ethyl | CH | N | N | O |
| II-98 | COOH | Phenyl | (N-MeSO₂-N-Ethyl)-N—CH₂— | H | H | OMe | O—CH₂—CH₂—C | N | N | O |
| II-99 | COOH | Phenyl | (N-MeSO₂-N-Ethyl)-N—CH₂— | Et | H | Ethyl | Ethyl | CH | N | N | O |
| II-100 | COOH | Phenyl | (N-MeSO₂-N-Ethyl)-N—CH₂— | H | H | CF₃ | Me | CH | N | N | O |
| II-101 | Tetrazole [sic] | Phenyl | (N-MeSO₂-N-Ethyl)-N—CH₂— | H | H | Me | Me | CH | N | N | O |
| II-102 | COOH | Phenyl | (N-ButylSO₂-N-Propyl)-N—CH₂— | H | H | Me | Me | CH | N | N | O |
| II-103 | COOH | 4-F-Phenyl | (N-PhenylCO-N-Ethyl)-N—CH₂— | H | H | OMe | OMe | CH | N | N | O |
| II-104 | COOH | Phenyl | (N-PhenylCO-N-Ethyl)-N—CH₂— | H | H | OMe | Me | CH | N | N | O |
| II-105 | COOH | Phenyl | (N-(4-OMe-PhenylCO)-N-Ethyl)-N—CH₂— | H | H | Me | Me | CF | N | N | O |
| II-106 | COOH | Phenyl | (N-MeCO-N-(4-OMe-3-Me-Phenyl))-N—CH₂— | H | H | OMe | CH₂—CH₂—CH₂—C | N | N | O |
| II-107 | COOH | Phenyl | (N-(3-OMe-PhenylCO)-N-Ethyl)-N—CH₂— | Et | H | OMe | CH₂—CH₂—CH₂—C | N | N | O |
| II-108 | COOMe | Phenyl | (N-(2-OMe-PhenylCO)-N-Ethyl)-N—CH₂— | H | H | OMe | O—CH₂—CH₂—C | N | N | S |
| II-109 | COOH | Phenyl | (N-(3,4-Di-OMe-PhenylCO)-N-Ethyl)-N—CH₂— | H | H | Ethyl | Ethyl | CH | N | N | O |
| II-110 | COOH | Phenyl | (N-(3,4-Di-OMe-PhenylCO)-N-Ethyl)-N—CH₂— | H | H | CF₃ | Me | CH | N | N | S |
| II-111 | COOH | Phenyl | (N-(3,4-Di-OMe-PhenylCO)-N-Ethyl)-N—CH₂— | Me | Me | OMe | CF₃ | CH | N | N | O |
| II-112 | COOH | Phenyl | (N-(3-H₂NCOCH₂-PhenylCO)-N-Me)-N—CH₂— | H | H | Me | Me | CH | N | N | O |
| II-113 | COOH | Phenyl | (N-(3-H₂NCOCH₂-PhenylCO)-N-Me)-N—CH₂— | H | H | OMe | OMe | CH | N | N | O |
| II-114 | COOH | 4-F-Phenyl | (N-(3-H₂NCOCH₂-4-Me-PhenylCO)-N-Me)-N—CH₂— | H | H | OMe | Me | CH | N | N | O |
| II-115 | COOH | Phenyl | 3,4-Di-Cl-PhenylCO-HN—CH₂— | H | H | Me | Me | CH | N | N | O |
| II-116 | COOH | Phenyl | (N-(3-H₂NCOCH₂-4-Me-PhenylCO)-N-Me)-N—CH₂— | H | H | H | OMe | C—Me | N | N | O |
| II-117 | COOH | Phenyl | (N-(3-HOOCCH₂-4-OMe-PhenylCO)-N-Me)-N—CH₂— | Butyl | H | OMe | CH₂—CH₂—CH₂—C | N | N | O |
| II-118 | COOH | Phenyl | Me-CH=CH—CO—HN—CH₂— | H | H | Me | Me | CH | N | N | O |
| II-119 | COOH | Phenyl | (N-(3-HOOCCH₂-4-OMe-PhenylCO)-N-Me)-N—CH₂— | H | H | OMe | O—CH₂—CH₂—C | N | N | S |
| II-120 | COOH | Phenyl | (N-(3-HOOCCH₂-4-Cl-PhenylCO)-N-Me)-N—CH₂— | H | H | Ethyl | Ethyl | CH | N | N | O |
| II-121 | COOH | 4-F-Phenyl | (N-(3-HOOCCH₂-4-Cl-PhenylCO)-N-Me)-N—CH₂— | H | H | CF₃ | Me | CH | N | N | O |
| II-122 | COOH | Phenyl | 2,6-Di-OMe-PhenylCO-HN—CH₂— | H | H | Me | Me | CH | N | N | O |
| II-123 | COOH | Phenyl | 3-HOOCCH₂-4-Cl-PhenylCO-HN—CH₂— | H | H | OMe | CF₃ | CH | N | N | O |

TABLE II-continued

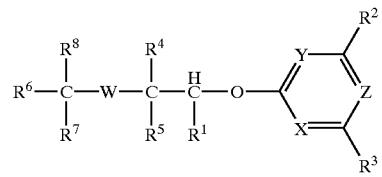

| No. | $R^1$ | $R^4, R^5$ | $R^6$ | $R^7$ | $R^8$ | $R^2$ | $R^3$ | Z | X | Y | W |
|---|---|---|---|---|---|---|---|---|---|---|---|
| II-124 | COOH | Phenyl | 3-HOOCCH$_2$-4-Cl-PhenylCO-HN—CH$_2$— | H | H | Me | Me | CH | N | N | O |
| II-125 | COOH | Phenyl | 3-HOOCCH$_2$-4-Cl-PhenylCO-HN—CH$_2$— | H | H | OMe | OMe | CH | N | N | O |
| II-126 | COOH | Phenyl | 3-HOOCCH$_2$O-4-OMe-PhenylCO-HN—CH$_2$— | H | H | OMe | Me | CH | N | N | O |
| II-127 | COOH | Phenyl | 3-HOOCCH$_2$O-4-OMe-PhenylCO-HN—CH$_2$— | Ethyl | H | OMe | OMe | CH | N | N | O |
| II-128 | COOH | 4-F-Phenyl | 3-HOOCCH$_2$O-4-OMe-PhenylCO-HN—CH$_2$— | H | H | OMe | CH$_2$—CH$_2$—CH$_2$—C | N | N | O |
| II-129 | COOH | Phenyl | (N-MeCO-N-(4-OMe-3-Me-Phenyl))-N—CH$_2$— | H | H | Me | Me | CH | N | N | O |
| II-130 | COOH | Phenyl | 3-HOOCCH$_2$O-4-OMe-PhenylCO-HN—CH$_2$— | H | H | OMe | O—CH$_2$—CH$_2$—C | N | N | S |
| II-131 | COOH | Naphthyl, Naphthyl | 2,6-DiethylphenylCO-HN—CH$_2$— | Me | Me | Me | Me | CH | N | N | O |
| II-132 | COOH | Phenyl | 3-HOOCCH$_2$O-4-OMe-PhenylCO-HN—CH$_2$— | Ethyl | H | Ethyl | Ethyl | CH | N | N | O |
| II-133 | COOH | Phenyl | 3-MeOOCCH$_2$O-4-OMe-PhenylCO-HN—CH$_2$— | H | H | CF$_3$ | Me | CH | N | N | O |
| II-134 | COOH | Phenyl | 3-MeOOCCH$_2$O-4-OMe-PhenylCO-HN—CH$_2$— | H | H | OMe | CF$_3$ | CH | N | N | O |
| II-135 | COOH | Phenyl | 3-MeOOCCH$_2$O-4-OMe-PhenylCO-HN—CH$_2$— | H | H | Me | Me | CH | N | N | O |
| II-136 | COOH | Phenyl | Me-CH=CH—CO—HN—CH$_2$— | H | H | OMe | CF$_3$ | CH | N | N | O |
| II-137 | COOH | Phenyl | 4-MeOOCCH$_2$O-3-OMe-PhenylCO-HN—CH$_2$— | H | H | OMe | OMe | CH | N | N | O |
| II-138 | COOH | Phenyl | 4-MeOOCCH$_2$O-3-OMe-PhenylCO-HN—CH$_2$— | H | H | OMe | Me | CH | N | N | S |
| II-139 | COOH | Phenyl | 4-MeOOCCH$_2$O-3-OMe-PhenylCO-HN—CH$_2$— | Me | Me | Ethyl | Me | N | CH | N | O |
| II-140 | COOH | Phenyl | (N-(4-OMe-Phenyl-CH$_2$—CO)-N-Butyl)-N—CH$_2$— | H | H | OMe | CH$_2$—CH$_2$—CH$_2$—C | N | N | O |
| II-141 | COOH | Phenyl | (N-EthylCO-N-(4-OMe-Phenyl))-N—CH$_2$— | H | H | OMe | CF$_3$ | CH | N | N | O |
| II-142 | COOH | Phenyl | (N-(3-OMe-Phenyl-CH$_2$—CO)-N-Propyl)-N—CH$_2$— | H | H | OMe | O—CH$_2$—CH$_2$—C | N | N | S |
| II-143 | COOMe | 4-F-Phenyl | (N-(2-OMe-Phenyl-CH$_2$—CO)-N-Propyl)-N—CH$_2$— | H | H | Ethyl | Ethyl | CH | N | N | O |
| II-144 | COOH | Phenyl | (N-(3,4-Di-OMe-Phenyl-CH$_2$—CO)-N-Me)-N—CH$_2$— | H | H | CF$_3$ | Me | CH | N | N | O |
| II-145 | COOH | Phenyl | (N-(3,4-Di-OMe-Phenyl-CH$_2$—CO)-N-Me)-N—CH$_2$— | H | H | OMe | CF$_3$ | CH | N | N | O |
| II-146 | COOH | Phenyl | (N-(3,4-Di-OMe-Phenyl-CH$_2$—CO)-N-Me)-N—CH$_2$— | H | H | Me | Me | CH | N | N | O |
| II-147 | COOH | Phenyl | (N-(3,4-Di-OMe-Phenyl-CH$_2$—CO)-N-Me)-N—CH$_2$— | H | H | OMe | OMe | CH | N | N | O |
| II-148 | COOH | Phenyl | (N-(3,4-Di-OMe-Phenyl-CH$_2$—CO)-N-Me)-N—CH$_2$— | H | H | OMe | Me | CH | N | N | O |
| II-149 | COOH | Phenyl | (N-(2,6-Di-OMe-Phenyl-CH$_2$—CO)-N-Me)-N—CH$_2$— | Me | Me | CH$_2$OH | Me | CH | N | N | O |
| II-150 | COOH | 4-F-Phenyl | (N-(2,6-Di-OMe-Phenyl-CH$_2$—CO)-N-Me)-N—CH$_2$— | H | H | OMe | CH$_2$—CH$_2$—CH$_2$—C | N | N | O |
| II-151 | COOH | Phenyl | (N-MeCO-N-(4-Cl-Phenyl))-N—CH$_2$— | H | H | CF$_3$ | Me | CH | N | N | O |
| II-152 | COOH | Phenyl | (N-(2,6-Di-OMe-Phenyl-CH$_2$—CO)-N-Me)-N—CH$_2$— | H | H | OMe | O—CH$_2$—CH$_2$—C | N | N | S |
| II-153 | COOH | Phenyl | (N-(2,6-Di-OMe-Phenyl-CH$_2$—CO)-N-Me)-N—CH$_2$— | H | H | Ethyl | Ethyl | CH | N | N | O |
| II-154 | COOH | 4-F-Phenyl | (N-(2,6-Di-OMe-Phenyl-CH$_2$—CO)-N-Me)-N—CH$_2$— | H | H | CF$_3$ | Me | CH | N | N | O |
| II-155 | COOH | Phenyl | (N-(2,6-Di-OMe-Phenyl-CH$_2$—CO)-N-Me)-N—CH$_2$— | H | H | OMe | CF$_3$ | CH | N | N | O |
| II-156 | COOMe | Phenyl | (N-(3,4-Di-OMe-PhenylCO)-N-Benzyl)-N—CH$_2$— | H | H | Me | Me | CH | N | N | O |
| II-157 | COOH | Phenyl | Iso-PropylCO-HN—CH$_2$— | H | H | CF$_3$ | Me | CH | N | N | O |
| II-158 | COOH | Phenyl | (N-(3,4-Di-OMe-PhenylCO)-N-Benzyl)-N—CH$_2$— | Butyl | H | OMe | OMe | CH | N | N | O |
| II-159 | COOH | Phenyl | (N-(3,4-Di-OMe-PhenylCO)-N-Benzyl)-N—CH$_2$— | H | H | OMe | Me | CH | N | N | O |
| II-160 | COOH | Phenyl | (N-(3,4-Di-OMe-PhenylCO)-N-Benzyl)-N—CH$_2$— | H | H | H | OMe | CMe | N | N | O |
| II-161 | COOH | Phenyl | (N-(3,4-Di-OMe-PhenylCO)-N-Benzyl)-N—CH$_2$— | H | H | OMe | CH$_2$—CH$_2$—CH$_2$—C | N | N | O |
| II-162 | COOH | 4-F-Phenyl | (N-MeCO-N-(4-OMe-Phenyl))-N—CH$_2$— | H | H | Ethyl | Ethyl | CH | N | N | S |
| II-163 | COOH | Phenyl | (N-(2,6-Di-OMe-Phenyl-CH$_2$—CO)-N-Ethyl)-N—CH$_2$— | H | H | OMe | O—CH$_2$—CH$_2$—C | N | N | S |
| II-164 | COOH | Naphthyl, Naphthyl | (N-(3-Cl-4-Me-PhenylSO$_2$)-N-Me)-N—CH$_2$— | H | H | OMe | OMe | CH | N | N | S |
| II-165 | COOMe | Phenyl | (N-(2,6-Di-OMe-Phenyl-CH$_2$—CO)-N-Ethyl)-N—CH$_2$— | H | H | Ethyl | Ethyl | CH | N | N | O |
| II-166 | COOH | 4-F-Phenyl | (N-(2,6-Di-OMe-Phenyl-CH$_2$—CO)-N-Ethyl)-N—CH$_2$— | H | H | CF$_3$ | Me | CH | N | N | O |
| II-167 | COOH | Phenyl | (N-(2,6-Di-OMe-Phenyl-CH$_2$—CO)-N-Ethyl)-N—CH$_2$— | H | H | OMe | CF$_3$ | CH | N | N | O |
| II-168 | COOH | Phenyl | (N-(2,6-Di-OMe-Phenyl-CH$_2$—CO)-N-Ethyl)-N—CH$_2$— | H | H | Me | Me | CH | N | N | O |
| II-169 | COOH | Phenyl | 2,4,6-Tri-Me-PhenylCO-HN—CH$_2$— | H | H | Me | Me | CH | N | N | O |
| II-170 | COOH | Phenyl | (N-(2,6-Di-OMe-Phenyl-CH$_2$—CO)-N-Ethyl)-N—CH$_2$— | H | H | OMe | OMe | CH | N | N | O |

TABLE II-continued

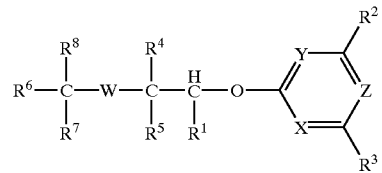

I

| No. | R¹ | R⁴, R⁵ | R⁶ | R⁷ | R⁸ | R² | R³ | Z | X | Y | W |
|---|---|---|---|---|---|---|---|---|---|---|---|
| II-171 | COOH | Phenyl | (N-(2-Me-3-Cl-4-OMe-PhenylCO)-N-Me)-N—CH₂— | Me | Me | OMe | Me | CH | N | N | O |
| II-172 | COOH | Phenyl | (N-(3-Me-2-Cl-4-OMe-PhenylCO)-N-Me)-N—CH₂— | H | H | H | Me | C—Me | N | N | O |
| II-173 | COOH | Phenyl | (N-(3-Me-4-Cl-5-OMe-PhenylCO)-N-Me)-N—CH₂— | H | H | OMe | CH₂—CH₂—CH₂—C | N | N | O |
| II-174 | COOH | Phenyl | (N-(3-Me-4-Cl-5-OMe-PhenylCO)-N-Me)-N—CH₂— | H | H | OMe | O—CH₂—CH₂—C | N | N | O |
| II-175 | COOH | 4-F-Phenyl | (N-(3,5-Di-Me-4-OMe-PhenylCO)-N-Me)-N—CH₂— | Me | Me | Ethyl | Ethyl | CH | N | N | S |
| II-176 | COOH | Phenyl | (N-(3,5-Di-Me-4-OMe-PhenylCO)-N-Me)-N—CH₂— | H | H | CF₃ | Me | CH | N | N | O |
| II-177 | COOH | Phenyl | (N-(3,5-Di-Me-4-OMe-PhenylCO)-N-Me)-N—CH₂— | H | H | OMe | CF₃ | CH | N | N | O |
| II-178 | COOH | Phenyl | (N-PhenylCO-N-MeOMe)-N—CH₂— | Ethyl | H | Me | Me | CH | N | N | O |
| II-179 | COOH | Phenyl | (N-PhenylCO-N-MeOMe)-N—CH₂— | H | H | OMe | OMe | CH | N | N | S |
| II-180 | COOH | Phenyl | (N-(4-OMe-PhenylCO)-N-MeOButyl)-N—CH₂— | H | H | OMe | Me | CH | N | N | O |
| II-181 | COOH | 4-F-Phenyl | (N-(3-OMe-PhenylCO)-N-MeOEthyl)-N—CH₂— | Ethyl | H | H | OMe | CH | N | N | O |
| II-182 | COOH | 4-F-Phenyl, 4 Cl Phenyl | (N-PhenylCO-N-Me)-N—CH₂— | H | H | OMe | Me | CH | N | N | O |
| II-183 | COOH | Phenyl | (N-(2-OMe-PhenylCO)-N-MeOMe)-N—CH₂— | H | H | OMe | CH₂—CH₂—CH₂—C | N | N | O |
| II-184 | COOH | Phenyl | (N-MeCO-N-Phenyl)-N—CH₂— | Me | Me | OMe | O—CH₂—CH₂—C | N | N | O |
| II-185 | COOH | Phenyl | (N-(3,4-Di-OMe-PhenylCO)-N-MeOMe)-N—CH₂— | H | H | OMe | O—CH₂—CH₂—C | N | N | O |
| II-186 | COOH | 4-F-Phenyl | (N-(3,4-Di-OMe-PhenylCO)-N-MeOEthyl)-N—CH₂— | H | H | Ethyl | Ethyl | CH | N | N | O |
| II-187 | COOH | Phenyl | (N-(3,4-Di-OMe-PhenylCO)-N-MeOButyl)-N—CH₂— | Me | Me | CF₃ | Me | CH | N | N | O |
| II-188 | COOH | Phenyl | (N-(3,4-Di-OMe-PhenylCO)-N-MeOMe)-N—CH₂— | H | H | OMe | CF₃ | CH | N | N | O |
| II-189 | COOH | Phenyl | (N-(3,4-Di-OMe-PhenylCO)-N-MeOMe)-N—CH₂— | H | H | Me | Me | CH | N | N | S |
| II-190 | COOH | Phenyl | 2,3-Di-Me-PhenylCO-HN—CH₂— | H | H | Me | Me | CH | N | N | O |
| II-191 | COOH | 4-F-Phenyl | (N-PhenylCO-N-(4-OMe-Phenyl-CH₂))-N—CH₂— | H | H | OMe | OMe | CH | N | N | O |
| II-192 | COOH | Phenyl | (N-PhenylCO-N-(4-OMe-Phenyl-CH₂))-N—CH₂— | Me | H | OMe | Me | CH | N | N | O |
| II-193 | COOH | Phenyl | (N-PhenylCO-N-(4-OMe-Phenyl-CH₂))-N—CH₂— | H | H | CH₂OH | Me | CH | N | N | O |
| II-194 | COOH | 4-F-Phenyl | (N-PhenylCO-N-(4-OMe-Phenyl-CH₂))-N—CH₂— | H | H | OMe | CH₂—CH₂—CH₂—C | N | N | O |
| II-195 | COOH | 4-F-Phenyl | PropylCO-HN—CH₂— | H | H | Ethyl | Ethyl | CH | N | N | S |
| II-196 | COOH | Phenyl | (N-PhenylCO-N-(3-OMe-Phenyl-CH₂))-N—CH₂— | H | H | OMe | O—CH₂—CH₂—C | N | N | S |
| II-197 | COOH | Phenyl | (N-PhenylCO-N-(2-OMe-Phenyl-CH₂))-N—CH₂— | H | H | Ethyl | Ethyl | CH | N | N | O |
| II-198 | COOH | Phenyl | (N-PhenylCO-N-(3-Me-Phenyl-CH₂))-N—CH₂— | H | H | CF₃ | Me | CH | N | N | O |
| II-199 | COOH | Phenyl | (N-PhenylCO-N-(4-Me-Phenyl-CH₂))-N—CH₂— | H | H | OMe | CF₃ | CH | N | N | O |
| II-200 | COOH | Phenyl | (N-EthylCO-N-Me)-N—CH₂— | H | H | OMe | CH₂—CH₂—CH₂—C | N | N | O |
| II-201 | COOMe | Phenyl | (N-PhenylCO-N-(4-OMe-Phenyl))-N—CH₂— | H | H | Me | Me | CH | N | N | S |
| II-202 | COOH | 4-F-Phenyl | (N-PhenylCO-N-(4-OMe-Phenyl))-N—CH₂— | H | H | OMe | OMe | CH | N | N | O |
| II-203 | COOH | Phenyl | (N-PhenylCO-N-(4-OMe-Phenyl))-N—CH₂— | H | H | OMe | Me | CH | N | N | O |
| II-204 | COOH | Phenyl | (N-PhenylCO-N-(4-OMe-Phenyl))-N—CH₂— | H | H | H | OMe | C—Me | N | N | O |
| II-205 | COOH | Phenyl | 3,5-Di-Cl-PhenylCO-HN—CH₂— | H | H | Me | Me | CH | N | N | O |
| II-206 | COOH | Phenyl | (N-PhenylCO-N-(3-OMe-Phenyl))-N—CH₂— | Ethyl | H | OMe | CH₂—CH₂—CH₂—C | N | N | O |
| II-207 | COOH | Phenyl | MeCO-HN—CH₂— | H | H | OMe | CH₂—CH₂—CH₂—C | N | N | O |
| II-208 | COOH | Phenyl | (N-PhenylCO-N-(2-OMe-Phenyl))-N—CH₂— | H | H | OMe | O—CH₂—CH₂—C | N | N | O |
| II-209 | COOH | Phenyl | (N-PhenylCO-N-(3-Me-Phenyl))-N—CH₂— | H | H | Ethyl | Ethyl | CH | N | N | O |
| II-210 | COOH | Phenyl | Naphthyl-1-CO-HN—CH₂— | H | H | Me | Me | CH | N | N | O |
| II-211 | COOH | Phenyl | (N-PhenylCO-N-(4-Me-Phenyl))-N—CH₂— | H | H | CF₃ | Me | CH | N | N | O |
| II-212 | COOH | Phenyl | CyclohexylCO-HN—CH₂— | Me | Me | OMe | O—CH₂—CH₂—C | N | N | O |
| II-213 | COOH | Phenyl | (N-2,6-DiethylphenylCO-N-Me)-N—CH₂— | H | H | OMe | CF₃ | CH | N | N | O |
| II-214 | COOH | 4-F-Phenyl | (N-2,6-DiisopropylphenylCO-N-Me)-N—CH₂— | H | H | Me | Me | CH | N | N | O |
| II-215 | COOH | Phenyl | (N-2,6-DiisopropylphenylCO-N-Me)-N—CH₂— | H | H | OMe | OMe | CH | N | N | O |
| II-216 | COOH | Phenyl | (N-MeCO-N-Me)-N—CH₂— | H | H | OMe | CH₂—CH₂—CH₂—C | N | N | O |
| II-217 | COOH | Phenyl | (N-2,6-DiethylphenylCO-N-Me)-N—CH₂— | H | H | OMe | Me | CH | N | N | O |
| II-218 | COOH | 4-F-Phenyl, Phenyl | 2,4,6-Tri-Me-PhenylCO-HN—CH₂— | H | H | Me | Me | CH | N | N | O |
| II-219 | COOMe | Phenyl | (N-2,6-DiethylphenylCO-N-Me)-N—CH₂— | H | H | CH₂OH | Me | CH | N | N | O |
| II-220 | COOH | Phenyl | 2,6-DiethylphenylCO-HN—CH₂— | H | H | OMe | CH₂—CH₂—CH₂—C | N | N | O |
| II-221 | COOH | Phenyl | 2,6-DiethylphenylCO-HN—CH₂— | Me | Me | OMe | O—CH₂—CH₂—C | N | N | O |
| II-222 | COOH | 4-F-Phenyl | 2,6-DiethylphenylCO-HN—CH₂— | H | H | Ethyl | Ethyl | CH | N | N | S |
| II-223 | COOH | Phenyl | 2,6-DiethylphenylCO-HN—CH₂— | H | H | CF₃ | Me | CH | N | N | O |
| II-224 | COOH | Phenyl | 2,6-DimethylphenylCO-HN—CH₂— | H | H | OMe | CF₃ | CH | N | N | O |
| II-225 | COOH | Phenyl | 2,6-DimethylphenylCO-HN—CH₂— | H | H | Me | Me | CH | N | N | O |

Example 59

Receptor binding data were measured by the binding assay described above for the compounds listed below. The results are shown in Table 3.

TABLE 3

| Receptor binding data ($K_i$ values) | | |
|---|---|---|
| Compound | $ET_A$ [nM/1] [sic] | $ET_B$ [nM/1] [sic] |
| I-109 | 0,4 | 142 |
| I-111 | 0,3 | 109 |
| I-347 | 3,8 | 155 |
| I-349 | 3,0 | 142 |
| I-307 | 1,6 | 10 |
| I-309 | 1 | 12 |

We claim:
1. A carboxylic acid of formula I

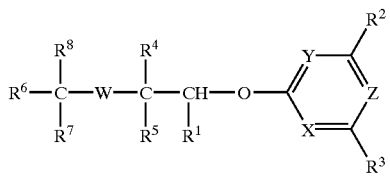

where
$R^1$ is tetrazole or a group

and R denotes
a) a radical $OR^9$ where $R^9$ is:
hydrogen, the cation of an alkali metal, the cation of an alkaline earth metal or a physiologically tolerated organic ammonium ion;
$C_3$-$C_8$-cycloalkyl, $C_1$-$C_8$-alkyl,
$CH_2$-phenyl which is unsubstituted or substituted,
$C_3$-$C_6$-alkenyl or a $C_3$-$C_6$-alkynyl group which is unsubstituted or substituted, or
phenyl which is unsubstituted or substituted;
b) a 5-membered heteroaromatic system linked via a nitrogen atom;
c) a group

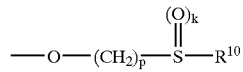

where k has a value of 0, 1 or 2, p has a value of 1, 2, 3 or 4, and $R^{10}$ is $C_1$-$C_4$-alkyl, $C_3$-$C_8$-cycloalkyl, $C_3$-$C_6$-alkenyl, $C_3$-$C_6$-alkynyl or unsubstituted or substituted phenyl;
d) a radical

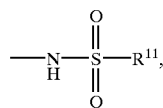

where $R^{11}$ is
$C_1$-$C_4$-alkyl, $C_3$-$C_6$-alkenyl, $C_3$-$C_6$-alkynyl, $C_3$-$C_8$-cycloalkyl, which radicals are unsubstituted or carry a $C_1$-$C_4$-alkoxy, $C_1$-$C_4$-alkylthio and/or a phenyl radical;
phenyl which is unsubstituted or substituted;
$R^2$ is hydrogen, hydroxyl, $NH_2$, $NH(C_1$-$C_4$-alkyl), $N(C_1$-$C_4$-alkyl)$_2$, halogen, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy or $C_1$-$C_4$-alkylthio, or $CR^2$ is linked to $CR^{12}$ as indicated under Z to give a 5- or 6-membered ring;
X is nitrogen or methine;
Y is nitrogen or methine;
Z is nitrogen or $CR^{12}$, where $R^{12}$ is hydrogen, halogen or $C_1$-$C_4$-alkyl, or $CR^{12}$ forms together with $CR^2$ or $CR^3$ a 5- or 6-membered alkylene or alkenylene ring which can be unsubstituted or substituted and in which in each case one or more methylene groups can be replaced by oxygen, sulfur, —NH or —N($C_1$-$C_4$-alkyl);
wherein two of X, Y and Z denote nitrogen and the third denotes methine or $CR^{12}$, respectively;
$R^3$ is hydrogen, hydroxyl, $NH_2$, $NH(C_1$-$C_4$-alkyl), $N(C_1$-$C_4$-alkyl)$_2$, halogen, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_1$-$C_4$-alkylthio; or $CR^3$ is linked to $CR^{12}$ as indicated under Z to give a 5- or 6-membered ring;
$R^4$ and $R^5$ are identical or different and denote:
phenyl or naphthyl each of which is unsubstituted or substituted, or
phenyl or naphthyl which are connected together in ortho positions by a direct linkage, a methylene, ethylene or ethenylene group, an oxygen or sulfur atom or an $SO_2$, NH or N-alkyl group,
$C_3$-$C_8$-cycloalkyl which is unsubstituted or substituted;
$R^6$ is a group

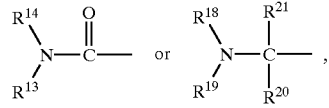

where
$R^{13}$ and $R^{14}$ are identical or different, and
$R^{13}$ is $C_1$-$C_8$-alkyl, $C_3$-$C_8$-alkenyl or $C_3$-$C_8$-alkynyl, wherein each of these radicals is substituted by one or more radicals selected from: carboxyl, amino, $C_1$-$C_4$-alkylcarbonyl, $C_1$-$C_4$-alkoxycarbonyl, $C_3$-$C_8$-alkylcarbonylalkyl, $C_3$-$C_8$-cycloalkyl, 1-indanyl, 2-indanyl, 1-tetrahydronaphthyl, 2-tetrahydronaphthyl, $NH(C_1$-$C_4$-alkyl), $N(C_1$-$C_4$-alkyl)$_2$, phenoxy and phenyl, the phenyl radicals in turn being unsubstituted or substituted by one or more radicals selected from: halogen, hydroxyl, mercapto, carboxyl, nitro, cyano, $C_1$-$C_4$-alkyl, $C_1$-$C_4$-haloalkyl, $C_1$-$C_4$-alkoxy, $C_1$-$C_4$-haloalkoxy, amino, $NH(C_1$-$C_4$-alkyl), $N(C_1$-$C_4$-alkyl)$_2$, and $C_1$-$C_4$-alkylthio;
$C_3$-$C_8$-cycloalkyl, which is unsubstituted or substituted by one or more radicals selected from: halogen, hydroxyl, mercapto, carboxyl, nitro, cyano, $C_1$-$C_4$-alkyl, $C_2$-$C_4$-alkenyl, $C_2$-$C_4$-alkynyl, $C_1$-$C_4$-alkoxy, $C_1$-$C_4$-alkylthio and $C_1$-$C_4$-haloalkoxy;
phenyl or naphthyl, each of which is unsubstituted or substituted by one or more radicals selected from: halogen, nitro, carbamoyl, mercapto, carboxyl, cyano, hydroxyl, amino, $R^{15}$, $C_1$-$C_4$-alkyl, $C_2$-$C_4$-alkenyl, $C_2$-$C_4$-alkynyl, $C_3$-$C_6$-alkenyloxy, $C_1$-$C_4$- haloalkyl, $C_3$–$C_6$-alkynyloxy, $C_1$–$C_4$-alkylcarbonyl, $C_1$–$C_4$-alkoxycarbonyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, methylenedioxy, ethylenedioxy and phenyl, where the phenyl ring is unsubstituted or substituted by one or more radicals selected from: halogen, nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^{14}$ is one of the groups indicated for $R^{13}$, or is $C_1$–$C_8$-alkyl, $C_3$–$C_8$-alkenyl or $C_3$–$C_8$-alkynyl, each of which is unsubstituted or substituted by one or more radicals selcted from: halogen, hydroxyl, mercapto, nitro, carbamoyl, cyano, $C_1$–$C_4$-alkoxy, $C_3$–$C_6$-alkenyloxy, $C_3$–$C_6$-alkynyloxy, $C_1$–$C_4$-alkylthio and $C_1$–$C_4$-haloalkoxy; or $R^{13}$ and $R^{14}$ together form a $C_3$–$C_7$-alkylene chain which is closed to a ring and which is unsubstituted or substituted by one or more radicals selected from: $C_1$–$C_4$-alkyl, $C_1$–$C_4$-alkylthio, $C_1$–$C_4$-alkoxy, $C_1$–$C_4$-haloalkyl and $C_1$–$C_4$-haloalkoxy, and where one methylene group of the alkylene chain is optionally replaced by oxygen, sulfur, nitrogen or N($C_1$–$C_4$-alkyl); or $R^{13}$ and $R^{14}$ together form a $C_3$–$C_7$-alkylene chain or $C_4$–$C_7$-alkenylene chain, which is closed to a ring, where each chain is unsubstituted or substituted by one to three $C_1$–$C_4$-alkyl radicals, and where each chain is fused to a phenyl ring which in turn is unsubstituted or substituted by one or more radicals selected from: halogen, $C_1$–$C_4$-alkyl, $C_1$–$C_4$-alkylthio, $C_1$–$C_4$-alkoxy, $C_1$–$C_4$-haloalkyl, $C_1$–$C_4$-haloalkoxy, hydroxyl, carboxyl and amino;

$R^7$ and $R^8$ are identical or different and denote: hydrogen, $C_1$–$C_4$-alkyl;

$R^{15}$ is $C_1$–$C_4$-alkyl, $C_1$–$C_4$-alkylthio, $C_1$–$C_4$-alkoxy, each of which is unsubstituted or carries one of the following radicals: hydroxyl, carboxyl, amino, NH($C_1$–$C_4$-alkyl), N($C_1$–$C_4$-alkyl)$_2$, carbamoyl and CON($C_1$–$C_4$-alkyl)$_2$;

$R^{18}$ is hydrogen; $C_1$–$C_8$-alkyl, $C_3$–$C_8$-alkenyl or $C_3$–$C_8$-alkynyl, phenyl, naphthyl, $C_3$–$C_8$-cycloalkyl, where these radicals are unsubstituted or substituted;

$R^{19}$ is $C_1$–$C_8$-alkylcarbonyl, $C_2$–$C_8$-alkenylcarbonyl, $C_2$–$C_8$-alkynylcarbonyl, benzyloxycarbonyl, $C_3$–$C_8$-cycloalkylcarbonyl, phenylcarbonyl or naphthylcarbonyl, where the abovementioned radicals are unsubstituted or substituted;

$C_1$–$C_8$-alkylsulfonyl, $C_3$–$C_8$-alkenylsulfonyl or $C_3$–$C_8$-alkynylsulfonyl, phenylsulfonyl or naphthylsulfonyl, each of which is unsubstituted or substituted; $C_3$–$C_8$-cycloalkylsulfonyl;

$R^{20}$ is hydrogen, $C_1$–$C_4$-alkyl which is unsubstituted or substituted;

$R^{21}$ is hydrogen, $C_1$–$C_4$-alkyl;

W is sulfur or oxygen, or a physiologically tolerated salt or an enantiomerically pure or diastereomerically pure form.

2. A pharmaceutical composition which is suitable for the treatment of a disease in which an endothelin level is elevated, comprising at least one of the compounds of formula I defined in claim 1 and conventional medicinal auxiliaries.

3. A method of blocking an endothelin receptor which comprises admisitering an effective amount of the compound of formula I as defined claim 1.

4. A method of producing the composition defined in claim 2 which comprises processing an effective amount of the compound of formula I with conventional medicinal auxiliaries.

5. A method of treating a disease in which endothelin contributes to cause and/or progression, which comprises administering an effective amount of the compound of formula I defined in claim 1.

6. A method of claim 5 for treating a disease selected from the group of chronic heart failure, restenosis, high blood pressure, pulmonary hypertension, acute kidney failure, chronic kidney failure, cerebral ischemia, benign prostate hyperplasia and prostate cancer.

7. A composition comprising effective amounts of the compound of formula I defined in claim 1 and at least one further active substance selected from the group of inhibitors of the renin-angiotensin system.

8. The composition defined in claim 7, wherein the inhibitor of the renin-angiotensin system is selected from the group consisting of renin inhibitors, angiotensin II antagonists, angiotensin converting enzyme (ACE) inhibitors, mixed ACE/neutral endopeptidase (NEP) inhibitors, β-blockers, diuretics, calcium antagonists and VEGF-blocking substances.

9. The carboxylic acid of formula I defined in claim 1, wherein $R^2$ is hydrogen, hydroxyl, halogen, N($C_1$–$C_4$-alkyl)$_2$, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-hydroxyalkyl, or $CR^2$ is linked to $CR^{12}$ as indicated under Z to give a 5- or 6-membered ring;

Z is nitrogen or $CR^{12}$, where $R^{12}$ is hydrogen, fluorine or $C_1$–$C_4$-alkyl, or $CR^{12}$ forms together with $CR^2$ or $CR^3$ a ring which is unsubstituted or substituted by one or two methyl groups, and wherein $R^{12}$–$R^2$ or $R^{12}$–$R^3$ represent a biradical selected from: —$CH_2$—$CH_2$—O—, —$CH_2$—$CH_2$—$CH_2$—O—, —CH=CH—O—, —CH=CH—$CH_2$O—, —CH($CH_3$)—CH($CH_3$)—O—, —CH=C($CH_3$)—O—, —C($CH_3$)=C($CH_3$)—O— and —C($CH_3$)=C($CH_3$)—S;

$R^3$ is hydrogen, hydroxyl, halogen, N($C_1$–$C_4$-alkyl)$_2$, $C_1$–$C_4$-alkyl, $C_1$–$C_4$-alkoxy, $C_1$–$C_4$-alkylthio, $C_1$–$C_4$-haloalkyl, $C_1$–$C_4$-hydroxyalkyl, $C_1$–$C_4$-haloalkoxy, or $CR^3$ is linked to $CR^{10}$ as indicated under Z to give a 5- or 6-membered ring;

$R^4$ and $R^5$ are identical or different and denote phenyl or naphthyl, each of which is unsubstituted or substituted by one or more radicals selected from: halogen, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$ and phenyl which is unsubstituted or substituted by one to three radicals selected from: halogen, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio; or phenyl or naphthyl which are connected together in ortho positions by a direct linkage, a methylene, ethylene or ethenylene group, an oxygen or sulfur atom or an $SO_2$—, NH— or N-alkyl group; or $C_3$–$C_8$-cycloalkyl;

$R^{13}$ is $C_1$–$C_8$-alkyl, $C_3$–$C_8$-alkenyl or $C_3$–$C_8$-alkynyl, wherein each of these radicals is substituted by one or more radicals selected from: carboxyl, amino, $C_1$–$C_4$-alkylcarbonyl, $C_1$–$C_4$-alkoxycarbonyl, $C_3$–$C_8$-cycloalkyl, NH($C_1$–$C_4$-alkyl), N($C_1$–$C_4$-alkyl)$_2$, phenoxy and phenyl, the phenyl radicals in turn being unsubstituted or substituted by one or more radicals selected from: halogen, hydroxyl, carboxyl, cyano, $C_1$–$C_4$-alkyl, $C_1$–$C_4$-haloalkyl, $C_1$–$C_4$-alkoxy, $C_1$–$C_4$-haloalkoxy, NH($C_1$–$C_4$-alkyl), N($C_1$–$C_4$-alkyl)$_2$, and $C_1$–$C_4$-alkylthio;

$C_3$–$C_8$-cycloalkyl, which is unsubstituted or substituted by one or more radicals selected from: halogen, hydroxyl, mercapto, carboxyl, cyano, $C_1$–$C_4$-alkyl, $C_1$–$C_4$-alkoxy, $C_1$–$C_4$-alkylthio and $C_1$–$C_4$-haloalkoxy;

phenyl or naphthyl, each of which is unsubstituted or substituted by one or more radicals selected from: halogen, carboxyl, hydroxyl, amino, $R^{15}$, $C_1$–$C_4$-alkyl, $C_1$–$C_4$-haloalkyl, $C_1$–$C_4$-alkylcarbonyl, $C_1$–$C_4$-alkoxycarbonyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, methylenedioxy, ethylenedioxy and phenyl, where the phenyl ring is unsubstituted or substituted by one to three radicals selected from: halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^{14}$ is one of the groups indicated for $R^{13}$, or is $C_1$–$C_8$-alkyl, $C_3$–$C_8$-alkenyl or $C_3$–$C_8$-alkynyl, each of which is unsubstituted or substituted by one or more radicals selcted from: halogen, hydroxyl, mercapto, cyano, $C_1$–$C_4$-alkoxy, $C_1$–$C_4$-alkylthio and $C_1$–$C_4$-haloalkoxy; or $R^{13}$ and $R^{14}$ together form a $C_3$–$C_7$-alkylene chain which is closed to a ring and which is unsubstituted or substituted by one or more radicals selected from: $C_1$–$C_4$-alkyl and $C_1$–$C_4$-haloalkyl, and where one methylene group of the alkylene chain is optionally replaced by oxygen or sulfur; or $R^{13}$ and $R^{14}$ together form a radical selected from: 7-azabicyclo[4.2.0]octa-1,3,5-triene, 2,3-dihydroindole, indole, 1,3-dihydroisoindole, 1,2,3,4-tetrahydroquinoline, 1,2,3,4-tetrahydroisoquinoline, which radical is unsubstituted or substituted by one to three groups selected from: halogen, $C_1$–$C_4$-alkyl, $C_1$–$C_4$-alkoxy, $C_1$–$C_4$-haloalkyl, $C_1$–$C_4$-haloalkoxy, hydroxyl and carboxyl;

$R^{15}$ is $C_1$–$C_4$-alkyl, $C_1$–$C_4$-alkoxy, each of which is unsubstituted or carries one of the following radicals: hydroxyl, carboxyl, amino, NH($C_1$–$C_4$-alkyl), N($C_1$–$C_4$-alkyl)$_2$, carbamoyl and CON($C_1$–$C_4$-alkyl)$_2$;

$R^{18}$ is hydrogen;

$C_1$–$C_4$-alkyl, $C_3$–$C_4$-alkenyl or $C_3$–$C_4$-alkynyl, where each of these radicals is unsubstituted or substituted by one or more radicals selected from: halogen, $C_1$–$C_4$-alkoxy, $C_1$–$C_4$-alkylthio, $C_1$–$C_4$-haloalkoxy, $C_3$–$C_8$-cycloalkyl, phenoxy and phenyl, where the phenyl radicals in turn are unsubstituted or substituted by one to three groups selected from: halogen, hydroxyl, $C_1$–$C_4$-alkyl, $C_1$–$C_4$-haloalkyl, $C_1$–$C_4$-alkoxy and $C_1$–$C_4$-alkylthio;

$C_3$–$C_8$-cycloalkyl, where each of these radicals is unsubstituted or substituted by one or more $C_1$–$C_4$-alkyl groups;

phenyl or naphthyl, each of which is unsubstituted or substituted by one or more radicals selected from: halogen, hydroxyl, $R^{15}$, $C_1$–$C_4$-alkyl, $C_1$–$C_4$-alkoxycarbonyl, $C_1$–$C_4$-alkoxy, $C_1$–$C_4$-alkylthio, methylenedioxy, ethylenedioxy and phenyl which is unsubstituted or substituted by one to three radicals selected from halogen, $C_1$–$C_4$-alkyl, $C_1$–$C_4$-haloalkyl and $C_1$–$C_4$-alkoxy;

$R^{19}$ is $C_1$–$C_4$-alkylcarbonyl, $C_2$–$C_4$-alkenylcarbonyl or $C_2$–$C_4$-alkynylcarbonyl, where each of these radicals is unsubstituted or substituted by one or more radicals selected from: halogen, $C_1$–$C_4$-alkoxy, $C_3$–$C_8$-cycloalkyl, phenoxy and phenyl, where the phenyl rings in turn are unsubstituted or substituted by one to three radicals selected from: halogen, $C_1$–$C_4$-alkyl, $C_1$–$C_4$-haloalkyl, $C_1$–$C_4$-alkoxy and $C_1$–$C_4$-alkylthio;

$C_3$–$C_8$-cycloalkylcarbonyl, where each of these radicals is unsubstituted or substituted by one or more $C_1$–$C_4$-alkyl groups; phenylcarbonyl or naphthylcarbonyl, each of which is unsubstituted or substituted by one or more radicals selected from: halogen, cyano, hydroxyl, $R^{15}$, $C_1$–$C_4$-alkyl, $C_1$–$C_4$-haloalkyl, $C_1$–$C_4$-alkylcarbonyl, $C_1$–$C_4$-alkoxycarbonyl, $C_1$–$C_4$-alkoxy, phenoxy, $C_1$–$C_4$-alkylthio, methylenedioxy, ethylenedioxy and phenyl which is unsubstituted or substituted by one to three radicals selected from: halogen, $C_1$–$C_4$-alkyl, $C_1$–$C_4$-haloalkyl, $C_1$–$C_4$-alkoxy and $C_1$–$C_4$-alkylthio;

$C_1$–$C_4$-alkylsulfonyl, where each of these radicals is unsubstituted or substituted by one or more radicals selected from: halogen, $C_1$–$C_4$-alkoxy and phenyl, where the phenyl radical in turn is unsubstituted or substituted by one to three radicals selected from: halogen, $C_1$–$C_4$-alkyl, $C_1$–$C_4$-haloalkyl, $C_1$–$C_4$-alkoxy and $C_1$–$C_4$-alkylthio; $C_3$–$C_8$-cycloalkylsulfonyl;

phenylsulfonyl or naphthylsulfonyl, each of which is unsubstituted or substituted by one or more radicals selected from: halogen, cyano, $R^{15}$, $C_1$–$C_4$-alkyl, $C_1$–$C_4$-alkoxy, methylenedioxy, ethylenedioxy and phenyl which is unsubstituted or substituted by one to three radicals selected from: halogen, $C_1$–$C_4$-alkyl, $C_1$–$C_4$-haloalkyl, $C_1$–$C_4$-alkoxy and $C_1$–$C_4$-alkylthio;

$R^{20}$ is hydrogen, or $C_1$–$C_4$-alkyl, where each of these radicals is optionally monosubstituted by: hydroxyl, mercapto, carboxyl, amino, $C_3$–$C_8$-cycloalkyl, indolyl, phenoxy or phenyl, wherein the aryl radicals in turn are unsubstituted or substituted by one to three groups selected from: halogen, hydroxyl, mercapto, carboxyl, $C_1$–$C_4$-alkyl, $C_1$–$C_4$-alkoxy, amino and $C_1$–$C_4$-alkylthio.

10. The carboxylic acid of formula I defined in claim 1, wherein $R^2$ is trifluoromethyl, $C_1$–$C_4$-alkyl, $C_1$–$C_4$-alkoxy, $C_1$–$C_4$-alkylthio, hydroxymethyl, or $CR^2$ is linked to $CR^{12}$ as indicated under Z to give a 5- or 6-membered ring;

Z is nitrogen or $CR^{12}$, where $R^{12}$ is hydrogen, fluorine or $C_1$–$C_4$-alkyl, or $CR^{12}$ forms together with $CR^2$ or $CR^3$ a ring which is unsubstituted or substituted by one or two methyl groups, and wherein $R^{12}$–$R^2$ or $R^{12}$–$R^3$ represent a biradical selected from: —$CH_2$—$CH_2$—O—, —CH=CH—O—, —CH($CH_3$)—CH($CH_3$)—O—, —C($CH_3$)=C($CH_3$)—O—;

$R^3$ is hydrogen, hydroxyl, halogen, N($C_1$–$C_4$-alkyl)$_2$, $C_1$–$C_4$-alkyl, $C_1$–$C_4$-alkoxy, $C_1$–$C_4$-alkylthio, $C_1$–$C_4$-haloalkyl, $C_1$–$C_4$-hydroxyalkyl, $C_1$–$C_4$-haloalkoxy, or $CR^3$ is linked to $CR^{10}$ as indicated under Z to give a 5- or 6-membered ring;

$R^4$ and $R^5$ are identical or different and denote phenyl or naphthyl, each of which is unsubstituted or substituted by one or more radicals selected from: halogen, hydroxyl, $C_1$–$C_4$-alkyl, $C_1$–$C_4$-haloalkyl, $C_1$–$C_4$-alkoxy, $C_1$–$C_4$-haloalkoxy, phenoxy, NH($C_1$–$C_4$-alkyl), N($C_1$–$C_4$-alkyl)$_2$ and phenyl which is unsubstituted or substituted by one to three radicals selected from: halogen, $C_1$–$C_4$-alkyl, $C_1$–$C_4$-haloalkyl, $C_1$–$C_4$-alkoxy and $C_1$–$C_4$-haloalkoxy; or phenyl or naphthyl which are connected together in ortho positions by a direct linkage, a methylene, ethylene or ethenylene group, an oxygen or sulfur atom or an $SO_2$—, NH— or N-alkyl group; or $C_5$–$C_7$-cycloalkyl;

$R^{13}$ is $C_1$–$C_5$-alkyl, $C_3$–$C_5$-alkenyl or $C_3$–$C_5$-alkynyl, wherein each of these radicals is substituted by one or more radicals selected from: carboxyl, amino, $C_3$–$C_8$-cycloalkyl, NH($C_1$–$C_4$-alkyl), N($C_1$–$C_4$-alkyl)$_2$, phenoxy and phenyl, the phenyl radicals in turn being unsubstituted or substituted by one to three radicals selected from: halogen, hydroxyl, $C_1$–$C_4$-alkyl, $C_1$–$C_4$-haloalkyl, $C_1$–$C_4$-alkoxy, $C_1$–$C_4$-haloalkoxy and N($C_1$–$C_4$-alkyl)$_2$;

$C_3$–$C_8$-cycloalkyl, which is unsubstituted or substituted by one or more radicals selected from: halogen, carboxyl, $C_1$–$C_4$-alkyl, $C_1$–$C_4$-alkoxy and $C_1$–$C_4$-haloalkoxy; phenyl which is unsubstituted or substituted by one to three radicals selected from: halogen, carboxyl, hydroxyl, amino, $R^{15}$, $C_1$–$C_4$-alkyl, $C_1$–$C_4$-haloalkyl, $C_1$–$C_4$-alkylcarbonyl, $C_1$–$C_4$-alkoxycarbonyl, $C_1$–$C_4$-alkoxy, $C_1$–$C_4$-haloalkoxy, $C_1$–$C_4$-alkylthio, NH($C_1$–$C_4$-alkyl), N($C_1$–$C_4$-alkyl)$_2$, methylenedioxy, ethylenedioxy and phenyl, where the phenyl ring is unsubstituted or substituted by one to three radicals selected from: halogen, $C_1$–$C_4$-alkyl, $C_1$–$C_4$-alkoxy and $C_1$–$C_4$-alkylthio;

$R^{14}$ is one of the groups indicated for $R^{13}$, or is $C_1$–$C_5$-alkyl, $C_3$–$C_5$-alkenyl or $C_3$–$C_5$-alkynyl, each of which is unsubstituted or substituted by one or more radicals selcted from: halogen, hydroxyl, $C_1$–$C_4$-alkoxy and $C_1$–$C_4$-haloalkoxy; or $R^{13}$ and $R^{14}$ together form a $C_3$–$C_7$-alkylene chain which is closed to a ring and which is unsubstituted or substituted by one or more $C_1$–$C_4$-alkyl radicals, and where one methylene group of the alkylene chain is optionally replaced by oxygen or sulfur; or $R^{13}$ and $R^{14}$ together form a radical selected from: 2,3-dihydroindole, indole, 1,3-dihydroisoindole, 1,2,3,4-tetrahydroquinoline, 1,2,3,4-tetrahydroisoquinoline, which radical is unsubstituted or substituted by one to three groups selected from: halogen, $C_1$–$C_4$-alkyl, $C_1$–$C_4$-alkoxy, $C_1$–$C_4$-haloalkoxy, hydroxyl and carboxyl;

$R^{15}$ is $C_1$–$C_4$-alkyl, $C_1$–$C_4$-alkoxy, each of which is unsubstituted or carries one of the following radicals: hydroxyl, NH($C_1$–$C_4$-alkyl), N($C_1$–$C_4$-alkyl)$_2$, carbamoyl and CON($C_1$–$C_4$-alkyl)$_2$;

$R^{18}$ is hydrogen;

$C_1$–$C_4$-alkyl, where each of these radicals is unsubstituted or substituted by one to three radicals selected from: halogen, $C_1$–$C_4$-alkoxy, $C_1$–$C_4$-alkylthio, $C_3$–$C_8$-cycloalkyl, phenoxy and phenyl, where the phenyl radicals in turn are unsubstituted or substituted by one to three groups selected from: halogen, $C_1$–$C_4$-alkyl and $C_1$–$C_4$-alkoxy;

$C_3$–$C_8$-cycloalkyl; phenyl which is unsubstituted or substituted by one to three radicals selected from: halogen, hydroxyl, $R^{15}$, $C_1$–$C_4$-alkyl, $C_1$–$C_4$-alkoxycarbonyl, $C_1$–$C_4$-alkoxy, methylenedioxy, ethylenedioxy and phenyl which is unsubstituted or substituted by one to three radicals selected from halogen, $C_1$–$C_4$-alkyl, trifluoromethyl and $C_1$–$C_4$-alkoxy;

$R^{19}$ is $C_1$–$C_4$-alkylcarbonyl, where each of these radicals is unsubstituted or substituted by one to three radicals selected from: halogen, $C_1$–$C_4$-alkoxy, $C_3$–$C_8$-cycloalkyl and phenyl, where the phenyl ring in turn is unsubstituted or substituted by one to three radicals selected from: halogen, $C_1$–$C_4$-alkyl and $C_1$–$C_4$-alkoxy;

$C_3$–$C_8$-cycloalkylcarbonyl;

phenylcarbonyl or naphthylcarbonyl, each of which is unsubstituted or substituted by one or more radicals selected from: halogen, $R^{15}$, $C_1$–$C_4$-alkyl, $C_1$–$C_4$-alkoxy, phenoxy, methylenedioxy, ethylenedioxy and phenyl which is unsubstituted or substituted by one to three radicals selected from: halogen, $C_1$–$C_4$-alkyl and $C_1$–$C_4$-alkoxy;

$C_1$–$C_4$-alkylsulfonyl, where each of these radicals is unsubstituted or substituted by one to three radicals selected from: halogen, $C_1$–$C_4$-alkoxy and phenyl, where the phenyl radical in turn is unsubstituted or substituted by one to three radicals selected from: halogen, $C_1$–$C_4$-alkyl, $C_1$–$C_4$-alkoxy and $C_1$–$C_4$-alkylthio;

$C_3$–$C_8$-cycloalkylsulfonyl;

phenylsulfonyl or naphthylsulfonyl, each of which is unsubstituted or substituted by one to three radicals selected from: halogen, $R^{15}$, $C_1$–$C_4$-alkyl, $C_1$–$C_4$-alkoxy, methylenedioxy, ethylenedioxy and phenyl;

$R^{20}$ is hydrogen or $C_1$–$C_4$-alkyl.

11. The carboxylic acid of formula I defined in claim 1, wherein $R^6$ is a group

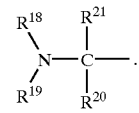

12. The carboxylic acid of formula I defined in claim 9, wherein $R^6$ is a group

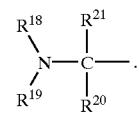

13. The carboxylic acid of formula I defined in claim 10, wherein $R^6$ is a group

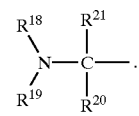

* * * * *

UNITED STATES PATENT AND TRADEMARK OFFICE
CERTIFICATE OF CORRECTION

PATENT NO. : 6,509,341 B1
DATED : January 21, 2003
INVENTOR(S) : Amberg et al.

It is certified that error appears in the above-identified patent and that said Letters Patent is hereby corrected as shown below:

<u>Title page, Item [54] and Column 1, lines 1-4,</u>
The title is incorrect. It should read as follows:
-- CARBOXYLIC ACID DERIVATIVES, CARRYING AMIDE SIDE-CHAINS; PRODUCTION AND USE AS ENDOTHELIN RECEPTOR ANTAGNONISTS --

Signed and Sealed this

Twenty-ninth Day of July, 2003

JAMES E. ROGAN
*Director of the United States Patent and Trademark Office*